US011975005B2

(12) United States Patent
Stewart et al.

(10) Patent No.: US 11,975,005 B2
(45) Date of Patent: *May 7, 2024

(54) TREATMENT OF RESPIRATORY DISEASES

(71) Applicant: TIANLI BIOTECH PTY LTD, Victoria (AU)

(72) Inventors: Alastair Stewart, Victoria (AU); Christine Keenan, Victoria (AU); Trudi Harris, Victoria (AU)

(73) Assignee: TIANLI BIOTECH PTY LTD, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 18/087,672

(22) Filed: Dec. 22, 2022

(65) Prior Publication Data

US 2023/0146291 A1 May 11, 2023

Related U.S. Application Data

(63) Continuation of application No. 16/917,581, filed on Jun. 30, 2020, now Pat. No. 11,564,925, which is a continuation of application No. 15/559,360, filed as application No. PCT/AU2016/050209 on Mar. 23, 2016, now Pat. No. 10,722,513.

(30) Foreign Application Priority Data

Mar. 23, 2015 (AU) .................................. 2015901032

(51) Int. Cl.
| | | |
|---|---|---|
| *C07D 403/04* | (2006.01) | |
| *A61K 31/4439* | (2006.01) | |
| *A61K 31/444* | (2006.01) | |
| *A61K 31/506* | (2006.01) | |
| *A61K 31/519* | (2006.01) | |
| *A61K 31/573* | (2006.01) | |
| *A61K 31/58* | (2006.01) | |
| *A61K 45/06* | (2006.01) | |
| *A61P 35/00* | (2006.01) | |
| *C07D 405/14* | (2006.01) | |
| *C07D 413/14* | (2006.01) | |
| *C07D 487/04* | (2006.01) | |

(52) U.S. Cl.
CPC ........ *A61K 31/519* (2013.01); *A61K 31/4439* (2013.01); *A61K 31/444* (2013.01); *A61K 31/506* (2013.01); *A61K 31/573* (2013.01); *A61K 31/58* (2013.01); *A61K 45/06* (2013.01); *A61P 35/00* (2018.01); *C07D 403/04* (2013.01); *C07D 405/14* (2013.01); *C07D 413/14* (2013.01); *C07D 487/04* (2013.01)

(58) Field of Classification Search
CPC .................................................. C07D 403/04
See application file for complete search history.

(56) References Cited

U.S. PATENT DOCUMENTS

| | | | |
|---|---|---|---|
| 5,593,991 | A | 1/1997 | Adams et al. |
| 5,593,992 | A | 1/1997 | Adams et al. |
| 5,837,699 | A | 11/1998 | Sequeira et al. |
| 6,057,307 | A | 5/2000 | Sequeira et al. |
| 6,218,537 | B1 | 4/2001 | Adams et al. |
| 6,369,068 | B1 | 4/2002 | Adams et al. |
| 6,598,603 | B1 | 7/2003 | Andersson et al. |

(Continued)

FOREIGN PATENT DOCUMENTS

| | | |
|---|---|---|
| CN | 103784451 A | 5/2014 |
| EP | 2589385 A1 | 5/2013 |

(Continued)

OTHER PUBLICATIONS

Interstitial lung disease overview [online] retrieved from the internet on Jul. 14, 2023 URL https://www.mayoclinic.org/diseases-conditions/interstitial-lung-disease/symptoms-causes/syc-20353108.*

Interstitial lung disease causes [online] retrieved from the internet on Jul. 14, 2023 (see URL https://www.nhlbi.nih.gov/health/interstitial-lung-diseases/causes).*

Barnes et al., "How Do Corticosteroids Work in Asthma?" Annals of Internal Medicine, 2003, 139:359-370.

Sur et al., "Treatment of Allergic Rhinitis", American Family Physician, 2010, 81(12):1440-1446.

(Continued)

*Primary Examiner* — Shawquia Jackson
(74) *Attorney, Agent, or Firm* — James S. Keddie; Bozicevic, Field & Francis LLP

(57) ABSTRACT

The present invention relates to compositions, methods and kits for the treatment of respiratory disease. In particular, the compositions, methods and kits are particularly useful, but not limited to, the treatment or prevention of exacerbations of asthma and chronic obstructive pulmonary disease. The present invention provides a method of treating or preventing a respiratory disease in a subject in need thereof, the method comprising administering to the subject a therapeutically effective amount of an inhibitor of casein kinase 1, thereby treating or preventing a respiratory disease in a subject. The present invention also provides a method of treating or preventing a respiratory disease in a subject in need thereof, the method comprising administering to the subject a therapeutically effective amount of an inhibitor of ALK5, thereby treating or preventing a respiratory disease in a subject, wherein the inhibitor is administered directly to the airway and/or lungs. The present invention also provides a method of treating or preventing a condition of the airway or lung involving fibrosis in a subject in need thereof, the method comprising administering to the subject a therapeutically effective amount of an inhibitor of casein kinase 1 or an inhibitor of ALK5, thereby treating or preventing a condition of the airway or lung involving fibrosis in a subject.

8 Claims, 36 Drawing Sheets

(56) References Cited

U.S. PATENT DOCUMENTS

| | | |
|---|---|---|
| 2004/0209805 A1 | 10/2004 | Phillips et al. |
| 2008/0188443 A1 | 8/2008 | Cheng et al. |
| 2009/0099237 A1 | 4/2009 | Aud et al. |
| 2011/0098272 A1 | 4/2011 | Subramanyam et al. |
| 2011/0166153 A1 | 7/2011 | Watterson et al. |
| 2012/0184557 A1 | 7/2012 | Meijer et al. |
| 2013/0115309 A1 | 5/2013 | Grandori et al. |
| 2019/0175596 A1 | 6/2019 | de Maeyer et al. |

FOREIGN PATENT DOCUMENTS

| | | |
|---|---|---|
| JP | 2016193861 A | 11/2016 |
| WO | WO 95/02591 A1 | 1/1995 |
| WO | WO 96/21654 A1 | 7/1996 |
| WO | WO 96/40143 A1 | 12/1996 |
| WO | WO 97/35856 A1 | 10/1997 |
| WO | WO 99/01136 A1 | 1/1999 |
| WO | WO 99/32121 A1 | 7/1999 |
| WO | WO 2004/028545 A1 | 4/2004 |
| WO | WO 2005/074918 A1 | 8/2005 |
| WO | WO 2005/103240 A1 | 11/2005 |
| WO | WO 2008/071605 A2 | 6/2008 |
| WO | WO 2010/043981 A1 | 4/2010 |
| WO | WO2011127202 A2 | 10/2011 |
| WO | WO 2012/080727 A2 | 6/2012 |
| WO | WO 2014/018691 A1 | 1/2014 |
| WO | WO2014023271 A1 | 2/2014 |
| WO | WO 2014/100533 A1 | 6/2014 |
| WO | WO 2014/100540 A1 | 6/2014 |
| WO | WO2014054526 A2 | 4/2015 |
| WO | WO2015114638 A2 | 8/2015 |
| WO | WO2016149756 A1 | 9/2016 |
| WO | WO2017083971 A1 | 5/2017 |
| WO | WO2018081575 A1 | 5/2018 |
| WO | WO2018201192 A1 | 11/2018 |
| WO | WO2020049190 A1 | 3/2020 |

OTHER PUBLICATIONS

Yamaya, "Virus Infection-Induced Bronchial Asthma Exacerbation", Pulmonary Medicine, vol. 2012, Article ID 834826 (online journal) [retrieved from internet on May 11, 2016] <URL: http://www.hindawi.com/journals/pm/2012/834826/>.

Barnes, "Inhaled Corticosteroids", Pharmaceuticals, 2010, 3:514-540.

Buckingham et al., "A Randomized, Double-Blink, Placebo-Controlled Trial of Dexamethasone in Severe Respiratory Syncytial Virus (RSV) Infection: Effects on RSV Quantity and Clinical Outcome", The Journal of Infectious Diseases, 2002, 185: 1222-1228.

Marchant et al., "Toll-Like Receptor 4-Mediated Activation of p38 Mitogen-Activated Protein Kinase Is a Determinant of Respiratory Virus Entry and Tropism", Journal Of Virology, 2010, 84(21): 11359-11373.

Richard C. Boucher, "Muco-Obstructive Lung Diseases", The New England Journal of Medicine, May 2019, 380;20, pp. 1941-1953.

James M. Littlewood, "History of cystic fibrosis", CRC Press, FL, 2007, 12 pages.

Bell et al., "The future of cystic fibrosis care: a global perspective", The Lancet Respiratory Medicine Commission, 2020, 8: 65-124.

Mccarron et al., "Airway disease phenotypes in animal models of cystic fibrosis", Respiratory Research, 2018, 19:54, https://doi.org/10.1186/s12931-018-0750-y, 12 pages.

Sheppard et al., "Structure and Function of the CFTR Chloride Channel", Physiological Reviews, vol. 79, Suppl., No. 1, 1999, S23-S45.

Vogt et al., "The specificities of small molecule inhibitors of the TGFß and BMP pathways", Cellular Signalling, 2011, 23: 1831-1842.

Wuyts et al., "Combination therapy: the future of management for idiopathic pulmonary fibrosis?", Lancet Respir Med, 2014, 2: 933-942.

Ziobro et al., "Ceramide mediates lung fibrosis in cystic fibrosis", Biochemical and Biophysical Research Communications, 2013, 434: 705-709.

Badura et al., "An Inhibitor of Casein Kinase 1ε Induces Phase Delays in Circadian Rhythms under Free-Running and Entrained Conditions", The Journal of Pharmacology and Experimental Therapeutics, 2007, 322(2): 730-738.

Walton et al., "Selective Inhibition of Casein Kinase 1ε Minimally Alters Circadian Clock Period", The Journal of Pharmacology and Experimental Therapeutics, 2009, 330(2): 430-439.

CAS Registry No. 1349012-04-9, STN Entry Date: Dec. 5, 2011; 2-Pyrimidinamine, N-(3-[1,1'-biphenyl]-3-ylpropyl)-4-[1-cyclohexyl-4-(4-fluorophenyl)-1H-imidazol-5-yl].

Database PubChem Compound [Online] Oct. 25, 2006 (Oct. 25, 2006), retrieved from NCBI, Database accession No. 9959143.

Database Registry [Online] Chemical Abstracts Service, (Dec. 5, 2011), retrieved from STN Databse accession No. 1349012-04-9.

Keenan et al. "Casein kinase 1α/ε inhibitor, PF670462 attenuates the fibrogenic effects of transforming growth factor-β in pulmonary fibrosis", Frontiers in Pharmacology, Jul. 2018, 9(738), 15 pages.

Kim et al., "Synthesis and biological evaluation of trisubstituted imidazole derivatives as inhibitors if p38a mitogen-activated protein kinase", Bioorganic & Medicinal Chemistry Letters, 18 (2008) 4006-4010.

Asthma [online] retrieved from the internet on Apr. 27, 2022, URL: https//www.mayoclinic.org/diseases-conditions/asthma/symptoms-causes/syc-20369653?p=1.

* cited by examiner

Figure 10
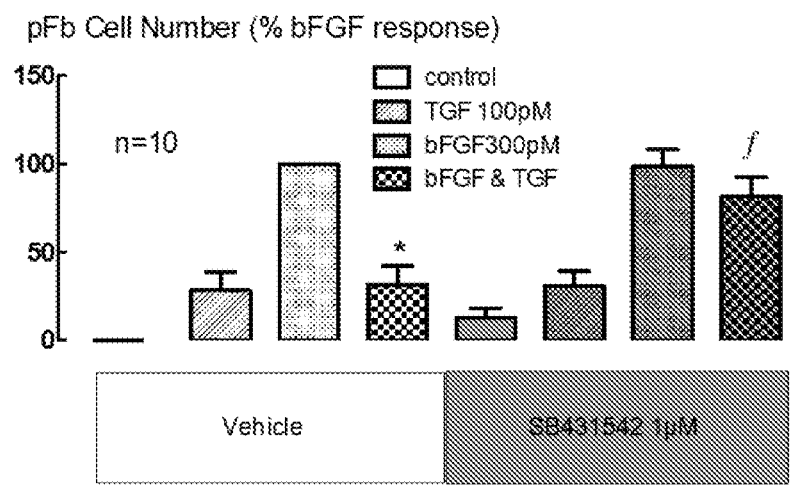
\* p<0.05 to bFGF ANOVA
ƒ p<0.05 to bFGF/TGF ANOVA
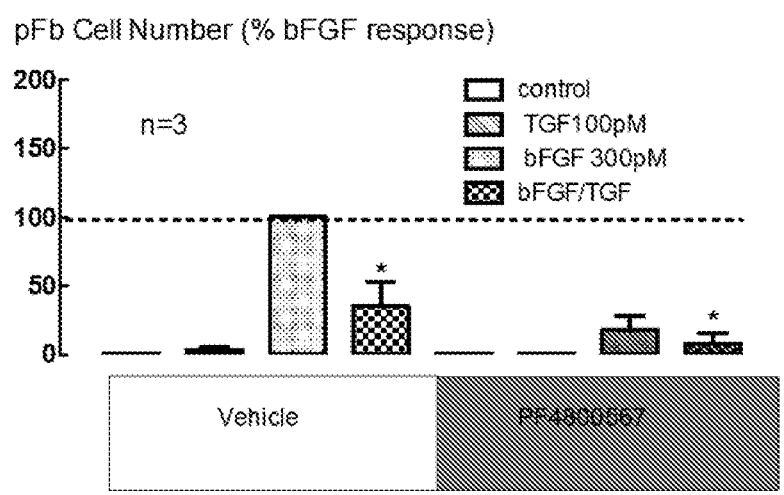
*P<0.05, cf bFGF Figure 11A
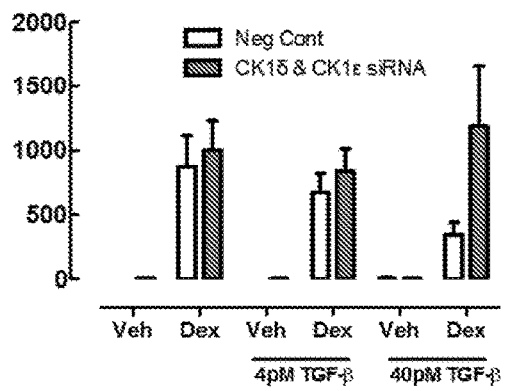
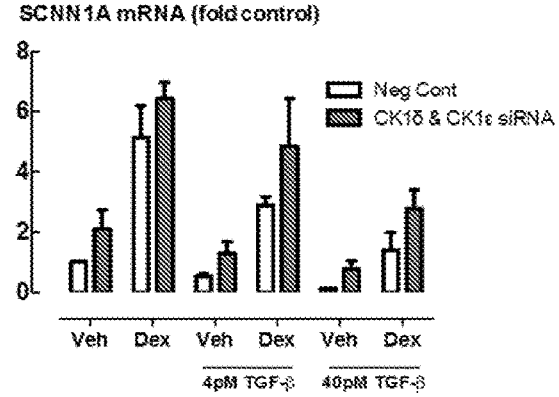
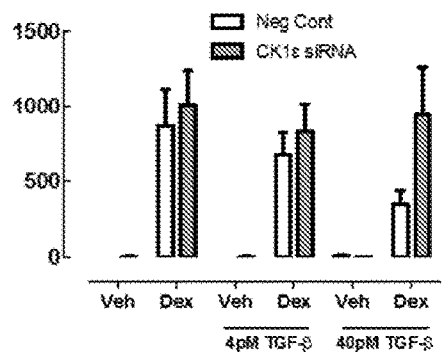
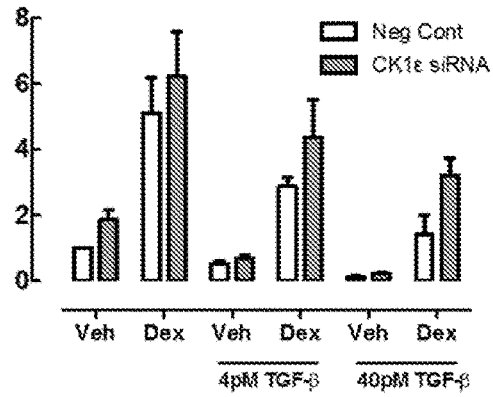
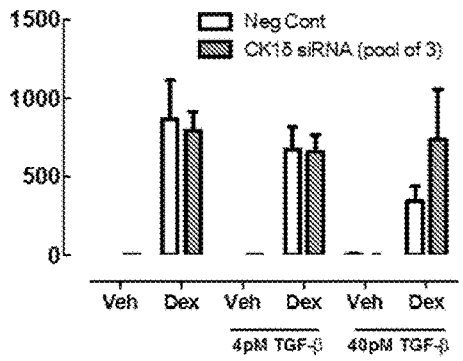
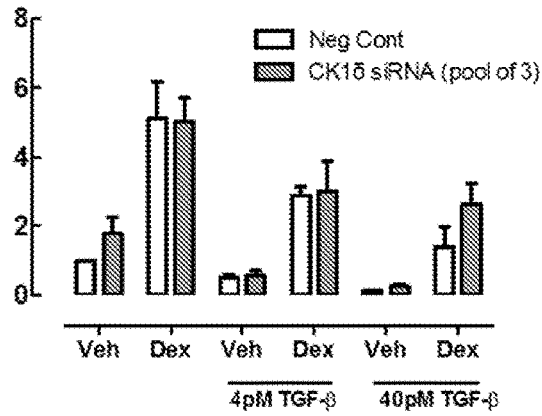

Figure 11B
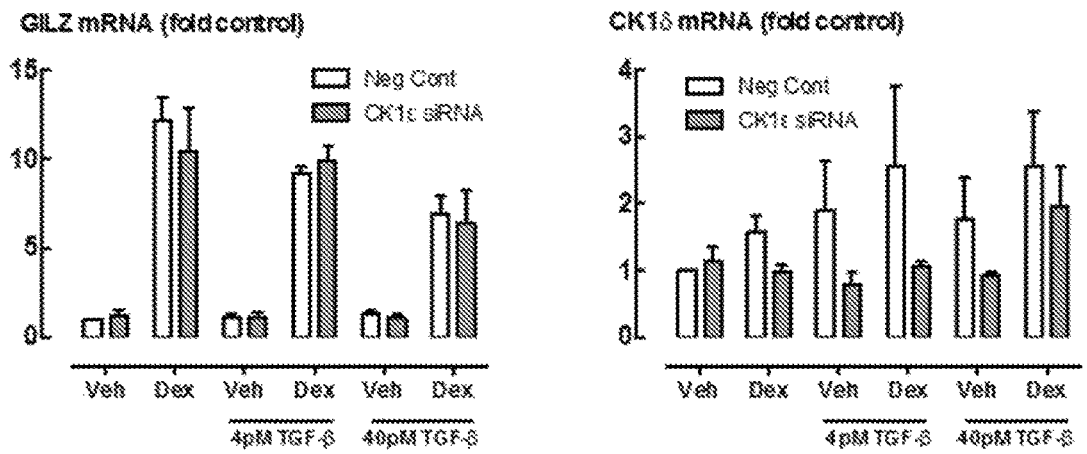
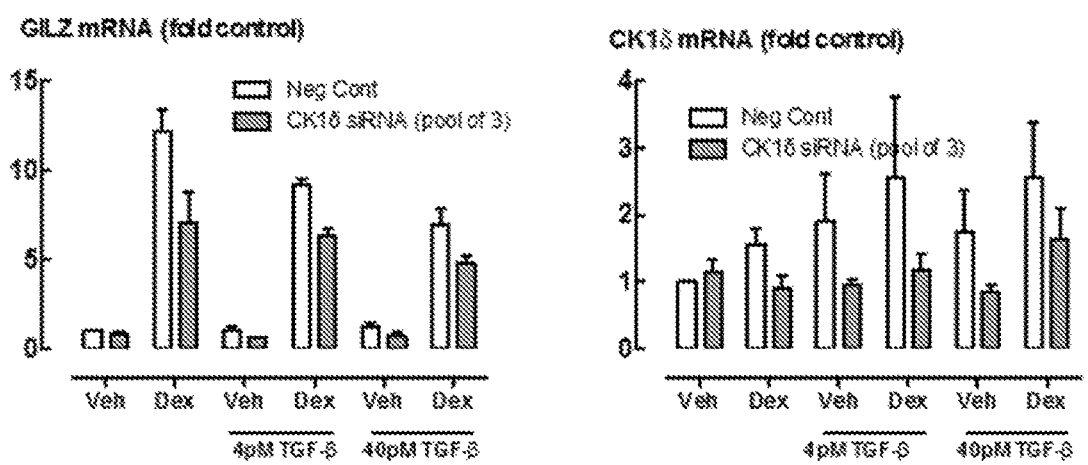
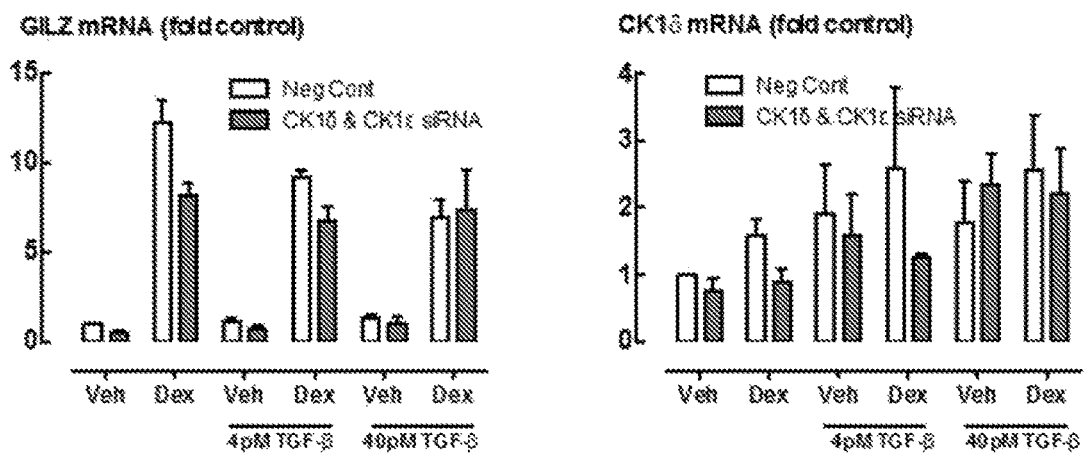

Figure 11C
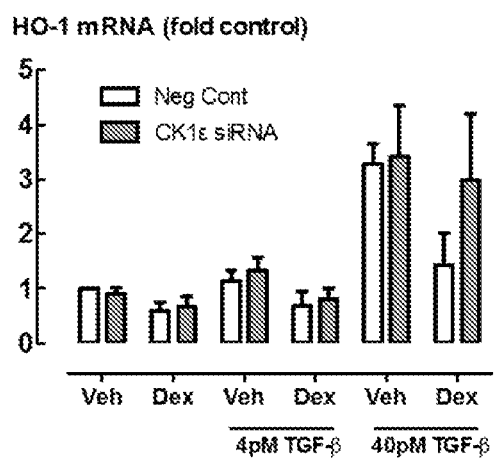
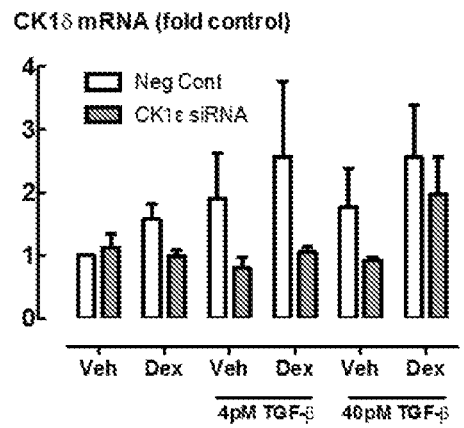
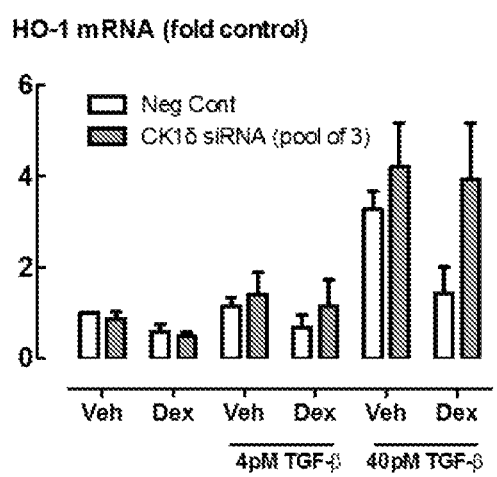
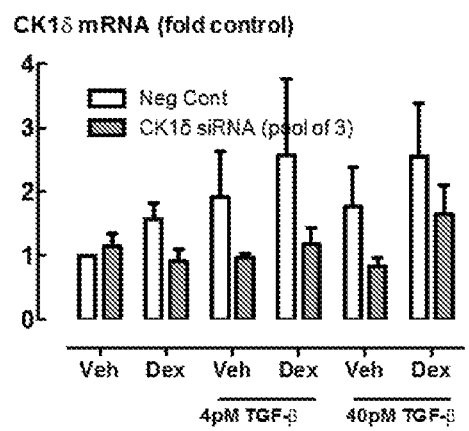
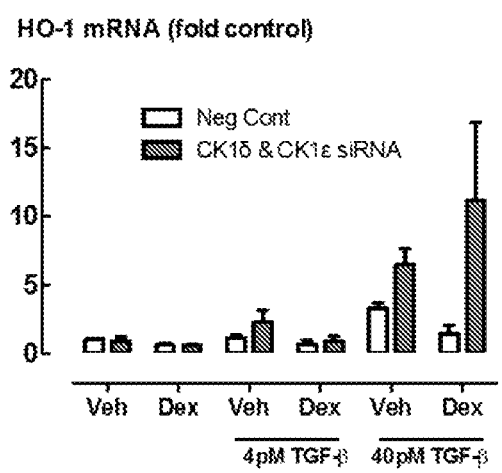
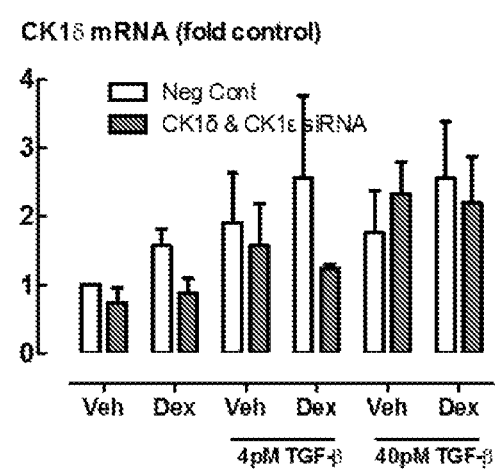

Figure 11D
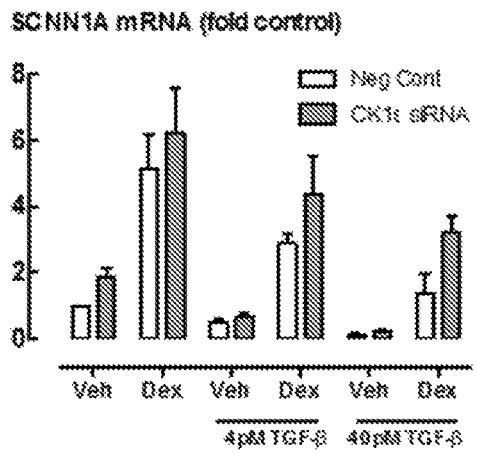
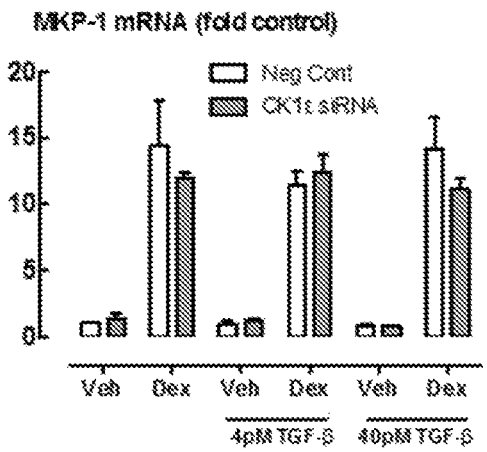
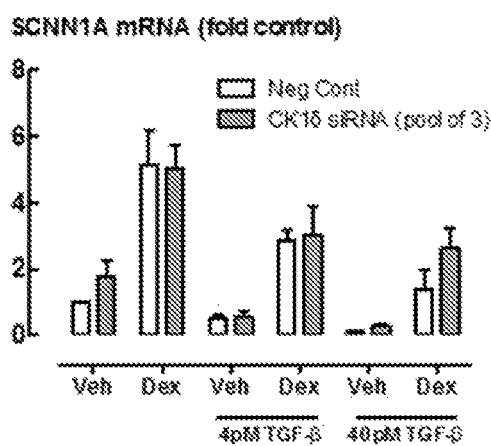
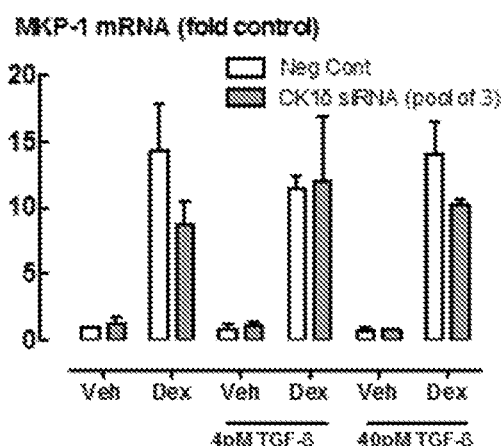
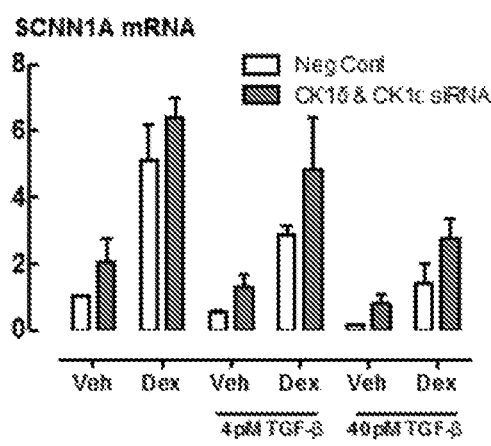
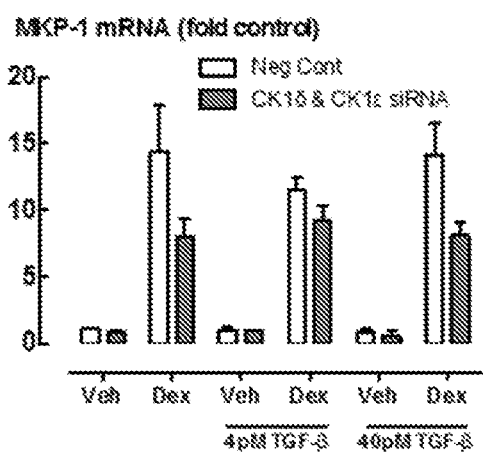

Figure 23
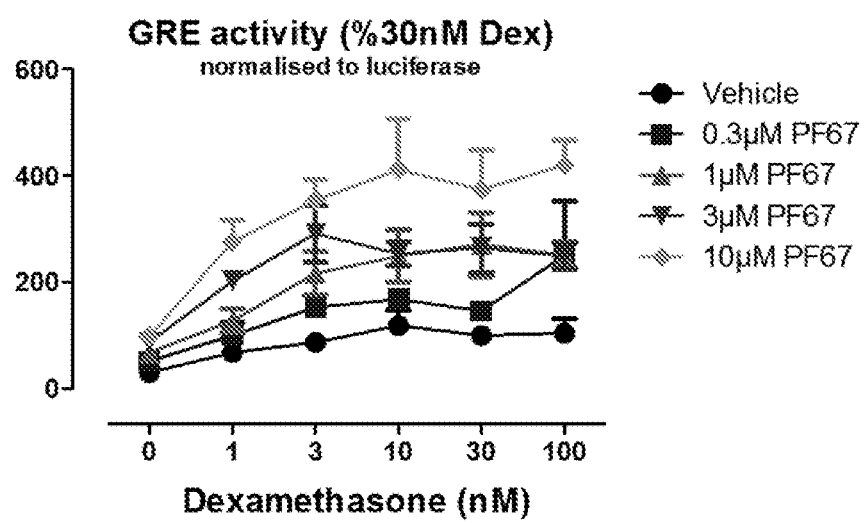
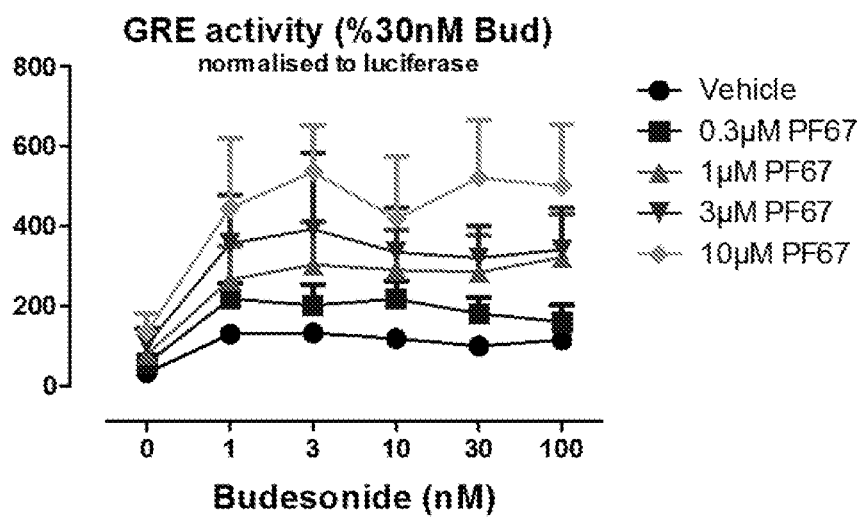

Figure 26
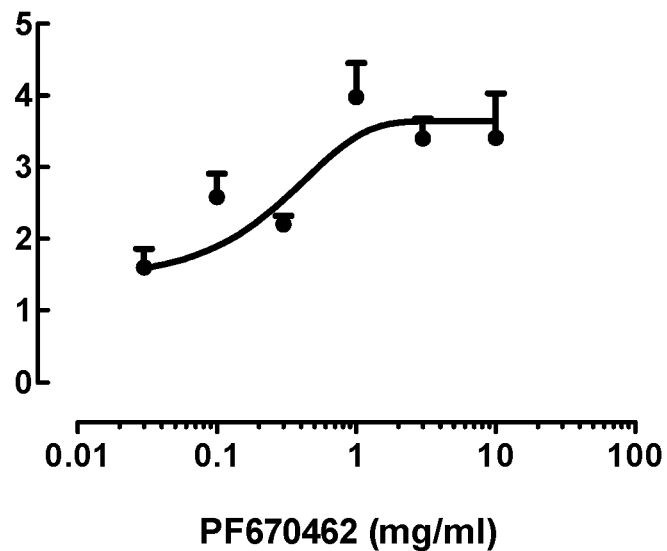
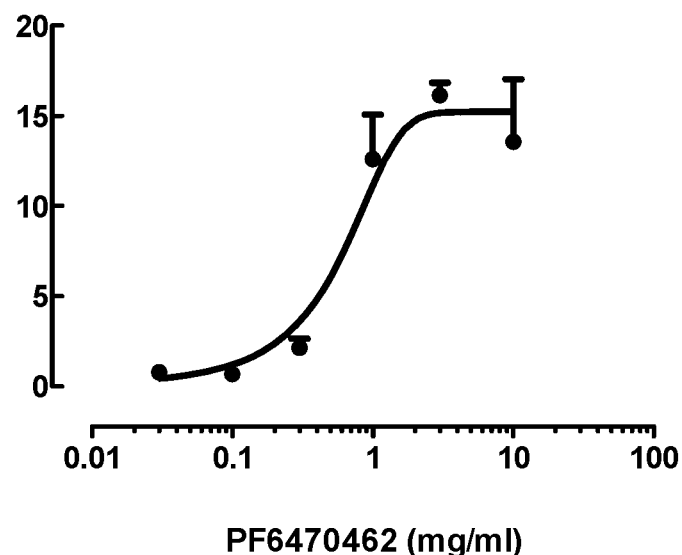

TREATMENT OF RESPIRATORY DISEASES

CROSS-REFERENCE TO RELATED APPLICATION

This application is a continuation of U.S. application Ser. No. 16/917,581, filed on Jun. 30, 2020, which is a continuation of U.S. application Ser. No. 15/559,360, filed on Sep. 18, 2017, now issued as U.S. Pat. No. 10,722,513, which is a § 371 national phase of International Application No. PCT/AU2016/050209, filed on Mar. 23, 2016, which claims priority from Australian provisional application no. 2015901032, filed on Mar. 23, 2015, the entire contents of which are incorporated herein by reference.

FIELD OF THE INVENTION

The present invention relates to compositions, methods and kits for the treatment of respiratory disease. In particular, the compositions, methods and kits are particularly useful, but not limited to, the treatment or prevention of exacerbations of respiratory disease, such as asthma and chronic obstructive pulmonary disease.

BACKGROUND OF THE INVENTION

Respiratory diseases encompass pathological conditions affecting the organs and tissues that make gas exchange possible in higher organisms. One such type of respiratory disease is asthma. Asthma is a common disease causing lost productivity and quality of life and consuming large amounts of health care costs. Mild to moderate asthma is usually well-controlled with inhaled glucocorticoids (ICS) in combination with long-acting β2-adrenoceptor agonists (LABA), so-called combination therapy. However, in patients with severe disease there are episodes of loss of asthma control. The majority of exacerbations of asthma (and of COPD) are due to viral infection of the lower respiratory tract, with rhinovirus (RV), respiratory syncytial virus (RSV) and influenza virus (InfV) being most commonly detected. The occurrence of exacerbations in patients who are taking combination therapy defines the exacerbations as resistant to treatment with glucocorticoids. This resistance can be viewed as an insensitivity of the viral inflammation to treatment by ICS/LABA, or more specifically that acute viral infection turns off some of the beneficial effects of glucocorticoid (GC). This acute GC-resistant exacerbation may be viewed as additional to an underlying state of the structural and inflammatory cells of the airways. In patients with severe obstructive disease, lung function does not normalize, even in the absence of respiratory tract infection and with compliance when treated with ICS/LABA. Thus, there is also a GC resistance in these chronic respiratory diseases that is not necessarily related to viral infection.

The prevalence of severe steroid resistant asthma is estimated to comprise 5% of all asthmatics. Given the high prevalence of asthma (~10%), there are approximately 125,000 Australians who are unable to achieve normal lung function when fully compliant with best-practice therapy, or who need oral steroids to maintain control. These patients are at increased risk of more severe exacerbations/death from asthma, have lower quality of life, higher frequency of hospital admissions and impact on the health care resources. Some patients with moderate and severe asthma, especially those who smoke, have unexpectedly limited responses to ICS.

There is a need for new and/or improved treatments or preventatives for respiratory diseases, particularly in patients who have experienced, or who are experiencing, resistance to treatment with a glucocorticoid.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

The present invention provides a method of treating or preventing a respiratory disease in a subject in need thereof, the method comprising administering to the subject a therapeutically effective amount of an inhibitor of casein kinase 1, thereby treating or preventing a respiratory disease in a subject.

The invention also provides a method of alleviating or ameliorating a symptom of a respiratory disease in a subject in need thereof, the method comprising administering to the subject in need thereof a therapeutically effective amount of an inhibitor of casein kinase 1, thereby alleviating or ameliorating a symptom of a respiratory disease in the subject.

The invention also provides use of an inhibitor of casein kinase 1 in the manufacture of a medicament for the treatment or prevention of a respiratory disease in a subject in need thereof.

The present invention provides a method for the treatment or prevention of a respiratory disease in a subject comprising the steps of administering to the subject in need thereof a therapeutically effective amount of an inhibitor of casein kinase 1, thereby treating or preventing a respiratory disease in the subject, wherein the subject has a viral respiratory tract infection or airway inflammation associated with or caused by an allergen. Typically, the viral infection is of rhinovirus (RV), respiratory syncytial virus (RSV) or influenza virus (InfV). The allergen may be a house dust mite allergen. In one embodiment, the subject is, at least partially, resistant to treatment involving a glucocorticoid.

The present invention provides a method for the treatment or prevention of an exacerbation of a respiratory disease in a subject comprising the steps of administering to the subject in need thereof a therapeutically effective amount of an inhibitor of casein kinase 1, thereby treating or preventing an exacerbation of a respiratory disease in the subject. The invention has particular application to a subject having a viral respiratory tract infection or airway inflammation associated with or caused by an allergen. Typically, the viral infection is of rhinovirus (RV), respiratory syncytial virus (RSV) or influenza virus (InfV). The respiratory disease may be one associated with an allergen, such as a house dust mite allergen. In one embodiment, the subject is, at least partially, resistant to treatment involving a glucocorticoid.

The present invention provides a method for the treatment or prevention of an exacerbation of a respiratory disease in a subject comprising the steps of identifying a subject having a respiratory disease, wherein the subject is, at least partially, resistant to treatment involving a glucocorticoid; and administering to the subject in need thereof a therapeutically effective amount of an inhibitor of casein kinase 1, thereby treating or preventing an exacerbation of a respiratory disease in the subject. The invention has particular application to a subject having a viral respiratory tract infection. Typically, the viral infection is of rhinovirus (RV), respiratory syncytial virus (RSV) or influenza virus (InfV). The respiratory disease may be one associated with an allergen, such as a house dust mite allergen.

The present invention provides a method for the treatment of a severe obstructive disease comprising the steps of
identifying a subject having severe obstructive disease; and
administering to the subject in need thereof a therapeutically effective amount of an inhibitor of casein kinase 1,
thereby treating severe obstructive disease.

The present invention provides a method for the treatment or prevention of exacerbations of asthma or chronic obstructive pulmonary disease comprising the steps of
identifying a subject having asthma or chronic obstructive pulmonary disease; and
administering to the subject in need thereof a therapeutically effective amount of an inhibitor of casein kinase 1,
thereby treating or preventing exacerbations of asthma or chronic obstructive pulmonary disease. Preferably, the subject is resistant to treatment involving a glucocorticoid. Preferably the glucocorticoid is an agonist, partial agonist or allosteric modulator of a glucocorticoid receptor. Preferably, the glucocorticoid is an inhaled glucocorticoid. Even more preferably, the glucocorticoid is budesonide, ciclosenide, mometasone or any other glucocorticoid described herein. The invention has particular application to a subject having a viral respiratory tract infection.

The present invention a method for the treatment of a severe obstructive disease comprising the steps of
identifying a subject having severe obstructive disease; and
administering to the subject in need thereof a therapeutically effective amount of an inhibitor of casein kinase 1,
thereby treating severe obstructive disease.

The present invention provides a method for the treatment or prevention of a respiratory disease, the method comprising the step of applying a composition to the site for treatment or prevention, wherein the composition comprises, consists essentially of or consists of an inhibitor of casein kinase 1 and a pharmaceutically acceptable diluent, excipient or carrier.

In any method or use of the invention described herein, an inhibitor of casein kinase 1 may be administered directly to the site of respiratory disease. The inhibitor of casein kinase 1 may be formulated for oral administration. Preferably, formulated for administration by inhalation. Typically, inhibitor of casein kinase 1 is formulated as a dry powder suitable for use in a dry powder inhaler device.

In any method or use of the invention described herein, there further comprises the step of administering one or more glucocorticoids. Preferably the glucocorticoid is an agonist, partial agonist or allosteric modulator of a glucocorticoid receptor. Preferably, the glucocorticoid is an inhalable glucocorticoid. Even more preferably, the glucocorticoid is budesonide, ciclosenide, mometasone or any other glucocorticoid described herein.

In any method or use of the invention described herein, the inhibitor of casein kinase 1 may be administered simultaneously or sequentially with one or more glucocorticoids. The inhibitor of casein kinase 1 may be administered prior to one or more glucocorticoids, alternatively the inhibitor may be administered after one or more glucocorticoids.

The invention provides a pharmaceutical composition for treating or preventing a respiratory disease comprising an inhibitor of casein kinase 1 and a pharmaceutically acceptable diluent, excipient or carrier. In one embodiment, the only active ingredient present in the composition is an inhibitor of casein kinase 1.

The invention provides a pharmaceutical composition for treating or preventing a respiratory disease comprising as an active ingredient an inhibitor of casein kinase 1 and a pharmaceutically acceptable diluent, excipient or carrier. In one embodiment, the only active ingredient present in the composition is an inhibitor of casein kinase 1.

The invention provides a pharmaceutical composition for treating or preventing a respiratory disease comprising as a main ingredient an inhibitor of casein kinase 1 and a pharmaceutically acceptable diluent, excipient or carrier. In one embodiment, the only active ingredient present in the composition is an inhibitor of casein kinase 1.

The invention also provides any pharmaceutical composition described herein further comprising one or more glucocorticoids. Preferably the glucocorticoid is an agonist, partial agonist or allosteric modulator of a glucocorticoid receptor. Preferably, the glucocorticoid is an inhalable glucocorticoid. Even more preferably, the glucocorticoid is budesonide, ciclosenide, mometasone or any other glucocorticoid described herein.

The invention also provides any pharmaceutical composition described herein, further comprising one or more bronchodilators.

The invention also provides any pharmaceutical composition described herein, further comprising (a) a steroidal or non-steroidal glucocorticoid receptor agonist or partial agonist, and/or (b) any long or ultra-long acting selective β2-adrenoceptor agonist.

The invention also provides any pharmaceutical composition described herein, further comprising (a) a short-acting β2-adrenoceptor agonist, partial agonist or positive allosteric modulator of the β2-adrenoceptor, and/or (b) another bronchodilator such as a muscarinic receptor antagonist, long-acting muscarinic receptor antagonist, and ultra-long acting muscarinic receptor antagonist, or inverse agonist, partial agonist or negative allosteric modulator of the muscarinic receptor. Exemplary β2-adrenoceptor agonists include indacaterol, vilanterol and olodaterol.

The invention also provides any pharmaceutical composition described herein, further comprising an inhibitor of SRC(Proto-oncogene tyrosine-protein kinase Src) kinase and/or an inhibitor of Phosphatidylinositol-4,5-bisphosphate 3-kinase (PI3k) delta.

The invention also provides any pharmaceutical composition described herein, further comprising a histamine H1, H3 and/or H4 antagonist.

Any pharmaceutical composition of the present invention may be formulated for oral administration. Preferably, formulated for administration by inhalation. Typically, the composition may be formulated as a dry powder suitable for use in a dry powder inhaler device.

Any pharmaceutical composition that includes an inhibitor of casein kinase 1 and a further active ingredient may be administered in a single inhaler. For example, the further active ingredient may be a bronchodilator, agonist and/or antagonist as described above.

The invention also provides an inhibitor of casein kinase 1 for use in the treatment of a respiratory disease.

The invention also provides a pharmaceutical composition comprising an inhibitor of casein kinase 1 and a pharmaceutically acceptable diluent, excipient or carrier for use in the treatment of a respiratory disease.

In any aspect of the invention, the inhibitor of casein kinase 1 inhibits the activity of the casein kinase epsilon isoform or the casein kinase delta isoform, more preferably the compound inhibits the activity of both casein kinase isoforms epsilon and delta. PF670462 is an example of an inhibitor of casein kinase 15 (delta) and E (epsilon).

In any aspect of the invention, the inhibitor of casein kinase 1 is selected from the group consisting of PF-670462, PF-4800567, PF-5006739 and D4476, or pharmaceutically acceptable salt, polymorph or prodrug thereof.

The present invention provides a method of treating or preventing a respiratory disease in a subject in need thereof, the method comprising administering to the subject a therapeutically effective amount of an inhibitor of ALK5, thereby treating or preventing a respiratory disease in a subject, wherein the inhibitor is administered directly to the airway and/or lungs.

The invention also provides use of an inhibitor of ALK5 in the manufacture of a medicament for the treatment or prevention of a respiratory disease in a subject in need thereof, wherein the inhibitor is administered directly to the airway and/or lungs.

The present invention provides a method for the treatment or prevention of an exacerbation of a respiratory disease in a subject comprising the steps of
identifying a subject having a respiratory disease, wherein the subject is, at least partially, resistant to treatment involving a glucocorticoid; and
administering to the subject in need thereof a therapeutically effective amount of an inhibitor of ALK5,
thereby treating or preventing an exacerbation of a respiratory disease in the subject, wherein the inhibitor is administered directly to the airway and/or lungs. The invention has particular application to a subject having a viral respiratory tract infection. Typically, the viral infection is of rhinovirus (RV), respiratory syncytial virus (RSV) or influenza virus (InfV).

The present invention provides a method for the treatment of a severe obstructive disease comprising the steps of
identifying a subject having severe obstructive disease; and
administering to the subject in need thereof a therapeutically effective amount of an inhibitor of ALK5,
thereby treating severe obstructive disease, wherein the inhibitor is administered directly to the airway and/or lungs.

The present invention provides a method for the treatment or prevention of exacerbations of asthma or chronic obstructive pulmonary disease comprising the steps of
identifying a subject having asthma or chronic obstructive pulmonary disease; and
administering to the subject in need thereof a therapeutically effective amount of an inhibitor of ALK5,
thereby treating or preventing exacerbations of asthma or chronic obstructive pulmonary disease, wherein the inhibitor is administered directly to the airway and/or lungs. Preferably the glucocorticoid is an agonist, partial agonist or allosteric modulator of a glucocorticoid receptor. Preferably, the glucocorticoid is an inhaled glucocorticoid. Even more preferably, the glucocorticoid is budesonide or any other glucocorticoid described herein. The invention has particular application to a subject having a viral respiratory tract infection.

In any aspect of the invention, the inhibitor of ALK5 is selected from the group consisting of SB431542, D4476 and GW788388, or pharmaceutically acceptable salt, polymorph or prodrug thereof.

The present invention provides a method of treating or preventing a condition of the airway or lung involving fibrosis in a subject in need thereof, the method comprising administering to the subject a therapeutically effective amount of an inhibitor of casein kinase 1, thereby treating or preventing a condition of the airway or lung involving fibrosis in a subject.

The invention also provides a method of alleviating or ameliorating a symptom of a condition of the airway or lung involving fibrosis in a subject in need thereof, the method comprising administering to the subject in need thereof a therapeutically effective amount of an inhibitor of casein kinase 1, thereby alleviating or ameliorating a symptom of a condition of the airway or lung involving fibrosis in the subject.

The invention also provides use of an inhibitor of casein kinase 1 in the manufacture of a medicament for the treatment or prevention of a condition of the airway or lung involving fibrosis in a subject in need thereof.

The present invention provides a method for the treatment or prevention of a condition of the airway or lung involving fibrosis in a subject comprising the steps of
identifying a subject having a condition of the airway or lung involving fibrosis; and
administering to the subject in need thereof a therapeutically effective amount of an inhibitor of casein kinase 1,
thereby treating or preventing a condition of the airway or lung involving fibrosis in the subject.

The present invention provides a method of treating or preventing a condition of the airway or lung involving fibrosis in a subject in need thereof, the method comprising administering to the subject a therapeutically effective amount of an inhibitor of ALK5, thereby treating or preventing a condition of the airway or lung involving fibrosis in a subject, wherein the inhibitor is administered directly to the airway and/or lungs.

The invention also provides a method of alleviating or ameliorating a symptom of a condition of the airway or lung involving fibrosis in a subject in need thereof, the method comprising administering to the subject in need thereof a therapeutically effective amount of an inhibitor of ALK5, thereby alleviating or ameliorating a symptom of a condition of the airway or lung involving fibrosis in the subject, wherein the inhibitor is administered directly to the airway and/or lungs.

The invention also provides use of an inhibitor of ALK5 in the manufacture of a medicament for the treatment or prevention of a condition of the airway or lung involving fibrosis in a subject in need thereof, wherein the inhibitor is administered directly to the airway and/or lungs.

The present invention provides a method for the treatment or prevention of a condition of the airway or lung involving fibrosis in a subject comprising the steps of
identifying a subject having a condition of the airway or lung involving fibrosis; and
administering to the subject in need thereof a therapeutically effective amount of an inhibitor of ALK5,
thereby treating or preventing a condition of the airway or lung involving fibrosis in the subject, wherein the inhibitor is administered directly to the airway and/or lungs.

For any aspect of the invention, the administration to the airway and the lungs is via any route that allows an inhibitor of casein kinase 1 or inhibitor of ALK5 to contact the airway, lung or a part thereof. For example, an inhibitor of casein kinase 1 or inhibitor of ALK5 may be administered via any route such that there is improvement in a symptom of the disease or condition to be treated or prevented. Preferably, the route of administration allows exposure to the respiratory tract or lung parenchyma such as alveolar tissue with respiratory bronchioles, alveolar ducts and terminal bronchioles. Preferably, an inhibitor of casein kinase 1 or inhibitor of ALK5 is formulated for inhalation or oral administration.

In any method or use herein for the treatment or prevention of a condition of the airway or lung involving fibrosis, the method or use may further comprise the administration of one or more glucocorticoids. Preferably the glucocorticoid is an agonist, partial agonist or allosteric modulator of a glucocorticoid receptor. Preferably, the glucocorticoid is an inhaled glucocorticoid. Even more preferably, the glucocorticoid is budesonide, ciclosenide, mometasone or any other glucocorticoid described herein. The inhibitor of casein kinase 1 may be administered simultaneously or sequentially with one or more glucocorticoids. The inhibitor of casein kinase 1 may be administered prior to one or more glucocorticoids, alternatively the inhibitor may be administered after one or more glucocorticoids.

In any method or use herein for the treatment or prevention of a condition of the airway or lung involving fibrosis, the method or use may further comprise administering an anti-fibrotic compound, for example nintedanib, tranilast and pirfenidone.

Any pharmaceutical composition described herein for the treatment or prevention of a condition of the airway or lung involving fibrosis may further comprise administering an anti-fibrotic compound, for example nintedanibm tranilast and pirfenidone.

The invention provides a kit or article of manufacture comprising any an inhibitor of casein kinase 1 or inhibitor of ALK5, and/or a pharmaceutical composition described herein.

As used herein, except where the context requires otherwise, the term 'comprise' and variations of the term, such as 'comprising', 'comprises' and 'comprised', are not intended to exclude further additives, components, integers or steps.

Further aspects of the present invention and further embodiments of the aspects described in the preceding paragraphs will become apparent from the following description, given by way of example and with reference to the accompanying drawings.

BRIEF DESCRIPTION OF THE DRAWINGS

FIG. 6A concentrations of SB431542 and PF670462 are 1 µM and 10 µM respectively. FIG. 6B concentrations of SB431542 and PF670462 are both 3 µM. *P<0.05, Bonferroni's paired post hoc paired t-test.

FIG. 8B shows the expression of genes that are controlled by dex to varying degrees during RSV infection. FIG. 8C shows interferon expression in bronchoalveolar lavage cells and lung tissue. Each of the interferons declines with Dex and is restored by combined treatment with PF670462.

FIG. 10 Interaction between TGFβ and bFGF in human lung fibroblasts. SB431542 or PF4800567 was added 30 min before TGFβ which was added simultaneously with bFGF and incubation continued for 48 h at which time viable cell number was determined.

FIGS. 11A-11D show data from a series of experiments using siRNA against either CK1δ (delta) or CK1ε (epsilon) or their combined effects.

FIG. 15A shows the expression of collagen 1A at baseline (control) and in response to a 24 hour incubation with TGFβ 40 µM. The data shown is for parenchymal lung fibroblasts from both patients with the pulmonary fibrotic disease, idiopathic pulmonary fibrosis (IPF) and those derived samples of non-IPF donors. FIG. 15B shows the results of a similar experiment as for FIG. 15A except that in this case the fibroblasts are cultured as a suspended spheroid, rather than in 2D monolayer culture. FIG. 15C shows the results of measurement of TGFβ-induced expression of CTGF in the same experiment as reported in FIG. 15A.

FIG. 23 shows the effects of increasing concentrations of PF670462 on budesonide and dexamethasone (1-100 nM) mediated activation of a GRE reporter construct transiently expressed in BEAS 2B cells.

FIG. 26 shows the dose-related increase in the lung expression of ZBTB16 and GILZ in mice exposed to an aerosol of PF670462 (0.03-10 mg/ml, 7 min).

Figure 1:
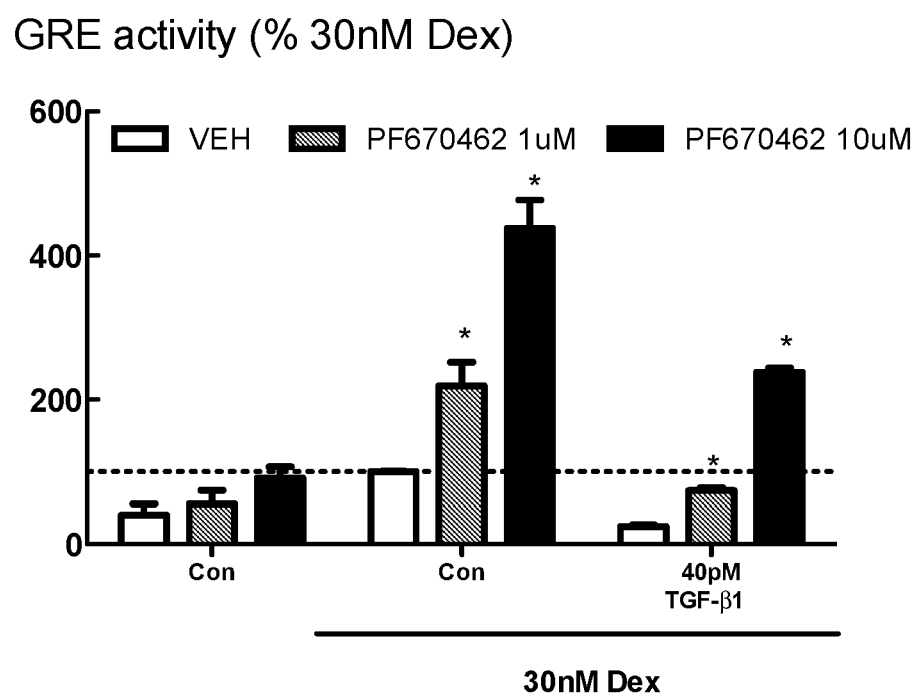
FIG. 1 BEAS-2B cells grown in cortisol deficient medium for 24 hours were pre-treated with either PF670462 at 1 or 10 µM for 30 min before exposure to TGFβ1 for 24 hours, prior to stimulation by Dexamethasone (30 nM), a concentration previously established to optimally activate glucocorticoid response element (GRE) activity. PF670462 concentration-dependently attenuated the profound TGFβ1-induced suppression of the GRE activity stimulated by Dex (30 nM). Data are presented as the means and SEM of 3 independent experiments. *P<0.05, cf corresponding Dex 30 nM response.

Unless otherwise stated, any statistical significance shown in the Figures and referred to here is *$P<0.05$.

DETAILED DESCRIPTION OF THE EMBODIMENTS

It will be understood that the invention disclosed and defined in this specification extends to all alternative combinations of two or more of the individual features mentioned or evident from the text or drawings. All of these different combinations constitute various alternative aspects of the invention.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described. It will be understood that the invention disclosed and defined in this specification extends to all alternative combinations of two or more of the individual features mentioned or evident from the text or drawings. All of these different combinations constitute various alternative aspects of the invention.

All of the patents and publications referred to herein are incorporated by reference in their entirety.

For purposes of interpreting this specification, terms used in the singular will also include the plural and vice versa.

The present invention has unexpected advantages including that the methods and compositions described herein enhance the activity of glucocorticoids including those currently being used to control various respiratory disease including asthma and COPD. This may be particularly useful in patient populations where limitation of steroid use is desirable, such as in children. A further advantage in the treatment of exacerbations of airway disease is the modulation of interferon gene expression in infection, which suggests an indirect action to promote innate host defence responses.

Further, the invention also has the unexpected advantages that the methods and compositions described herein inhibit or oppose the negative effects of glucocorticoids in certain circumstances. One such non-limiting example, is the inhibition of the inhibitory effect of glucocorticoids on interferon expression.

Without being bound by any theory or mode of action, it is believed the compounds used in the invention are having beneficial TGFβ modulatory actions through selective inhibition of pathways downstream of the TGFβ receptor/activin-like kinase 5 (ALK5). This reduces the risk of causing known adverse effects through global inhibition of TGFβ.

As used herein, a 'casein kinase 1 inhibitor' or 'inhibitor of casein kinase 1' is any compound that inhibits the activity of casein kinase 1. In a preferred form the compound is a molecule that inhibits the serine/threonine kinase activity of casein kinase 1 for example by competing with the enzyme substrate or phosphate group. In a preferred form the compound is a molecule that inhibits the serine/threonine kinase activity of casein kinase 1 by disrupting the signalasome or any other protein-protein interaction required for serine/threonine kinase activity of casein kinase 1. Preferably, the compound inhibits the activity of the casein kinase epsilon isoform, more preferably the compound inhibits the activity of both casein kinase isoforms epsilon and delta. The inhibitor may also have some inhibitory activity against other casein kinases, e.g. casein kinase 2. Preferably, the inhibitor of casein kinase 1 is a substance that limits the activity of casein kinase 1 to 10% or less in comparison with control. Control is a solvent, in which the inhibitor is tested, used at the same quantity, however, without the inhibitor. The inhibition activity towards casein kinase 1 can be determined for example using in vitro kinase assay according to Bain et al. Biochem. J. (2007) 408,297-315 or other method described herein. In preferred forms, the inhibitor may be a small molecule chemical compound or interfering RNA (e.g. siRNA).

As used herein, reference to casein kinase 1 inhibitor or inhibitor of casein kinase 1 also includes a pharmaceutically acceptable salt, polymorph or prodrug thereof.

Inhibitors of casein kinase 1 are known in the art. For example, casein kinase 1 inhibitors described in Bain, J et al. Biochem J (2007), 408, 291-315, Long, A. M, et al J. Med. Chem. (2012) 55, 10307-10311, Walton, K. M, et al. J Pharmacol Exp Ther (2009) 330 430-439, Rena, et al. EMBO Reports, (2004), 60-65, Huang, H., ei al ACS Med Chem Lett (2012) 3, 1059-1064, Mente, S., et al. J. Med. Chem. (2013), 56, 6819-6828, Peifer, C., et al. J. Med. Chem. (2009) 52, 7618-7630, Chen, Z., et al. Cell Mol Life Sci (2013), 70, 2985-2998, Wager, T. T. et al ACS Chemical Neuroscience (2014) 5, 1253-1265, WO2011/127202, WO2014/023271, WO2012/080727, WO2011051858 and WO2014/100533 may be useful in this invention.

A compound useful in this invention may, for example, as provided in WO2012/080727, include a compound of formula I or a pharmaceutically acceptable salt, polymorph, prodrug or solvate thereof:

wherein

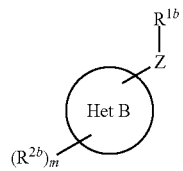

Formula I

"Het B" represents a 5 membered heterocyclic ring system containing 1 to 3 heteroatoms selected from O, N or S, wherein said ring system is fused to one or more (e.g. 1-3) further rings to form a polycyclic ring system comprising up to 4 rings;

Z represents a bond, —C(R$^{7b}$)(R$^{8b}$)—, (CH$_2$)$_2$, —O—, —S—, —CH$_2$O—, —(CH$_2$)$_2$—O—, NR$^{6b}$, —N(R$^{6b}$)—C(R$^{7b}$)(R$^{8b}$)—, —N(R$^{6b}$)—(CH$_2$)$_2$—, —N(R$^{6b}$)—(CH$_2$)$_3$—, —CH—N(R$^{6b}$)—(CH$_2$)$_2$—, —N(R$^{6b}$)—CO—, —CH$_2$—NHCO—(CH$_2$)$_2$—, —N(R$^{6b}$)—CO—CH$_2$—, =N—, —N(R$^{7b}$)—CH=, —C(H)(CN)—, —C(=N—NH—COC$_{1-6}$ alkyl)-, CH=C(R$^{6b}$)—CO—, =CH—, —N=CH—, —N=C(Me)-, —C(R$^{6b}$)=CH—, —NH—CO—C(=CH-heteroaryl)-, —C(=C(R$^{7b}$)(R$^{8b}$))—, —CH=CH—CO—N(R$^{6b}$)—, —CH=C(R$^{6b}$)—CO—NH—CH$_2$—, —CH=C(R$^{6b}$)—NH—CO—, CH=C(R$^{6b}$)—CO—O—CH$_2$—, —CS—S—CH$_2$—, —NH—CS—NH—, —NH—CS—NH—CH$_2$—, —NH—CS—NH—(CH$_2$)$_2$—, —CH$_2$—N(CSNH$_2$)—CH$_2$—, —S—C(R$^{5b}$)(R$^{6b}$)—, —S—(CH$_2$)$_2$—O—, —SO$_2$, —NH—SO$_2$—, —CH—NH—SO$_2$—, CO, —CH—CO—, —(CH$_2$)$_2$—CO—, —O—CH$_2$—CO—, —(CH$_2$)$_2$—CO—, COO, —COO—C(R$^{7b}$)CO—, —CH=C(R$^{5b}$)CONH—CH$_2$—, —CO—CH$_2$—N(R$^{6b}$)—CO—, —CO—CH$_2$—C(R$^{6b}$)—CH$_2$—CO—, —CO—CH$_2$—N(R$^{6b}$)—CH—, CO—NH—N=C(R$^{7b}$)—, —S—CH—CO—, —S—CH—CO—N(R$^{6b}$)—, —S—CH—CO—N(R$^{6b}$)—CH$_2$—, —SO$_2$—N(R$^{6b}$)—C(R$^{7b}$)(R$^{8b}$)—CONH—, —SO$_2$—N(R$^{6b}$)—CH(—CH$_2$-aryl)-CONH—CH$_2$—, —CH(—S—C$_{1-6}$ alkyl)-C(Me)(OH)—, —CH$_2$—C(R$^{6b}$)(OH)—, —C(OH)(CH(Me)(C$_{3-8}$ cycloalkyl))-CH$_2$—, —C(OH)(R$^{6b}$)—CH$_2$—, —CH(Me)-NH—CO—CH$_2$—, —CO—N(R$^{6b}$)—CH$_2$—, —C(H)(R$^{6b}$)—CO—N(R$^{5b}$)—CH$_2$—, —CO—N(R$^{6b}$)—CH$_2$—CH$_2$—, —CO—N(R$^{6b}$)—CH$_2$—CH$_2$—CO—NH—CH$_2$—, —CO—NH—C(—CONH$_2$)=CH—, —CO—NH—CH (CONH₂)—CH₂—, —CH₂—C(H)(Me)-CH₂—S—, —O—CH₂—CO—NH—, —CH₂—N(R⁶ᵇ)—CO—CH₂—O—, N(R⁶ᵇ)—CO—CH₂—O—, —C(H)(—CH₂-aryl)-, —C(H)(—CH₂-heteroaryl)-, —C(NH-aryl)=N—N=CH—, —C(NH-aryl)=N—N=CH—, —NH—CO—CH₂—N(R⁶ᵇ)—, —NH—N=C(-aryl)-, —NH—N=C(-aryl)-CO—, —NH—C(=N—CO—C₁₋₆ alkyl)-NH—(CH₂)₂—, —C(—NH-aryl)=N—N=CH—, —NH—C(—NH-aryl)=N—CONH—, C(=CH-aryl)-CONH—CH₂—, —CH=C(R⁶ᵇ)—CONH—, —CH(—CH₂-aryl)-NH—CO— or —CH(OH)—, wherein said aryl or heteroaryl groups of Z may be optionally substituted by one or more halogen, $C_{1-6}$ alkyl, $C_{1-6}$ alkoxy, $NO_2$ or hydroxyl groups;

$R^{5b}$ represents hydrogen, $C_{1-6}$ alkyl or cyano;

$R^{6b}$ represents hydrogen, $C_{1-6}$ alkyl, $C_{1-6}$ alkoxy, cyano, COOH, —COOC$_{1-6}$ alkyl, $C_{3-8}$ cycloalkyl, —CH₂—C$_{3-8}$ cycloalkyl, aryl, heteroaryl, —C$_{1-6}$ alkylene-aryl, —CO-aryl, —O—CO-heteroaryl, —CO-heteroaryl or —C(R⁷ᵇ)(R⁸ᵇ)-heteroaryl, wherein said aryl groups of $R^{6b}$ may be optionally substituted by one or more halogen or $C_{1-6}$ alkoxy groups;

$R^{7b}$ and $R^{8b}$ independently represent hydrogen or $C_{1-6}$ alkyl;

$R^{1b}$ represents aryl, $C_{3-8}$ cycloalkyl, monocyclic or bicyclic heterocyclyl or a monocyclic or bicyclic heteroaryl ring system, wherein $R^{1b}$ may be substituted by one or more (e.g. 1, 2 or 3) $R^{4b}$ groups;

$R^{4b}$ represents halogen, $C_{1-6}$ alkyl, $C_{1-6}$ alkenyl, $C_{1-6}$ alkynyl, $C_{3-5}$ cycloalkyl, haloC$_{1-6}$ alkyl, hydroxyl, $C_{1-6}$ alkoxy, —O—C$_{1-6}$ alkenyl, haloC$_{1-6}$ alkoxy, —COOH, —CO—C$_{1-6}$ alkyl, —COO—C$_{1-6}$ alkyl, —CONH₂, —CH₂—CONH₂—, —NH—C$_{1-6}$ alkyl, —NH—C$_{2-6}$ alkenyl, —NH—CO—C$_{1-6}$ alkyl, —CONH—C$_{1-6}$ alkyl, —O—CH₂—CO—NH—C$_{1-6}$ alkyl, —CH₂—CH₂—CO—NH—C$_{1-6}$ alkyl, —S—C$_{1-6}$ alkyl, —SO—C$_{1-6}$ alkyl, —SO₂—C$_{1-6}$ alkyl, —SO₂—NH₂, —SO₂—NH—C$_{1-6}$ alkyl, —S—CH₂—CO—C$_{2-6}$ alkenyl, —SO₂—OH, amino, cyano, NO₂—, =O, —CO—NH—(CH₂)₂)—OMe, —NH—C$_{3-5}$ cycloalkyl, —CH₂—CO—NH—C$_{3-5}$cycloalkyl, —CO-heterocyclyl, —CO-heteroaryl, —COO—(CH₂)₂-heterocyclyl, —CH₂-aryl, —OCH₂-aryl, —OCH₂-heteroaryl, —CH₂—O—CO-aryl, —O-aryl, —NH—CO-aryl, —NH—CO-heteroaryl, —NH—CO—CH₂-aryl, —NH-aryl, aryl or heteroaryl groups, wherein said aryl, heterocyclyl or heteroaryl groups of $R^{4b}$ may be optionally substituted by one or more halogen, $C_{1-6}$ alkyl, $C_{1-6}$ alkoxy, =S or hydroxyl groups and wherein said $C_{1-6}$ alkyl or $C_{2-6}$ alkenyl groups of $R^{4b}$ may be optionally substituted by one or more hydroxyl, amino, cyano, $C_{1-6}$ alkoxy, $CONH_2$ or —COO—C$_{1-6}$ alkyl groups;

m represents an integer from 0 to 3;

$R^{2b}$ represents halogen, haloC$_{1-6}$ alkyl, $C_{1-6}$ alkyl, $C_{3-8}$ cycloalkyl, hydroxyl, $C_{1-6}$ alkoxy, —SC$_{1-6}$ alkyl, —CH₂—S—C$_{1-6}$ alkyl, —S—C$_{2-6}$ alkynyl, amino, cyano, $NO_2$, =O, =S, —SO₂—C$_{1-6}$ alkyl, $CONH_2$, —CO—C$_{1-6}$ alkyl, —COO—C$_{1-6}$ alkyl, —NH—C$_{1-6}$ alkyl, —NH—CO—C$_{1-6}$ alkyl, —NH—CO—CH=CH—CHrN(Me)₂, $C_{1-6}$ alkyl, —CO—NH—C$_{1-6}$ alkyl, —CO—NH—CH(Me)-COOH, —S—CH₂—CON(Et)₂, —NH—(CH₂)₂—OH, —NH—(CH₂)₃—OH, —NH—CH(Et)-CH₂—OH, —CO—NH—(CH₂)₃—OH, —CH(CH₂OH)₂ or —S—CH₂—CO—NH—CO—NH—C$_{1-6}$ alkyl, wherein said $C_{1-6}$ alkyl groups of $R^{2b}$ may be optionally substituted by one or more cyano or hydroxyl groups.

Another compound useful in this invention may, for example, as provided in WO2011/051858, includes a compound or a pharmaceutically acceptable salt, polymorph prodrug or solvate thereof, having the structure of Formula II:

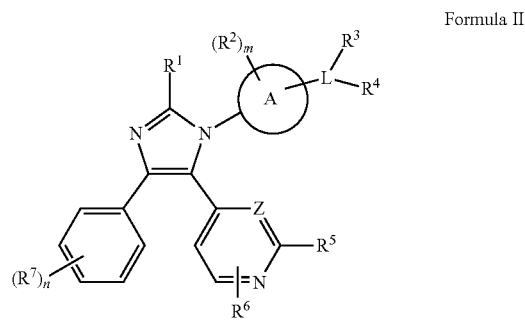

Formula II wherein A is a nitrogen-containing 4- to 7-membered heterocycloalkyl, or alternatively A can be directly fused to the ring to which it is attached through $R^1$;

L is $C_{1-3}$ alkyl;

$R^1$ is hydrogen, $C_{1-3}$ alkyl, or $C_{3-4}$ cycloalkyl;

each $R^2$ is independently $C_{1-3}$ alkyl, fluorine, hydroxyl, $C_{1-3}$ alkoxy, or cyano;

$R^3$ is hydrogen, $C_{1-3}$ alkyl, or $C_{3-4}$ cycloalkyl;

$R^4$ is a 5- to 10-membered heteroaryl with 1 to 3 heteroatoms, optionally substituted with 1 to 3 $R^7$ substituents;

$R^5$ is hydrogen or —N(R⁸)₂;

$R^6$ is hydrogen, halogen or $C_{1-3}$ alkyl;

each $R^7$ is independently halogen, —(CH₂)$_t$—F$_q$, $C_{1-3}$ alkyl, —CF₃, —(CH₂)$_t$—C$_{3-4}$ cycloalkyl, —(CH₂)$_t$—O—C$_{1-3}$ alkyl, —(CH₂)$_t$-cyano or —(CH₂)$_t$-hydroxy;

Z is N or CR⁹;

each $R^8$ is independently hydrogen or $C_{1-3}$ alkyl;

$R^9$ is hydrogen, $C_{1-3}$ alkyl, or halogen;

m is 0, 1 or 2;

n is 0, 1 or 2;

q is 1, 2, or 3;

t is 0, 1 or 2.

Another compound useful in this invention may, for example, as provided in WO2014/100533, include a compound of Formula III, including enantiomers, diastereomers, tautomers, pharmaceutically-acceptable salts, prodrugs, hydrates, or solvates thereof

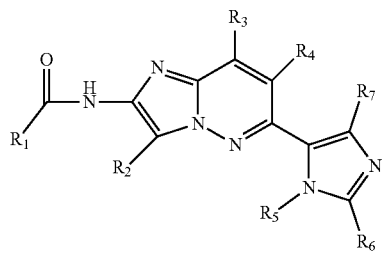

Formula III wherein:

$R_1$ is selected from NR$_a$R$_a$, $C_{1-4}$ alkyl optionally substituted with OH, CN, and aryl, $C_{2-4}$ alkenyl optionally substituted with OH, CN, and aryl, —(CR$_d$R$_d$)$_r$-carbocyclyl substituted with 0-5 R$_{11}$, and —(CR$_d$R$_d$)$_r$-heterocyclyl comprising carbon atoms and 1 to 3 heteroatoms selected from N, NR$_{12}$, O, S, and substituted with 0-5 R$_{11}$;

R₂ is selected from H, $C_{1-4}$ alkyl, F, Cl, Br, and CN;
R₃ is selected from H and $C_{1-4}$ alkyl;
R₄ is selected from H, $C_{1-4}$ alkyl, F, Cl, Br, and CN;
R₅ is selected from H, $C_{1-4}$ alkyl substituted with 0-4 $R_e$, —(CH₂)$_r$—$C_{3-6}$ carbocyclyl substituted with 0-4 $R_e$, and —(CH₂)$_r$-heterocyclyl comprising carbon atoms and 1 to 3 heteroatoms selected from N, NRs, O, S, and substituted with 0-4 $R_e$;
R₆ is selected from H, $C_{1-6}$ alkyl substituted with 0-3 $R_e$, and $C_{3-6}$ carbocyclyl substituted with 0-3 $R_e$; or
R₅ and R₆ together with the nitrogen atom and the adjacent carbon atom to which they are respectively attached form a heterocyclic ring substituted with 0-5 $R_9$;
R₇ is aryl substituted with 0-3 $R_e$;
R₈ is selected from H, $C_{1-4}$ alkyl substituted with 0-3 $R_e$, —(CH₂)$_r$OR$_b$, (CH₂)$_r$S(O)$_p$R$_c$, —(CH₂)$_r$C(=O)R$_b$, —(CH₂)$_r$NR$_a$R$_a$, —(CH₂)$_r$C(=O)NR$_a$R$_a$, —(CH₂)$_r$C(=O)(CH₂)$_r$NR$_a$R$_a$, —(CH₂)$_r$NR$_a$C(=O)R$_b$, —(CH₂)$_r$NR$_a$C(=O)OR$_b$, —(CH₂)$_r$OC(=O)NR$_a$R$_a$, —(CH₂)$_r$NR$_a$C(=O)NR$_a$R$_a$, —(CH₂)$_r$C(=O)OR$_b$, —(CH₂)$_r$S(O)₂NR$_a$R$_a$, —(CH₂)$_r$NR$_a$S(O)₂NR$_a$R$_a$, —(CH₂)$_r$NR$_a$S(O)₂R$_c$, (CH₂)$_r$—$C_{3-6}$ carbocyclyl substituted with 0-3 $R_e$, and —(CH₂)$_r$-heterocyclyl substituted with 0-3 $R_e$;
R₉ is selected from $C_{1-4}$ alkyl substituted with 0-3 $R_e$, —(CH₂)$_r$NR$_a$R$_a$, —(CH₂)$_r$C(=O)R$_b$, —(CH₂)$_r$C(=O)OR$_b$, —(CH₂)$_r$C(=O)NR$_a$R$_a$, S(O)$_p$R$_c$, (CH₂)$_r$—$C_{3-6}$ carbocyclyl substituted with 0-3 $R_e$, and —(CH₂)$_r$-heterocyclyl substituted with 0-3 $R_e$;
R₁₁, at each occurrence, is independently selected from H, F, Cl, Br, =O, CN, NO₂, —OR$_b$, —S(O)$_p$R$_c$, —C(=O)R$_b$, —(CR$_d$R$_d$)$_r$NR$_a$R$_a$, —(CR$_d$R$_d$)$_r$C(=O)NR$_a$R$_a$, —NR$_a$C(=O)R$_b$, —NR$_a$C(=O)OR$_b$, —OC(=O)NR$_a$R$_a$, —NR$_a$C(=O)NR$_a$R$_a$, —(CR$_d$R$_d$)$_r$C(=O)OR$_b$, —S(O)₂NR$_a$R$_a$, —NR$_a$S(O)₂NR$_a$R$_a$, —NR$_a$S(O)₂R$_c$, $C_{1-6}$ alkyl substituted with 0-5 $R_e$, —(CR$_d$R$_d$)$_r$—$C_{3-6}$ carbocyclyl substituted with 0-5 $R_e$, and —(CR$_d$R$_d$)$_r$-heterocyclyl substituted with 0-5 $R_e$;
R₁₂ is selected from H, —C(=O)R$_b$, $C_{1-6}$ alkyl substituted with 0-5 $R_e$, —(CH₂)$_r$—$C_{3-6}$ carbocyclyl substituted with 0-5 $R_e$, and —(CH₂)$_r$-heterocyclyl substituted with 0-5 $R_e$;
R$_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH₂)$_r$—$C_{3-10}$ carbocyclyl substituted with 0-5 $R_e$, and —(CH₂)$_r$-heterocyclyl substituted with 0-5 $R_e$; or R$_a$ and R$_a$ together with the nitrogen atom to which they are both attached form a heterocyclic ring substituted with 0-5 $R_e$;
R$_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH₂)$_r$—$C_{3-10}$ carbocyclyl substituted with 0-5 $R_e$, and —(CH₂)$_r$-heterocyclyl substituted with 0-5 $R_e$;
R$_c$, at each occurrence, is independently selected from $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $C_{3-6}$ carbocyclyl, and heterocyclyl;
R$_d$, at each occurrence, is independently selected from H and $C_{1-4}$ alkyl substituted with 0-5 $R_e$;
R$_e$, at each occurrence, is independently selected from $C_{1-6}$ alkyl substituted with 0-5 $R_f$, $C_{2-6}$ alkenyl, $C_{2-6}$ alkynyl, —(CH₂)$_r$—$C_{3-6}$ cycloalkyl, F, Cl, Br, CN, NO₂, =O, CO₂H, —(CH₂)$_r$OC$_{1-5}$ alkyl, —(CH₂)$_r$OR$_f$, S(O)$_p$R$_f$, S(O)$_p$NR$_f$R$_f$, and —(CH₂)$_r$NR$_f$R$_f$;
R$_f$, at each occurrence, is independently selected from H, $C_{1-5}$ alkyl, $C_{3-6}$ cycloalkyl, and phenyl, or R$_f$ and R$_f$ together with the nitrogen atom to which they are both attached form a heterocyclic ring optionally substituted with $C_{1-4}$ alkyl;

p, at each occurrence, is independently selected from zero, 1, and 2; and r, at each occurrence, is independently selected from zero, 1, 2, 3, and 4.

Preferably, the compound is selected from the group consisting of:

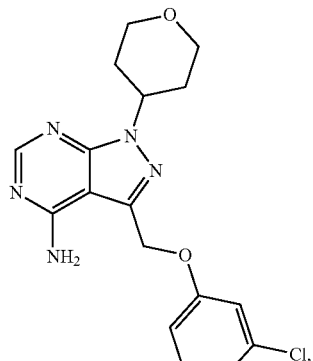

PF-4800567

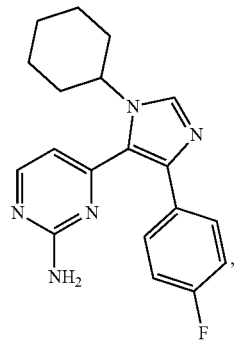

PF-670462

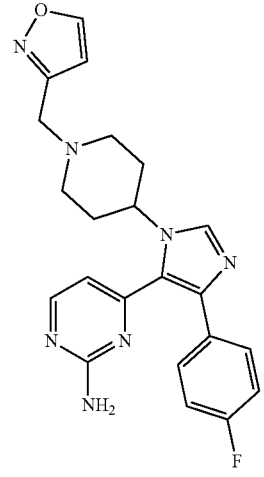

PF-5006739

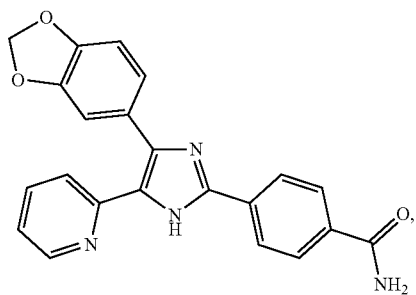

SB-431542

-continued

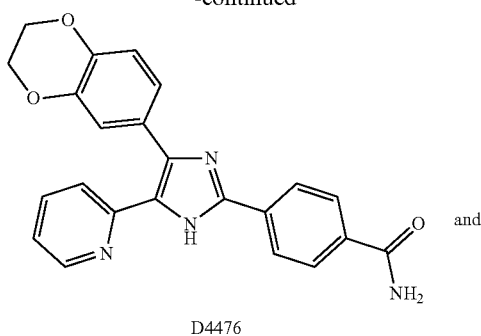
D4476 and

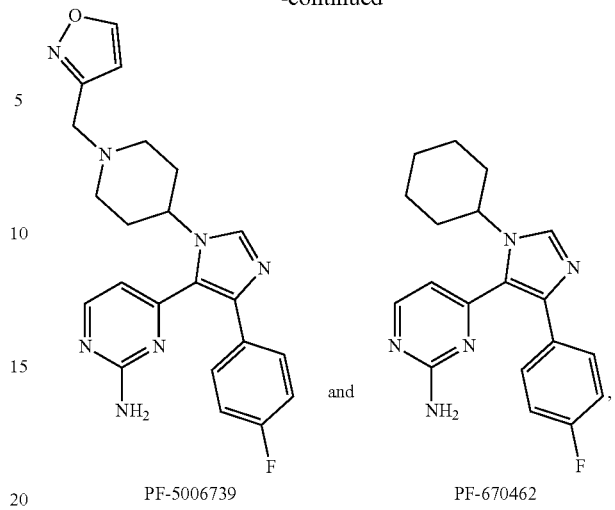
PF-5006739    and    PF-670462 or a pharmaceutically acceptable salt, polymorph or prodrug thereof.

In another preferred embodiment, the compound is an ALK5 inhibitor selected from:

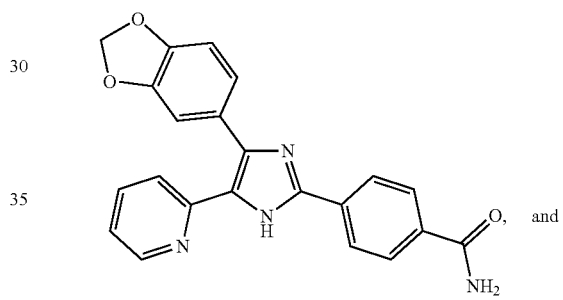
SB-431542 and

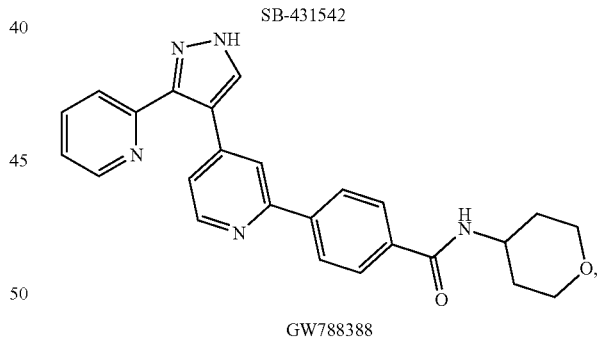
GW788388 or a pharmaceutically acceptable salt, polymorph or prodrug thereof.

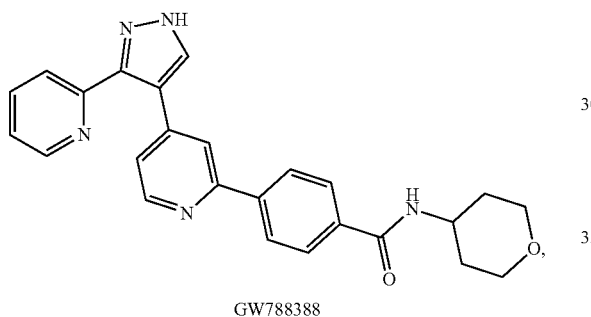
GW788388 or a pharmaceutically acceptable salt, polymorph or prodrug thereof.

In one particularly preferred embodiment, the compound is a casein kinase 1 inhibitor selected from the group consisting of:

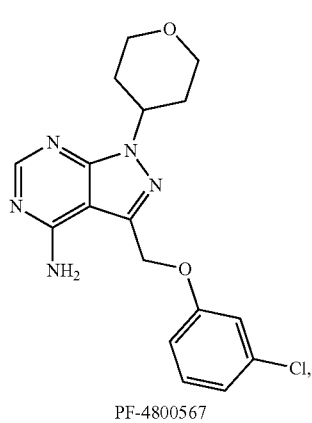
PF-4800567

The term 'pharmaceutically-acceptable salts' refers to those salts which, within the scope of sound medical judgement, are suitable for use in contact with the tissues of humans and animals without undue toxicity, irritation, allergic response and the like, and are commensurate with a reasonable benefit/risk ratio. Pharmaceutically acceptable salts are well known in the art. S. M. Berge et al. describe pharmaceutically acceptable salts in detail in J. Pharmaceutical Sciences, 1977, 66:1-19. The salts include relatively non-toxic, inorganic and organic acid salts of any small molecule inhibitors, as appropriate. For example, salts of PF-670462, PF-4800567, PF-5006739, SB-431542, D4476, GW788388 or LH846. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, ascorbic, glucoronic, fumaric, maleic, pyruvic, alkyl sulfonic, arylsulfonic, aspartic, glutamic, benzoic, anthranilic, mesylic, salicylic, p-hydroxybenzoic, phenylacetic, mandelic, ambonic, pamoic, pantothenic, sulfanilic, cyclohexylaminosulfonic, stearic, algenic, β-hydroxybutyric, galactaric, and galacturonic acids. Suitable pharmaceutically acceptable base addition salts of the compounds of the present invention include metallic salts made from lithium, sodium, potassium, magnesium, calcium, aluminium, and zinc, and organic salts made from organic bases such as choline, diethanolamine, morpholine. Alternatively, organic salts made from N,N'-dibenzylethylenediamine, chloroprocaine, choline, diethanolamine, ethylenediamine, meglumine (N methylglucamine), procaine, ammonium salts, quaternary salts such as tetramethylammonium salt, amino acid addition salts such as salts with glycine and arginine.

For example, alkali metal salts (K, Na) and alkaline earth metal salts (Ca, Mg) may be used if deemed appropriate for the structure, but again any pharmaceutically acceptable, non-toxic salt may be used where appropriate. The Na- and Ca-salts are preferred.

'Prodrug' means a compound which is convertible in vivo by metabolic means (e.g. by hydrolysis, reduction or oxidation) to a compound of the present invention. For example an ester prodrug of a compound of the present invention containing a hydroxyl group may be convertible by hydrolysis in vivo to the parent molecule. Where esters can be formed, suitable esters are, for example, acetates, citrates, lactates, tartrates, malonates, oxalates, salicylates, propionates, succinates, fumarates, maleates, methylene-bis-β-hydroxynaphthoates, gestisates, isethionates, di-p-toluoyl-tartrates, methanesulphonates, ethanesulphonates, benzenesulphonates, p-toluenesulphonates, cyclohexylsulphamates and quinates.

It has been known for a considerable period of time that development of drugs that have designed metabolic or chemical instability could improve the lung/airway/nasal selectivity. Specifically, this concept of "soft drug" can be practiced by compounds that are rapidly degraded or metabolised upon their absorption from the airway wall and lung spaces into the bronchial or pulmonary circulation. Examples of such compounds are provided in Belvisi M. & Hele, D. J. *Pulmonary Pharmacology & Therapeutics* (2003) 16, 321 and Druzgala, P et al *J. Steroid Biochera. Molec. Biol.* (1991) 38 (2), 149-154. It is contemplated that the compounds of the present invention may act as soft drugs.

Pharmaceutically acceptable solvates, including hydrates, of such compounds and such salts are also intended to be included within the scope of this invention.

In the case of small molecule inhibitors that are solids, it will be understood by those skilled in the art that the compounds, agents and salts may exist in different crystalline or polymorphic forms, all of which are intended to be within the scope of the present invention and specified formulae.

The term 'polymorph' includes any crystalline form of compounds of any compound described herein, such as anhydrous forms, hydrous forms, solvate forms and mixed solvate forms.

TABLE 1

CK1ε and ALK5 inhibition by a several kinase inhibitors that were effective in preventing loss of GC activity in TGFβ-treated BEAS-2B.

| Kinase inhibitor | IC$_{50}$ CK1δ (nM)[1] | IC$_{50}$ CK1ε (nM) | IC$_{50}$ ALK5 (nM) |
|---|---|---|---|
| PF670462 | 14 | 56 | 1160 |
| PF4800567 | 711 | 11 | 4130 |
| D4776 | 7610 | 607 | 540 |
| SB431542 | 920 | 646 | 93 |
| GW788388 | NA | 18,630 | 14 |

[1]Data for CK1δ from Badura JPET 322: 730-38; Walton JPET 330: 430-39; Vogt Cell Signal. 23: 1831-42.
NA = not available SB431542 is an inhibitor of the TGFβ receptor kinase known as ALK5. This compound is thought to block all signalling from the activated TGFβ receptor. GW788388 is also an ALK5 inhibitor.

The phrase 'therapeutically effective amount' generally refers to an amount of one or more inhibitors, or, if a small molecule inhibitor, a pharmaceutically acceptable salt, polymorph or prodrug thereof of the present invention that (i) treats the particular disease, condition, or disorder, (ii) attenuates, ameliorates, or eliminates one or more symptoms of the particular disease, condition, or disorder, or (iii) delays the onset of one or more symptoms of the particular disease, condition, or disorder described herein.

A subject that is resistant to a treatment involving a glucocorticoid is a subject who has experienced at least one episode where an exacerbation of the underlying respiratory disease was not controlled by a treatment that includes a glucocorticoid. Alternatively, the subject exhibits a response to treatment that includes a glucocorticoid was insufficient to normalise lung function or other aspect of the pathology. Typically, the treatment is an inhaled glucocorticoid (ICS), or ICS in combination with long-acting β2-adrenoceptor agonists (LABA). Exacerbations in patients who are taking combination therapy of ICS/LABA defines the exacerbations as resistant to treatment with glucocorticoids.

A subject with severe obstructive disease is typically one who does not experience lung function normalization when treated with ICS, or ICS/LABA, even in the absence of a respiratory tract infection.

A subject who may benefit from the treatment described herein is a subject in whom use of a glucocorticoid is contraindicated or must be avoided because of age or other medical condition.

ALK5 is also known as the TGFB receptor (TGFBR1; AAT5; ACVRLK4; ALK-5; ALK5; ESS1; LDS1; LDS1A; LDS2A; MSSE; SKR4; TGFR-1). As used herein, the term 'ALK5" is used to denote a TGF-beta receptor type I having serine/threonine protein kinase activity (also referred to herein as TGFβR-1). The term 'TGF-beta receptor' or 'TGFβR' is used herein to encompass all three sub-types of the TGFβR family (i.e., TGFβR-1, TGFβR-2, TGFβR-3). The TGFβ receptors are characterized by serine/threonine kinase activity and exist in several different isoforms that can be homo- or heterodimeric.

As used herein, an 'inhibitor of ALK5' is any compound that inhibits the activity of ALK5. The compound may reduce the binding of TGF beta to ALK5, reduce receptor oligomerization or reduce the serine/threonine kinase activity of ALK5.

As used herein, 'preventing' or 'prevention' is intended to refer to at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease). Biological and physiological parameters for identifying such patients are provided herein and are also well known by physicians.

The terms 'treatment' or 'treating' of a subject includes the application or administration of a compound of the invention to a subject (or application or administration of a compound of the invention to a cell or tissue from a subject) with the purpose of delaying, slowing, stabilizing, curing, healing, alleviating, relieving, altering, remedying, less worsening, ameliorating, improving, or affecting the disease or condition, the symptom of the disease or condition, or the risk of (or susceptibility to) the disease or condition. The term 'treating' refers to any indication of success in the treatment or amelioration of an injury, pathology or condition, including any objective or subjective parameter such as abatement; remission; lessening of the rate of worsening; lessening severity of the disease; stabilization, diminishing of symptoms or making the injury, pathology or condition more tolerable to the subject; slowing in the rate of degeneration or decline; making the final point of degeneration less debilitating; or improving a subject's physical or mental well-being.

The term 'antagonizing' used herein is intended to mean 'decreasing' or 'reducing'. A sufficient period of time can be during one week, or between 1 week to 1 month, or between 1 to 2 months, or 2 months or more. For chronic condition, the compound of the present invention can be advantageously administered for life time period.

The term 'respiratory' refers to the process by which oxygen is taken into the body and carbon dioxide is discharged, through the bodily system including the nose, throat, larynx, trachea, bronchi and lungs.

The term 'respiratory disease' or 'respiratory condition' refers to any one of several ailments that involve inflammation and affect a component of the respiratory system including the upper (including the nasal cavity, pharynx and larynx) and lower respiratory tract (including trachea, bronchi and lungs). Such ailments include pulmonary fibrosis (interstitial lung diseases), rhino sinusitis, influenza, sarcoidosis, bronchial carinoma, silicosis, pneumoconiosis, ventilation-induced lung injury, congenital emphysema, bronchiectasis, nasal polyps, asbestosis, mesothelioma, pulmonary eosinophilia, diffuse pulmonary haemorrhage syndromes, bronchiolitis obliterans, alveolar proteinosis, collagen and vascular disorders affecting the lung, cough. Preferably, the respiratory disease is an obstructive airway disease, such ailments include asthmatic conditions including hay fever, allergen-induced asthma, exercise-induced asthma, pollution-induced asthma, cold-induced asthma, stress-induced asthma and viral-induced-asthma, chronic obstructive pulmonary diseases including chronic bronchitis with normal airflow, chronic bronchitis with airway obstruction (chronic obstructive bronchitis), emphysema, asthmatic bronchitis, and bullous disease, and other pulmonary diseases involving inflammation including cystic fibrosis, pigeon fancier's disease, farmer's lung, acute respiratory distress syndrome, pneumonia, aspiration or inhalation injury, fat embolism in the lung, acidosis inflammation of the lung, acute pulmonary edema, acute mountain sickness, post-cardiac surgery, acute pulmonary hypertension, persistent pulmonary hypertension of the newborn, perinatal aspiration syndrome, hyaline membrane disease, acute pulmonary thromboembolism, heparin-protamine reactions, sepsis, status asthmaticus and hypoxia. The inflammation in the upper and lower respiratory tract may be associated with or caused by viral infection or an allergen. It is expected that the anti-inflammatory activity of the compounds either alone or when co-administered with a glucocorticoid would make them particularly suitable for treatment of these disease or conditions.

The respiratory disease or condition may be associated with or caused by an allergen, such as house dust mite. The present invention finds particular application to allergic disease of the airway or lung and exacerbations of that disease, such as exacerbations resulting from viral infection (e.g. RSV infection).

A symptom of respiratory disease may include cough, excess sputum production, a sense of breathlessness or chest tightness with audible wheeze. Exercise capacity may be quite limited. In asthma the FEV1.0 (forced expiratory volume in one second) as a percentage of that predicted nomographically based on weight, height and age, may be decreased as may the peak expiratory flow rate in a forced expiration. In COPD the FEV1.0 as a ratio of the FVC is typically reduced to less than 0.7. In IPF there is a progressive fall in FVC. The impact of each of these conditions may also be measured by days of lost work/school, disturbed sleep, requirement for bronchodilator drugs, requirement for glucocorticoids including oral glucocorticoids.

The existence of, improvement in, treatment of or prevention of a respiratory disease may be by any clinically or biochemically relevant method of the subject or a biopsy therefrom. For example, a parameter measured may be the presence or degree of lung function, signs and symptoms of obstruction; exercise tolerance; night time awakenings; days lost to school or work; bronchodilator usage; ICS dose; oral GC usage; need for other medications; need for medical treatment; hospital admission.

As used herein, the term 'asthma' refers to a respiratory disorder characterized by episodic difficulty in breathing brought on by any one or a combination of three primary factors including: 1) bronchospasm (i.e., variable and reversible airway obstruction due to airway muscle contraction), 2) inflammation of the airway lining, and 3) bronchial hyper-responsiveness resulting in excessive mucous in the airways, which may be triggered by exposure to an allergen or combination of allergens (i.e., dust mites and mold), viral or bacterial infection (i.e., common cold virus), environmental pollutants (i.e., chemical fumes or smoke), physical over exertion (i.e., during exercise), stress, or inhalation of cold air. The term 'asthmatic condition,' as used herein, refers to the characteristic of an individual to suffer from an attack of asthma upon exposure to any one or a number of asthma triggers for that individual. An individual may be characterized as suffering from, for example, allergen-induced asthma, exercise-induced asthma, pollution-induced asthma, viral-induced asthma, or cold-induced asthma.

The efficacy of a treatment for asthma may be measured by methods well-known in the art, for example, increase in pulmonary function (spirometry), decrease in asthma exacerbations, increase in morning peak expiratory flow rate, decrease in rescue medication use, decrease in daytime and night-time asthma symptoms, increase in asthma-free days, increase in time to asthma exacerbation, and increase in forced expiratory volume in one second (FEV1.0).

The terms 'chronic obstructive pulmonary disease' and 'COPD' as used interchangeably herein refers to a chronic disorder or combination of disorders characterized by reduced maximal expiratory flow and slow forced emptying of the lungs that does not change markedly over several months and is not, or is only minimally, reversible with traditional bronchodilators. Most commonly, COPD is a combination of chronic bronchitis, i.e. the presence of cough and sputum for more than three months for about two consecutive years, and emphysema, i.e. alveolar damage. However, COPD can involve chronic bronchitis with normal airflow, chronic bronchitis with airway obstruction (chronic obstructive bronchitis), emphysema, asthmatic bronchitis, and bullous disease, and combinations thereof. Chronic obstructive pulmonary disease is a condition usually but not exclusively resulting from chronic lung damage induced by exposure to tobacco smoke. Other noxious airborne pollutants, such as indoor cooking exhaust and car exhaust may over the long-term cause or increase the risk of COPD.

The phrase 'a condition of the airway or lung involving fibrosis' or 'a condition of the airway or lung having a fibrotic component' includes any disease or condition where there is the formation or development of excess fibrous connective tissue (fibrosis) in the airway or lung thereby resulting in the development of scarred (fibrotic) tissue. This includes pulmonary fibrosis, 'lung fibrosis or Idiopathic pulmonary fibrosis (IPF). More precisely, pulmonary fibrosis is a chronic disease that causes swelling and scarring of the alveoli and interstitial tissues of the lungs. The scar tissue replaces healthy tissue and causes inflammation. This damage to the lung tissue causes stiffness of the lungs which subsequently makes breathing more and more difficult.

'Idiopathic pulmonary fibrosis (IPF)' is a specific manifestation of idiopathic interstitial pneumonia (IIP), a type of interstitial lung disease. Interstitial lung disease, also known as diffuse parenchymal lung disease (DPLD), refers to a group of lung diseases affecting the interstitium. Microscopically, lung tissue from IPF patients shows a characteristic set of histological features known as usual interstitial pneumonia (UIP). UIP is therefore the pathologic presentation of IPF.

The existence of, improvement in, treatment of or prevention of a condition of the airway or lung involving fibrosis, particularly pulmonary fibrosis/lung fibrosis or Idiopathic pulmonary fibrosis may be by any clinically or biochemically relevant method of the subject or a biopsy therefrom. For example, a parameter measured may be the presence or degree of fibrosis, the content of collagen, fibronectin, or another extracellular matrix protein, the proliferation rate of the cells or any extracellular matrix components in the cells or transdifferentiation of the cells to myofibroblasts.

The therapeutically effective amount of the formulation depends on the severity of the specific respiratory disease indication (e.g. severe chronic asthma), the patient's clinical history and response, and the discretion of the attending physician. The formulation may be administered to the patient at one time or over a series of treatments. An initial candidate dosage may be administered to a patient and the proper dosage and treatment regimen established by monitoring the progress of this patient using conventional techniques well known to those of ordinary skill in the art. Preferably, the therapeutically effective concentration of the active compound will be in the range 0.1 nM to 100 µM. More preferably the range will be 0.1-10 µM. However, it will be appreciated that delivery by inhalation can result in cells within the airway being exposed for short periods of time to concentrations exceeding those quoted above, for a period of time whilst the drug is being diluted in the airway surface fluid and also being absorbed from the airway and lung surfaces.

The amount of active ingredients that may be combined with the carrier materials to produce a single dosage form will vary depending upon the subject treated and the particular mode of administration. It will be understood, however, that the specific dose level for any particular patient will depend upon a variety of factors, including the activity of the specific formulation employed, the age, body weight, general health, sex, diet, time of administration, route of administration, rate of excretion, drug combination and the severity of the particular disease undergoing therapy, and can be determined by those skilled in the art.

The amount of a pharmaceutical formulation that is capable of preventing or slowing the development of a disease in a mammal is referred to as a 'prophylactically effective dose.' The particular dose required for a prophylactic treatment will depend upon the medical condition and history of the mammal, the particular disease being prevented, as well as other factors such as age, weight, gender, administration route, efficiency, etc. Such prophylactic treatments may be used, e.g., in a mammal that has previously had disease to prevent a recurrence of the disease, or in a mammal that is suspected of having a significant likelihood of developing disease.

In one aspect, the method of treatment of the present invention further comprises administering a concomitant medication for the target disease indication. For example, concomitant asthma medications (for both chronic and acute) that may be used with the method of the present invention include but are not limited to: inhaled and oral steroids (e.g. beclomethasone, budesonide, flunisolide, fluticasone, triamcinolone, mometasone); systemic corticosteroids (e.g. methylprednisolone, prednisolone, prednisone, dexamethasone, and deflazacort); inhaled or oral β2 agonists (e.g. salmeterol, formoterol, bitolterol, pirbuterol, terbutaline, bambuterol and albuterol); cromolyn and nedocromil; anti-allergic opthalmic medications (e.g. dexamethasone); methylxanthines (e.g. theophylline and mepyramine-theophylline acetate); leukotriene modifying agents (e.g. zafirlukast, zileuton, montekulast and pranlukast); anticholinergics (e.g. ipatropium bromide); other therapeutic antibodies for any format (e.g. antibodies directed against intracellular adhesion molecules or IgE, those antibodies in monoclonal form, Fab, scFV, etc), antibody mimetics (e.g. anticalin) or peptides; thromboxane A2 synthetase inhibitors; thromboxane prostanoid receptor antagonists; other eicosanoid modifiers (e.g. alprostadil vs. PGE1, dinoprostone vs. PGE2, epoprostenol vs. prostacyclin and PGI2 analogues (e.g. PG12 beraprost), seratrodast, phosphodiesterase 4 isoenzyme inhibitors, thromboxane A2 synthetase inhibitors (e.g. ozmagrel, dazmegrel or ozagrel); ditec (low dose disodium cromoglycate and fenoterol); platelet activating factor receptor antagonists; antihistamines or histamine antagonists: promethazine, chlorpheniramine, loratadine, cetirazine, azelastine; anti-thromboxane A2; antibradykinins (e.g. icatibant); agents that inhibit activated eosinophils and T-cell recruitment (e.g. ketotifen), IL-13 blockers (e.g. soluble IL-13 receptor fragments), IL-4 blockers (e.g. soluble IL-4 receptor fragments); ligands that bind and block the activity of IL-13 or IL-4, and xanthine derivatives (e.g. pentoxifylline).

The invention also includes the administration of an inhibitor of casein kinase 1 and a medication for the target disease indication as described above where either or both are administered by inhalation or formulated for oral administration.

Although the invention finds application in humans, the invention is also useful for therapeutic veterinary purposes. The invention is useful for domestic or farm animals such as cattle, sheep, horses and poultry; for companion animals such as cats and dogs; and for zoo animals.

Pharmaceutical compositions may be formulated for any appropriate route of administration including, for example, topical (for example, transdermal or ocular), oral, buccal, nasal, vaginal, rectal or parenteral administration. The term parenteral as used herein includes subcutaneous, intradermal, intravascular (for example, intravenous), intramuscular, spinal, intracranial, intrathecal, intraocular, periocular, intraorbital, intrasynovial and intraperitoneal injection, as well as any similar injection or infusion technique. In certain embodiments, compositions in a form suitable for oral use or parenteral use are preferred. Suitable oral forms include, for example, tablets, troches, lozenges, aqueous or oily suspensions, dispersible powders or granules, emulsions, hard or soft capsules, or syrups or elixirs. Within yet other embodiments, compositions provided herein may be formulated as a lyophilizate.

The various dosage units are each preferably provided as a discrete dosage tablet, capsules, lozenge, dragee, gum, or other type of solid formulation. Capsules may encapsulate a powder, liquid, or gel. The solid formulation may be swallowed, or may be of a suckable or chewable type (either frangible or gum-like). The present invention contemplates dosage unit retaining devices other than blister packs; for example, packages such as bottles, tubes, canisters, packets. The dosage units may further include conventional excipients well-known in pharmaceutical formulation practice, such as binding agents, gellants, fillers, tableting lubricants, disintegrants, surfactants, and colorants; and for suckable or chewable formulations.

Compositions intended for oral use may further comprise one or more components such as sweetening agents, flavouring agents, colouring agents and/or preserving agents in order to provide appealing and palatable preparations. Tablets contain the active ingredient in admixture with physiologically acceptable excipients that are suitable for the manufacture of tablets. Such excipients include, for example, inert diluents such as calcium carbonate, sodium carbonate, lactose, calcium phosphate or sodium phosphate, granulating and disintegrating agents such as corn starch or alginic acid, binding agents such as starch, gelatine or acacia, and lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatine capsules wherein the active ingredient is mixed with an inert solid diluent such as calcium carbonate, calcium phosphate or kaolin, or as soft gelatine capsules wherein the active ingredient is mixed with water or an oil medium such as peanut oil, liquid paraffin or olive oil.

Aqueous suspensions contain the active ingredient(s) in admixture with excipients suitable for the manufacture of aqueous suspensions. Such excipients include suspending agents such as sodium carboxymethylcellulose, methylcellulose, hydropropylmethylcellulose, sodium alginate, polyvinylpyrrolidone, gum tragacanth and gum acacia, and dispersing or wetting agents such as naturally-occurring phosphatides (for example, lecithin), condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol mono-oleate, or condensation products of ethylene oxide with partial esters derived from fatty acids and hexitol anhydrides such as polyethylene sorbitan monooleate. Aqueous suspensions may also comprise one or more preservatives, for example ethyl, or n-propyl p-hydroxybenzoate, one or more colouring agents, one or more flavouring agents, and one or more sweetening agents, such as sucrose or saccharin.

Oily suspensions may be formulated by suspending the active ingredients in a vegetable oil such as arachis oil, olive oil, sesame oil or coconut oil, or in a mineral oil such as liquid paraffin. The oily suspensions may contain a thickening agent such as beeswax, hard paraffin or cetyl alcohol. Sweetening agents such as those set forth above, and/or flavouring agents may be added to provide palatable oral preparations. Such suspensions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, such as sweetening, flavouring and colouring agents, may also be present.

Pharmaceutical compositions may also be in the form of oil-in-water emulsions. The oily phase may be a vegetable oil such as olive oil or arachis oil, a mineral oil such as liquid paraffin, or a mixture thereof. Suitable emulsifying agents include naturally-occurring gums such as gum acacia or gum tragacanth, naturally-occurring phosphatides such as soy bean lecithin, and esters or partial esters derived from fatty acids and hexitol, anhydrides such as sorbitan monoleate, and condensation products of partial esters derived from fatty acids and hexitol with ethylene oxide such as polyoxyethylene sorbitan monoleate. An emulsion may also comprise one or more sweetening and/or flavouring agents.

Syrups and elixirs may be formulated with sweetening agents, such as glycerol, propylene glycol, sorbitol or sucrose. Such formulations may also comprise one or more demulcents, preservatives, flavouring agents and/or colouring agents.

Compounds may be formulated for local or topical administration, such as for topical application to the skin. Formulations for topical administration typically comprise a topical vehicle combined with active agent(s), with or without additional optional components.

Suitable topical vehicles and additional components are well known in the art, and it will be apparent that the choice of a vehicle will depend on the particular physical form and mode of delivery. Topical vehicles include organic solvents such as alcohols (for example, ethanol, iso-propyl alcohol or glycerine), glycols such as butylene, isoprene or propylene glycol, aliphatic alcohols such as lanolin, mixtures of water and organic solvents and mixtures of organic solvents such as alcohol and glycerine, lipid-based materials such as fatty acids, acylglycerols including oils such as mineral oil, and fats of natural or synthetic origin, phosphoglycerides, sphingolipids and waxes, protein-based materials such as collagen and gelatine, silicone-based materials (both nonvolatile and volatile), and hydrocarbon-based materials such as microsponges and polymer matrices.

A composition may further include one or more components adapted to improve the stability or effectiveness of the applied formulation, such as stabilizing agents, suspending agents, emulsifying agents, viscosity adjusters, gelling agents, preservatives, antioxidants, skin penetration enhancers, moisturizers and sustained release materials. Examples of such components are described in Martindale—The Extra Pharmacopoeia (Pharmaceutical Press, London 1993) and Martin (ed.), Remington's Pharmaceutical Sciences. Formulations may comprise microcapsules, such as hydroxymethylcellulose or gelatine-microcapsules, liposomes, albumin microspheres, microemulsions, nanoparticles or nanocapsules.

A topical formulation may be prepared in a variety of physical forms including, for example, solids, pastes, creams, foams, lotions, gels, powders, aqueous liquids, emulsions, sprays and skin patches. The physical appearance and viscosity of such forms can be governed by the presence and amount of emulsifier(s) and viscosity adjuster(s) present in the formulation. Solids are generally firm and non-pourable and commonly are formulated as bars or sticks, or in particulate form. Solids can be opaque or transparent, and optionally can contain solvents, emulsifiers, moisturizers, emollients, fragrances, dyes/colorants, preservatives and other active ingredients that increase or enhance the efficacy of the final product. Creams and lotions are often similar to one another, differing mainly in their viscosity. Both lotions and creams may be opaque, translucent or clear and often contain emulsifiers, solvents, and viscosity adjusting agents, as well as moisturizers, emollients, fragrances, dyes/colorants, preservatives and other active ingredients that increase or enhance the efficacy of the final product. Gels can be prepared with a range of viscosities, from thick or high viscosity to thin or low viscosity. These formulations, like those of lotions and creams, may also contain solvents, emulsifiers, moisturizers, emollients, fragrances, dyes/colorants, preservatives and other active ingredients that increase or enhance the efficacy of the final product. Liquids are thinner than creams, lotions, or gels, and often do not contain emulsifiers. Liquid topical products often contain solvents, emulsifiers, moisturizers, emollients, fragrances, dyes/colorants, preservatives and other active ingredients that increase or enhance the efficacy of the final product.

Emulsifiers for use in topical formulations include, but are not limited to, ionic emulsifiers, cetearyl alcohol, non-ionic emulsifiers like polyoxyethylene oleyl ether, PEG-40 stearate, ceteareth-12, ceteareth-20, ceteareth-30, ceteareth alcohol, PEG-100 stearate and glyceryl stearate. Suitable viscosity adjusting agents include, but are not limited to, protective colloids or nonionic gums such as hydroxyethylcellulose, xanthan gum, magnesium aluminum silicate, silica, microcrystalline wax, beeswax, paraffin, and cetyl palmitate. A gel composition may be formed by the addition of a gelling agent such as chitosan, methyl cellulose, ethyl cellulose, polyvinyl alcohol, polyquaterniums, hydroxyethylceilulose, hydroxypropylcellulose, hydroxypropylmethylcellulose, carbomer or ammoniated glycyrrhizinate. Suitable surfactants include, but are not limited to, nonionic, amphoteric, ionic and anionic surfactants. For example, one or more of dimethicone copolyol, polysorbate 20, polysorbate 40, polysorbate 60, polysorbate 80, lauramide DEA, cocamide DEA, and cocamide MEA, oleyl betaine, cocamidopropyl phosphatidyl PG-dimonium chloride, and ammonium laureth sulfate may be used within topical formulations.

Preservatives include, but are not limited to, antimicrobials such as methylparaben, propylparaben, sorbic acid, benzoic acid, and formaldehyde, as well as physical stabilizers and antioxidants such as vitamin E, sodium ascorbate/ascorbic acid and propyl gallate. Suitable moisturizers include, but are not limited to, lactic acid and other hydroxy acids and their salts, glycerine, propylene glycol, and butylene glycol. Suitable emollients include lanolin alcohol, lanolin, lanolin derivatives, cholesterol, petrolatum, isostearyl neopentanoate and mineral oils. Suitable fragrances and colours include, but are not limited to, FD&C Red No. 40 and FD&C Yellow No. 5. Other suitable additional ingredients that may be included in a topical formulation include, but are not limited to, abrasives, absorbents, anticaking agents, antifoaming agents, antistatic agents, astringents (such as witch hazel), alcohol and herbal extracts such as chamomile extract, binders/excipients, buffering agents, chelating agents, film forming agents, conditioning agents, propellants, opacifying agents, pH adjusters and protectants.

Typical modes of delivery for topical compositions include application using the fingers, application using a physical applicator such as a cloth, tissue, swab, stick or brush, spraying including mist, aerosol or foam spraying, dropper application, sprinkling, soaking, and rinsing. Controlled release vehicles can also be used, and compositions may be formulated for transdermal administration (for example, as a transdermal patch).

A pharmaceutical composition may be formulated as inhaled formulations, including sprays, mists, or aerosols. This may be particularly preferred for treatment of a respiratory disease, a condition of the airway or lung involving fibrosis as described herein. The inhaled formulation may be for application to the upper (including the nasal cavity, pharynx and larynx) and lower respiratory tract (including trachea, bronchi and lungs). For inhalation formulations, the composition or combination provided herein may be delivered via any inhalation methods known to a person skilled in the art. Such inhalation methods and devices include, but are not limited to, metered dose inhalers with propellants such as HFA or propellants that are physiologically and environmentally acceptable. Other suitable devices are breath operated inhalers, multidose dry powder inhalers and aerosol nebulizers. Aerosol formulations for use in the subject method typically include propellants, surfactants and co-solvents and may be filled into conventional aerosol containers that are closed by a suitable metering valve. Different devices and excipients can be used depending on whether the application is to the upper (including the nasal cavity, pharynx and larynx) or lower respiratory tract (including trachea, bronchi and lungs) and can be determined by those skilled in the art. Further, processes for micronisation and nanoparticle formation for the preparation of compounds described herein for use in an inhaler, such as a dry powder inhaler, are also known by those skilled in the art.

Inhalant compositions may comprise liquid or powdered compositions containing the active ingredient that are suitable for nebulization and intrabronchial use, or aerosol compositions administered via an aerosol unit dispensing metered doses. Suitable liquid compositions comprise the active ingredient in an aqueous, pharmaceutically acceptable inhalant solvent such as isotonic saline or bacteriostatic water. The solutions are administered by means of a pump or squeeze-actuated nebulized spray dispenser, or by any other conventional means for causing or enabling the requisite dosage amount of the liquid composition to be inhaled into the patient's lungs. Suitable formulations, wherein the carrier is a liquid, for administration, as for example, a nasal spray or as nasal drops, include aqueous or oily solutions of the active ingredient. Examples of inhalation drug delivery devices are described in Ibrahim et al. Medical Devices: Evidence and Research 2015:8 131-139, are contemplated for use in the present invention.

Pharmaceutical compositions may also be prepared in the form of suppositories such as for rectal administration. Such compositions can be prepared by mixing the drug with a suitable non-irritating excipient that is solid at ordinary temperatures but liquid at the rectal temperature and will therefore melt in the rectum to release the drug. Suitable excipients include, for example, cocoa butter and polyethylene glycols.

Pharmaceutical compositions may be formulated as sustained or protracted release formulations such as a capsule that creates a slow release of modulator following administration. Such formulations may generally be prepared using well-known technology and administered by, for example, oral, rectal or subcutaneous implantation, or by implantation at the desired target site. Carriers for use within such formulations are biocompatible, and may also be biodegradable. Preferably, the formulation provides a relatively constant level of modulator release. The amount of modulator contained within a sustained release formulation depends upon, for example, the site of implantation, the rate and expected duration of release and the nature of the condition to be treated or prevented.

In another embodiment there is provided a kit or article of manufacture including any one or more inhibitors of casein kinase 1 and/or ALK5, or a pharmaceutically acceptable salt, polymorph or prodrug thereof and/or pharmaceutical composition as described above.

In other embodiments there is provided a kit for use in a therapeutic or prophylactic application mentioned above, the kit including:
 a container holding a therapeutic composition in the form of any one or more inhibitors of casein kinase 1 and/or ALK5, or a pharmaceutically acceptable salt, polymorph or prodrug thereof or pharmaceutical composition;
 a label or package insert with instructions for use.

In certain embodiments the kit may contain one or more further active principles or ingredients for treatment of a condition or disease described herein.

The kit or 'article of manufacture' may comprise a container and a label or package insert on or associated with the container. Suitable containers include, for example, bottles, vials, syringes, blister pack, etc. The containers may be formed from a variety of materials such as glass or plastic. The container holds a therapeutic composition which is effective for treating the condition and may have a sterile access port (for example the container may be an intravenous solution bag or a vial having a stopper pierceable by a hypodermic injection needle). The label or package insert indicates that the therapeutic composition is used for treating the condition of choice. In one embodiment, the label or package insert includes instructions for use and indicates that the therapeutic or prophylactic composition can be used to treat a fibrotic disease described herein.

The kit may comprise (a) a therapeutic or prophylactic composition; and (b) a second container with a second active principle or ingredient contained therein. The kit in this embodiment of the invention may further comprise a package insert indicating the composition and other active principle can be used to treat a disorder or prevent a complication stemming from a fibrotic disease described herein. Alternatively, or additionally, the kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain embodiments the therapeutic composition may be provided in the form of a device, disposable or reusable, including a receptacle for holding the therapeutic, prophylactic or pharmaceutical composition. In one embodiment, the device is a syringe. The device may hold 1-2 mL of the therapeutic composition. The therapeutic or prophylactic composition may be provided in the device in a state that is ready for use or in a state requiring mixing or addition of further components.

It will be understood, that the specific dose level for any particular patient will depend upon a variety of factors including the activity of the specific compound employed, the age, body weight, general health, sex, diet, time of administration, route of administration, and rate of excretion, drug combination (i.e. other drugs being used to treat the patient), and the severity of the particular disorder undergoing therapy.

It will be understood that the invention disclosed and defined in this specification extends to all alternative combinations of two or more of the individual features mentioned or evident from the text or drawings. All of these different combinations constitute various alternative aspects of the invention.

A number of abbreviations and gene products are mentioned in the text. A brief explanation of the meaning and significance of those terms is provided.

ALI—air liquid interface is generated by removing the fluid from cultured epithelial cells to induce differentiation of basal epithelial cells into an organotypic culture closely resembling the epithelial layer of human airways.

Bud—budesonide is an inhaled corticosteroid (ICS) used in the treatment of asthma and COPD.

CDKN1C—encodes the cyclin-dependent kinase inhibitor, $p57^{kip2}$ which may mediate some of the growth inhibitory actions of glucocorticoids.

CK1—casein kinase 1 family comprising 7 different members, of which the δ and ε isoforms (CK1δ and CK1ε) are of most relevance to the actions of PF670462.

Col1A—collagen 1a is a subunit of the fibrillar type collagen that is deposited in excess in the extracellular matrix in fibrotic lesions.

Col3—collagen 3 is a subunit of the fibrillar type collagen that is deposited in excess in the extracellular matrix in fibrotic lesions.

CTGF—connective tissue growth factor is a fibrogen that stimulates collagen deposition and is thought to be a principal mediator of the effects of TGFβ.

Dex—dexamethasone is a glucocorticoid agonist that is usually administered by the oral route. It is often used in in vitro studies on glucocorticoids as a reference compound.

FKBP5—FK binding protein serves as a chaperone for the glucocorticoid receptor and reductions in its levels have been correlated with severe asthma.

Glucocorticoid (GC)—an agent having a cortisol-like agonist action on glucocorticoid receptors resulting in a range of endocrine and anti-inflammatory effects.

GILZ—glucocorticoid-induced leucine zipper protein is thought to mediate a number of the anti-inflammatory actions of glucocorticoids by inhibiting the activations of the pro-inflammatory transcription factor NFκB.

GRE—glucocorticoid response element is a sequence of nucleotides in the promoter regions of genes that have their expression altered by glucocorticoid agonists.

HDM—House dust mite (HDM) is a microscopic animal that lives on human detritus (skin scale). HDM faeces contain a potent allergen that is used to induce airway inflammation in murine models of allergic lung/airway inflammation (Bossios et al, (2008) Clin Exp Allergy, 38(10):16-15-1626).

IL-28A—IL-28A is an anti-viral cytokine also known as interferon lambda (IFNλ).

PAI-1—plasminogen activator inhibitor-1 is a serine protease inhibitor with selectivity for urokinase (also known as urokinase plasminogen activator or uPA) and tissue-type plasminogen activation (tPA). PAI-1 may increase the extent of fibrotic lesions by facilitating the accumulation of fibrin in the airspaces thereby providing a provisional ECM for an invasive fibroplasia.

RV—rhinovirus is the virus responsible for causing the common cold. In asthmatic and COPD patients infections this virus can spread to the lower respiratory tract in association with a worsening of symptoms referred to as an exacerbation.

RSV—respiratory syncytial virus is a virus able to cause severe acute respiratory disease, particularly in infants and in the elderly. Severe RSV infection in childhood is a risk factor for protracted, if not life-long asthma.

SCNN1a encodes the epithelial sodium channel a subunit (ENaCα). The ENaCα channel has a role to limit the accumulation of fluid on the airway surface.

TGFβ—Transforming growth factor β is a pleiotropic cytokine with fibrogenic activity including stimulation of collagen production, activation of fibroblasts to a myofibroblast phenotype, induction of EMT (epithelial mesenchymal transition) and modulation of collagenolytic enzyme expression.

TIMP1—tissue inhibitor of metalloprotease-1 is a regulator of the proteolytic activity of a class of proteases characterised by having a zinc ion that contributes to the structure/function of the active enzyme.

TNFα—Tumour necrosis factorα is a pro-inflammatory cytokine

ZBTB16 also known as PLZF—pro-myeolocytic zinc finger protein is a transcriptional repressor that has been implicated in anti-inflammatory and growth-regulatory actions of glucocorticoids.

It will be understood that these examples are intended to demonstrate these and other aspects of the invention and although the examples describe certain embodiments of the invention, it will be understood that the examples do not limit these embodiments to these things. Various changes can be made and equivalents can be substituted and modifications made without departing from the aspects and/or principles of the invention mentioned above. All such changes, equivalents and modifications are intended to be within the scope of the claims set forth herein.

Example 1

FIG. 1 demonstrates that PF674062 prevents the profound inhibitory effects of TGFβ on glucocorticoid transactivation. BEAS-2B cells (human lung/bronchus epithelial cells) grown in cortisol deficient medium for 24 hours were pretreated with either PF670462 at 1 or 10 µM for 30 min before exposure to TGFβ1 for 24 hours, prior to stimulation by Dexamethasone (30 nM), a concentration previously established to optimally activate glucocorticoid response element (GRE) activity. PF670462 concentration-dependently attenuated the profound TGFβ1-induced suppression of the GRE activity stimulated by Dex (30 nM). Data are presented as the means and SEM of 3 independent experiments. *P<0.05, cf corresponding Dex 30 nM response.

The methods used in Examples 1 to 5 (and 10, 19, 20) are similar to those reported in Salem et al 2012 (Br J Pharmacol. 166:2036-2048) and again in Keenan et al 2014 (Respiratory Research, e15:55) in which methods for cell culture, GRE assays and gene expression measurements are fully described. Additional methods for growth of respiratory syncytial virus (RSV) and rhinovirus (RV) are described in Collins et al 2007 (Respir Physiol Neurobiol. 2007 Jun. 15; 156(3):345-52.) and by Xatzipsalti and papdopoulos, 2007 (Contrib Microbiol. 2007; 14:33-41).

Example 2

Figure 2:
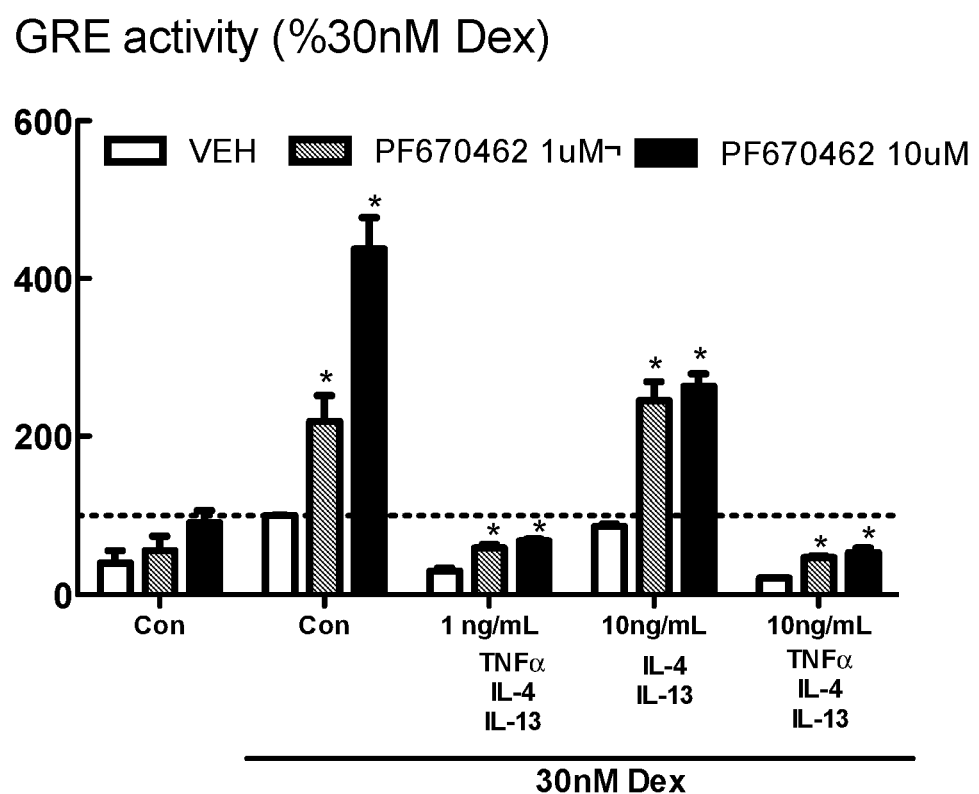
FIG. 2 BEAS-2B cells grown in cortisol deficient medium for 24 hours were pre-treated with either PF670462 at 1 or 10 µM for 30 min before exposure to TGFβ1 for 24 hours, prior to stimulation by Dexamethasone (30 nM), a concentration previously established to optimally activate glucocorticoid response element (GRE)-dependent gene expression. Suppression of glucocorticoid-induced GRE responses to Dex (30 nM) induced by the combination TNFα, IL-13 and IL-4 (each at either 1 or 10 ng/ml) was attenuated by PF670462 treatment. Data are presented as the means and SEM of 3 independent experiments. *P<0.05, cf corresponding Dex 30 nM response.

BEAS-2B cells grown in cortisol deficient medium for 24 hours were pretreated with either PF670462 at 1 or 10 µM for 30 min before exposure to TGFβ1 for 24 hours, prior to stimulation by Dexamethasone (30 nM), a concentration previously established to optimally activate glucocorticoid response element (GRE)-dependent gene expression. Suppression of glucocorticoid-induced GRE responses to Dex (30 nM) induced by the combination TNFα, IL-13 and IL-4 (each at either 1 or 10 ng/ml) was attenuated by PF670462 treatment. Data are presented as the means and SEM of 3 independent experiments. *P<0.05, cf corresponding Dex 30 nM response. FIG. 2 shows a more limited but nevertheless significant effect of PF670462 on various concentrations of combinations of the cytokines, TNFα, IL-13 and IL-4. These cytokines have documented roles in inflammation in asthma and to a somewhat lesser extent in COPD. Furthermore, there are current efforts to target these cytokines using systemically administered biologicals, such as humanized monoclonal antibodies, with limited success in a subset of patients.

Example 3

Figure 3:
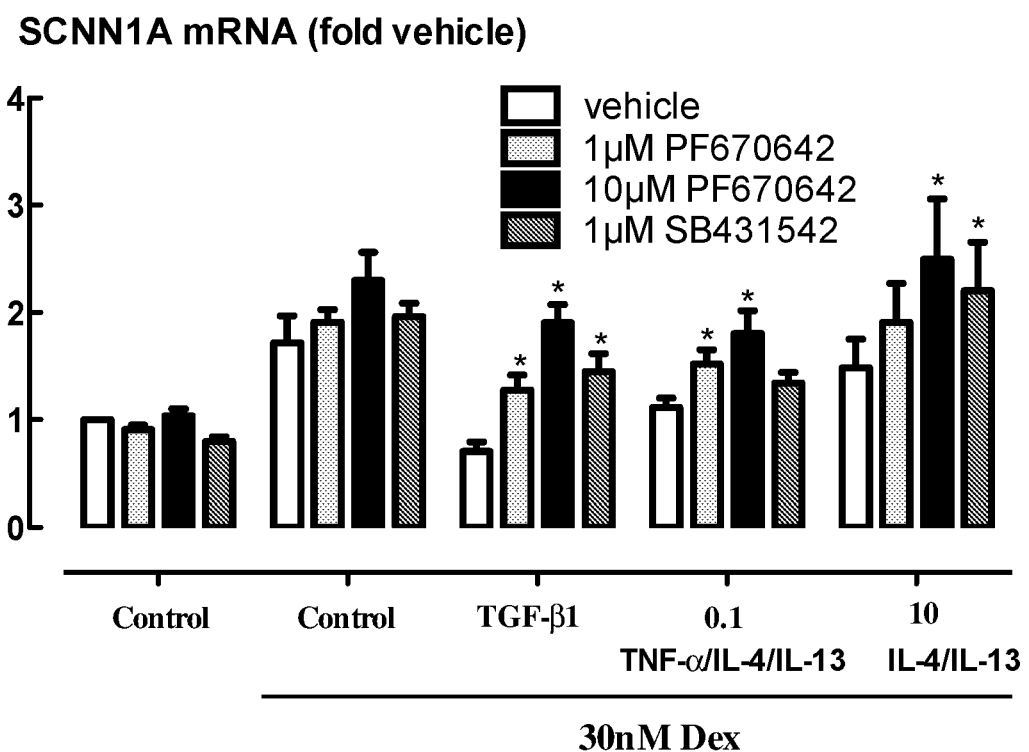
FIG. 3 BEAS-2B cells grown in cortisol deficient medium for 24 hours were pre-treated with either PF670462 at 1 or 10 µM, of the ALK5 inhibitor, SB431542 (1 µM) for 30 min before exposure to TGFβ1 (40 µM) for 24 hours, prior to stimulation by Dexamethasone (30 nM), a concentration previously established to optimally activate glucocorticoid response element (GRE)-dependent gene expression. PF670462 concentration dependently attenuated the profound TGFβ1 induced suppression of selected gene expression responses to Dex (30 nM), exemplified by SCNN1a expression. In addition, suppression induced by the combination TNFα, IL-13 and IL-4 (each at either 0.1) or IL-13/IL-4 (at 10 ng/ml) was partially attenuated by PF670462 treatment. Data are presented as the means and SEM of 4 independent experiments. *P<0.05, cf corresponding Dex 30 nM response.

BEAS-2B cells grown in cortisol deficient medium for 24 hours were pretreated with either PF670462 at 1 or 10 µM, of the ALK5 inhibitor, SB431542 (1 µM) for 30 min before exposure to TGFβ1 (40 µM) for 24 hours, prior to stimulation by Dexamethasone (30 nM), a concentration previously established to optimally activate glucocorticoid response element (GRE)-dependent gene expression. PF670462 concentration dependently attenuated the profound TGFβ1 induced suppression of selected gene expression responses to Dex (30 nM), exemplified by SCNN1a expression. In addition, suppression induced by the combination TNFα, IL-13 and IL-4 each at 0.1 ng/ml or IL-13/IL-4 at 10 ng/ml was partially attenuated by PF670462 treatment. Data are presented as the means and SEM of 4 independent experiments. *P<0.05, cf corresponding Dex 30 nM response. FIG. 3 shows that PF670462 is able to attenuate the resistance induced by the cytokine mixture, but the ALK5 inhibitor, SB431542 appears to be less effective, having no detectable effect against the mixture of TNFα/IL-4 and IL-13, but some impact when only IL-4/IL-13 combination is used to induce the resistant state. Thus, TNFα contribution to glucocorticoid resistance, may be independent of TGFβ. The resistance is exemplified by the epithelial sodium channel alpha subunit SCNN1a which assembles into a Na channel that is thought to contribute to water reabsorption from the airspaces that are flooded during acute lung injury.

Example 4

Figure 4:
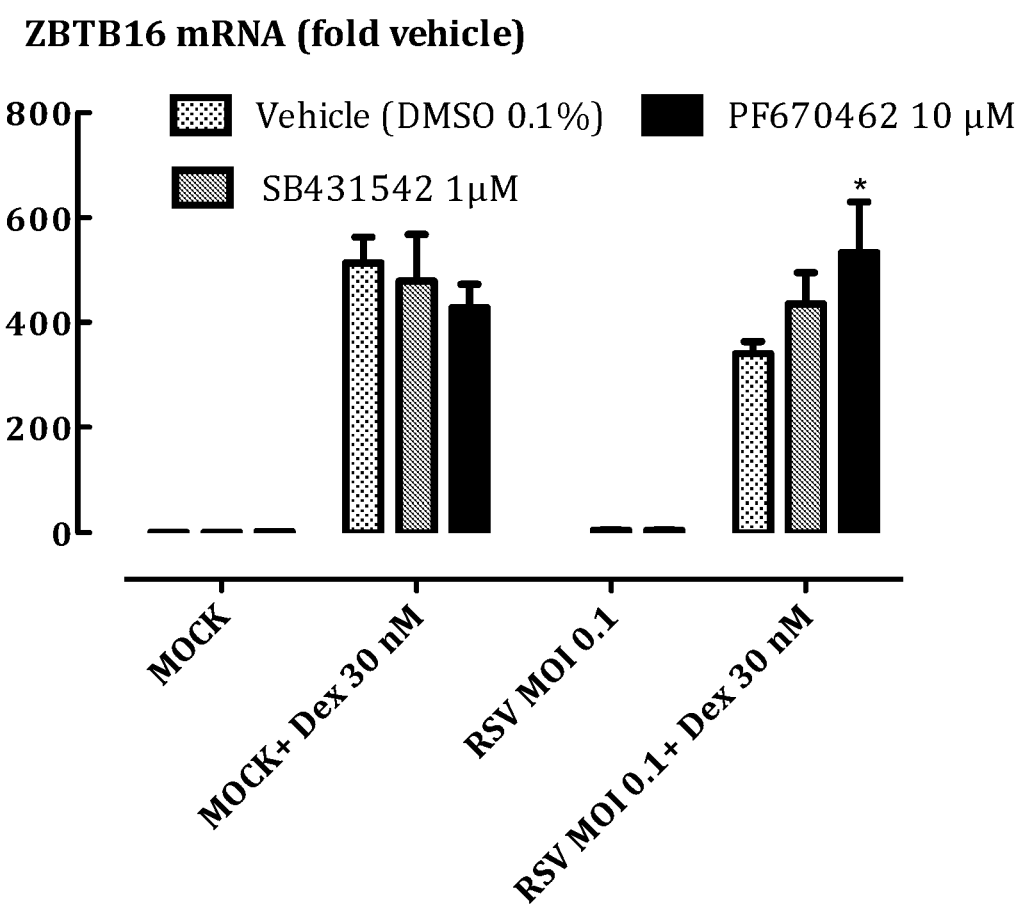
FIG. 4 In this experiment BEAS-2B cells were used in the same setting as those described in FIG. 1, except that the stimulus to impairment of GRE activity was infection with either 0.1 or 1.0 MOI (multiplicity of infection) of respiratory syncytial virus (RSV) or a mock conditioned medium. Pre-treatment with PF670462 prior to inoculation of the culture prevented the impairment of Dexamethasone ZBTB16 gene expression responses. Data are presented as the means and SEM of 4 independent experiments. *P<0.05, cf corresponding Dex 30 nM response.

In this experiment BEAS-2B cells were used in the same setting as those described in FIG. 1, except that the stimulus to impairment of GRE activity was infection with either 0.1 or 1.0 MOI (multiplicity of infection) of respiratory syncytial virus (RSV). Pretreatment with PF670462 prior to inoculation of the culture prevented the impairment of Dexamethasone ZBTB16 gene expression responses. Data are presented as the means and SEM of 4 independent experiments. *P<0.05, cf corresponding Dex 30 nM response. FIG. 4 demonstrates that the GRE activity impairment observed upon exposure to TGFβ, cytokine mixture is also evident with RSV (respiratory syncytial virus) infection, RSV-induced impairment in expression of a very strongly glucocorticoid-induced gene, ZBTB16, was prevented by PF670462. ZBTB16 is also known as PLZF, a myeloid transcription factor of unknown function in epithelium, that nevertheless serves as a sensitive marker of GRE activation.

Example 5

Figure 5:
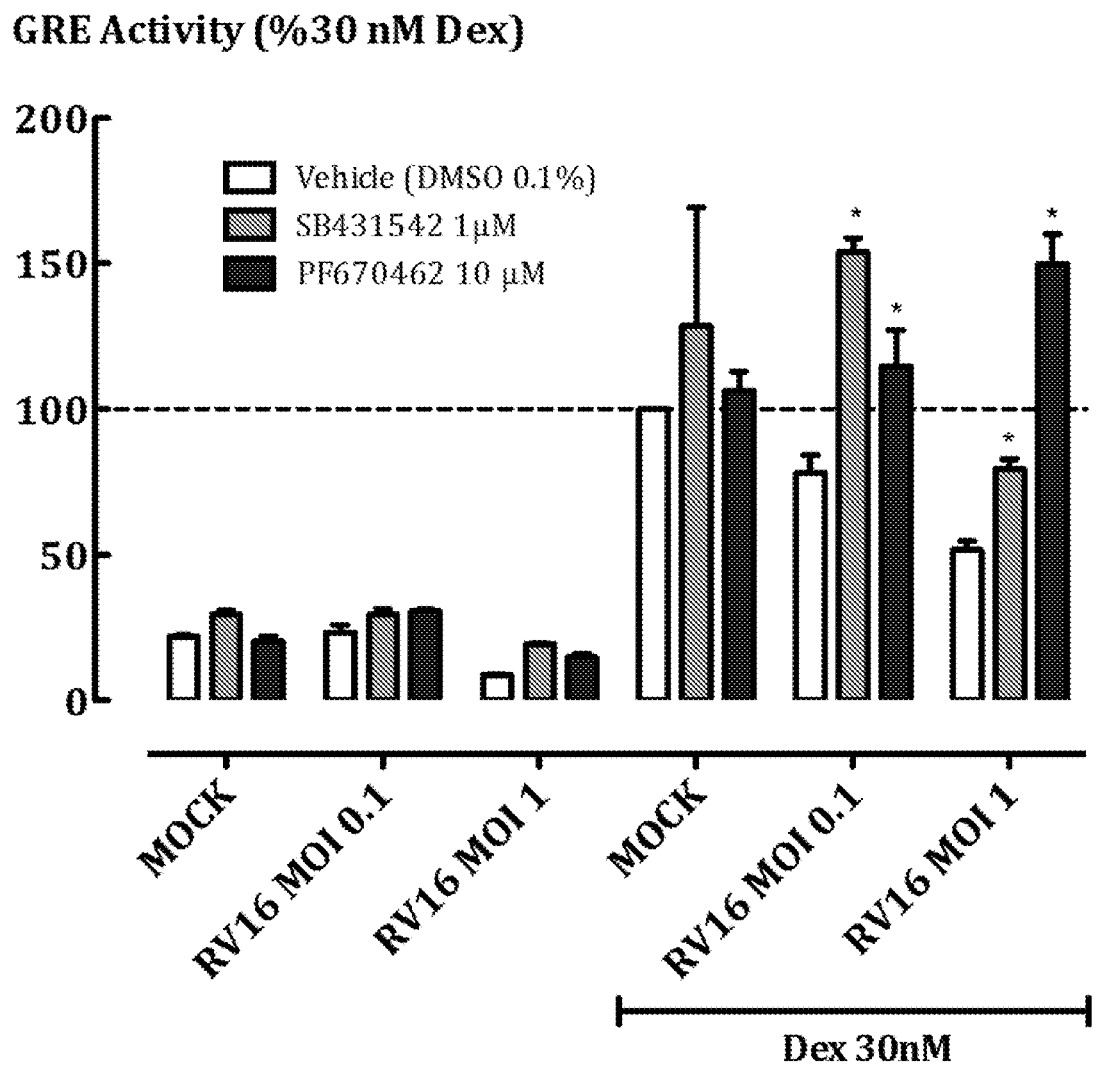
FIG. 5 In this experiment BEAS-2B cells were used in the same setting as those described in FIG. 1, except that the stimulus to impairmenFt of GRE activity was infection with either 0.1 or 1.0 MOI (multiplicity of infection) of Rhinovirus virus (RV16). Pre-treatment with PF670462 prior to inoculation of the culture prevented the impairment of Dexamethasone 30 nM GRE responses, as did pretreatment with the ALK5 inhibitor SB431542 (1 µM). Data are presented as the means and SEM of 4 independent experiments. *P<0.05, cf corresponding Dex 30 nM response.

In this experiment BEAS-2B cells were used in the same setting as those described in Example 1/FIG. 1, except that the stimulus to impairment of GRE activity was infection with either 0.1 or 1.0 MOI (multiplicity of infection) of Rhinovirus virus (RV16). Pretreatment with PF670462 prior to inoculation of the culture prevented the impairment of Dexamethasone 30 nM GRE responses, as did pretreatment with the ALK5 inhibitor SB431542 (1 µM) (FIG. 5). Data are presented as the means and SEM of 4 independent experiments. *P<0.05, cf corresponding Dex 30 nM response.

Figure 6A:
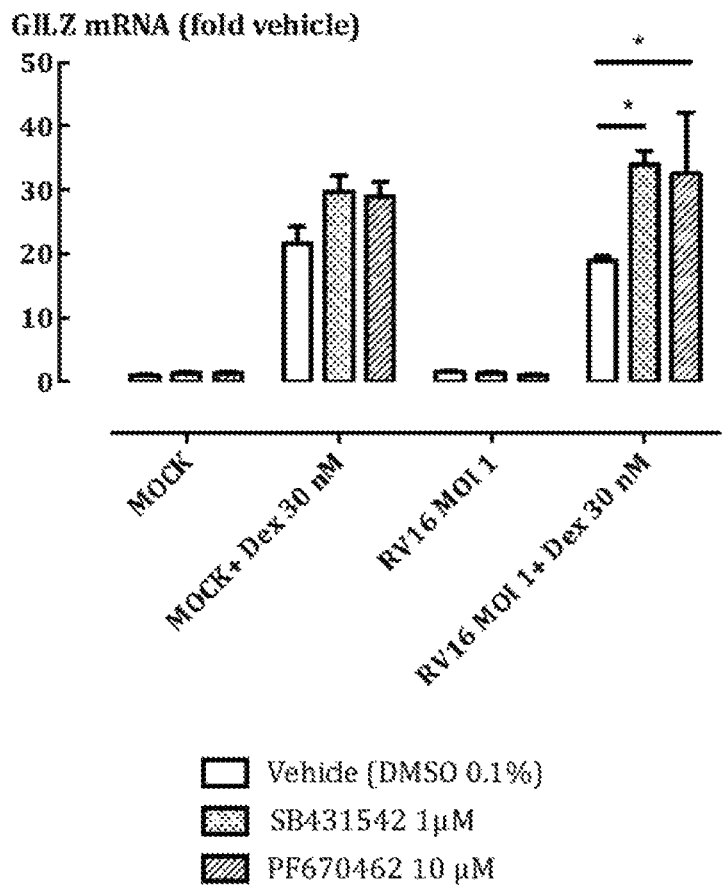
FIGS. 6A-6B In this experiment BEAS-2B cells were used in the same setting as those described in FIG. 1, except that the stimulus to impairment of GRE activity was infection with 1.0 MOI (multiplicity of infection) of Rhinovirus virus (RV16). Pre-treatment with PF670462 prior to inoculation of the culture prevented the impairment of Dexamethasone 30 nM GILZ gene expression responses, as did pre-treatment with the ALK5 inhibitor SB431542. Data are presented as the means and SEM of 4 independent experiments. *P<0.05, cf corresponding Dex 30 nM response.
Figure 6B:
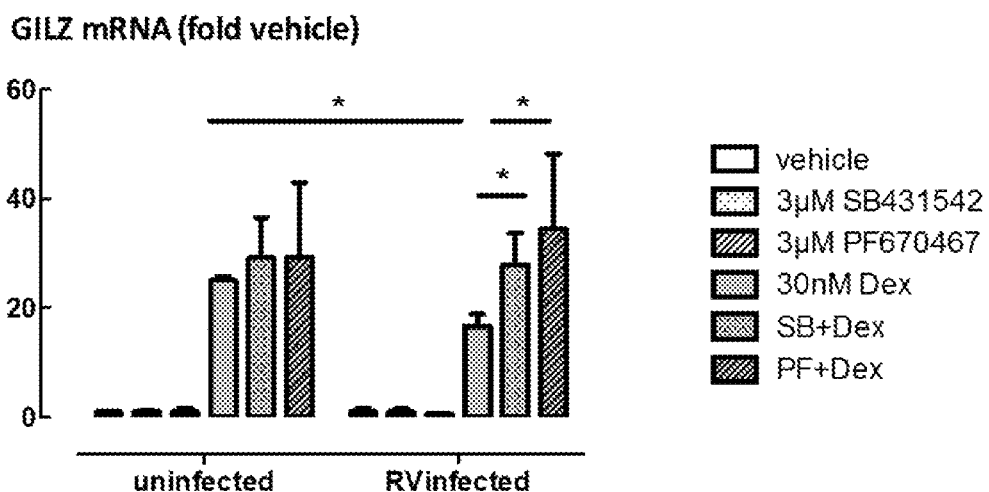

Pretreatment with PF670462 prior to inoculation of the culture greatly diminished the impairment of Dexamethasone 30 nM GILZ gene expression responses, as did pretreatment with the ALK5 inhibitor SB431542 (FIG. 6). Data are presented as the means and SEM of 4 independent experiments. *P<0.05, cf corresponding Dex 30 nM response. Specifically, in FIG. 6A, the data indicate that the levels of GILZ are increased by co-incubation with either SB431542 (1 µM) or with PF670462 (10 µM) in RV infected cells, but not in uninfected cells. In the series of 3 independent experiments shown in FIG. 6B, RV infection significantly decreased Dex-induced GILZ expression and this effect was prevented by either of SB431542 (3 µM) or PF670462 (3 µM). These findings implicate TGFβ signalling through casein kinase 1δ and or ε in the suppressant effects of RV infection on glucocorticoid activity.

These studies examine the activity of PF670462 in BEAS-2B cells that have been infected by rhinovirus (RV16) and confirm that the actions of this compound are not virus type specific and therefore that TGFβ is likely to be broadly involved in viral and non-viral mechanism of glucocorticoid resistance. The inventors have exemplified the action of the compounds on resistance in this study using glucocorticoid-inducible leucine zipper protein gene (GILZ) expression, as this gene is known to be regulated by GRE in the GILZ promoter, it is therefore useful in ascertaining GC activity in human airways and is accorded an important role in the anti-inflammatory actions of GC.

Example 6

These studies evidence the utility of PF670462 in treatment of acute viral respiratory illness.

Experiments in the current Example, Example 7 and 11 to 13 were conducted using intranasal insufflation of virus (2 million virions) administered in 35 microlitres of culture medium to lightly anaesthetized mice which were then treated with drugs as described and killed on day 5 for harvest of tissues and cells.

Figure 7:
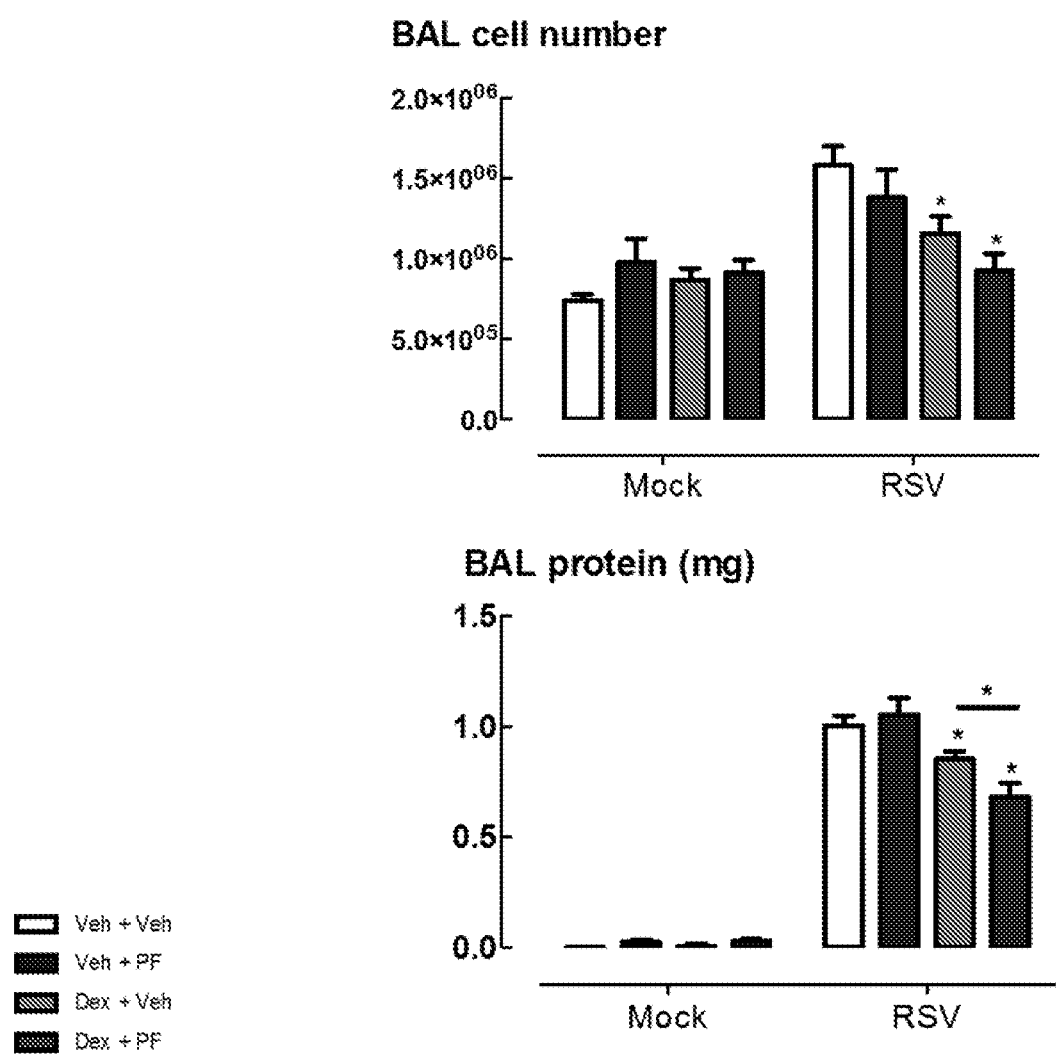
FIG. 7 Evidences the potential utility of PF670462 in treatment of acute viral respiratory illness. It is an in vivo experiment in female Balb/C mice that were inoculated with RSV, treated from day 1 with glucocorticoid and treated on days 3, 4 and 5 with PF670462 30 mg/kg (being the last 48 hours before post mortem). In this format, PF670462 alone had no effect on bronchoalveolar lavage fluid (BALF) protein or cellular content, Dexamethasone (Dex) 1 mgk/kg (i.p.)/day alone had little effect on protein or cell numbers, but the combination significantly reduced BALF cell and protein content.

An in vivo experiment was conducted in female Balb/C mice that were inoculated with RSV, treated from day 1 with glucocorticoid and treated on days 3, 4 and 5 with PF670462 30 mg/kg (being the last 48 hours before post mortem). In this format, PF670462 alone had no effect on bronchoalveolar lavage fluid (BALF) protein or cellular content, Dexamethasone (Dex) 1 mg/kg (i.p.)/day alone had little effect on protein levels and cell numbers (indices of lung injury), but the combination significantly reduced BALF cell and protein content (FIG. 7).

The changes in protein into the airspaces can be assessed by measuring the protein content of the BAL fluid. The leakage of protein normally reflects plasma leakage from inflamed blood vessels, its accumulation in the interstitium and subsequently passage through a compromised epithelial barrier. Thus, increased BAL protein is a sign of injury and its reduction, suggestive of protection.

BAL also contains cells, including those that are present under physiological circumstances (mainly macrophages) and those that are recruited following injury infection or allergic inflammation. The composition of the BAL cell infiltrate in these different types of inflammation varies, as it does over the time course of induction to the period of resolution.

Reductions in either or both of BAL cells and protein is considered to be evidence of a protective effect in various pulmonary pathologies.

Example 7

Figure 8A:
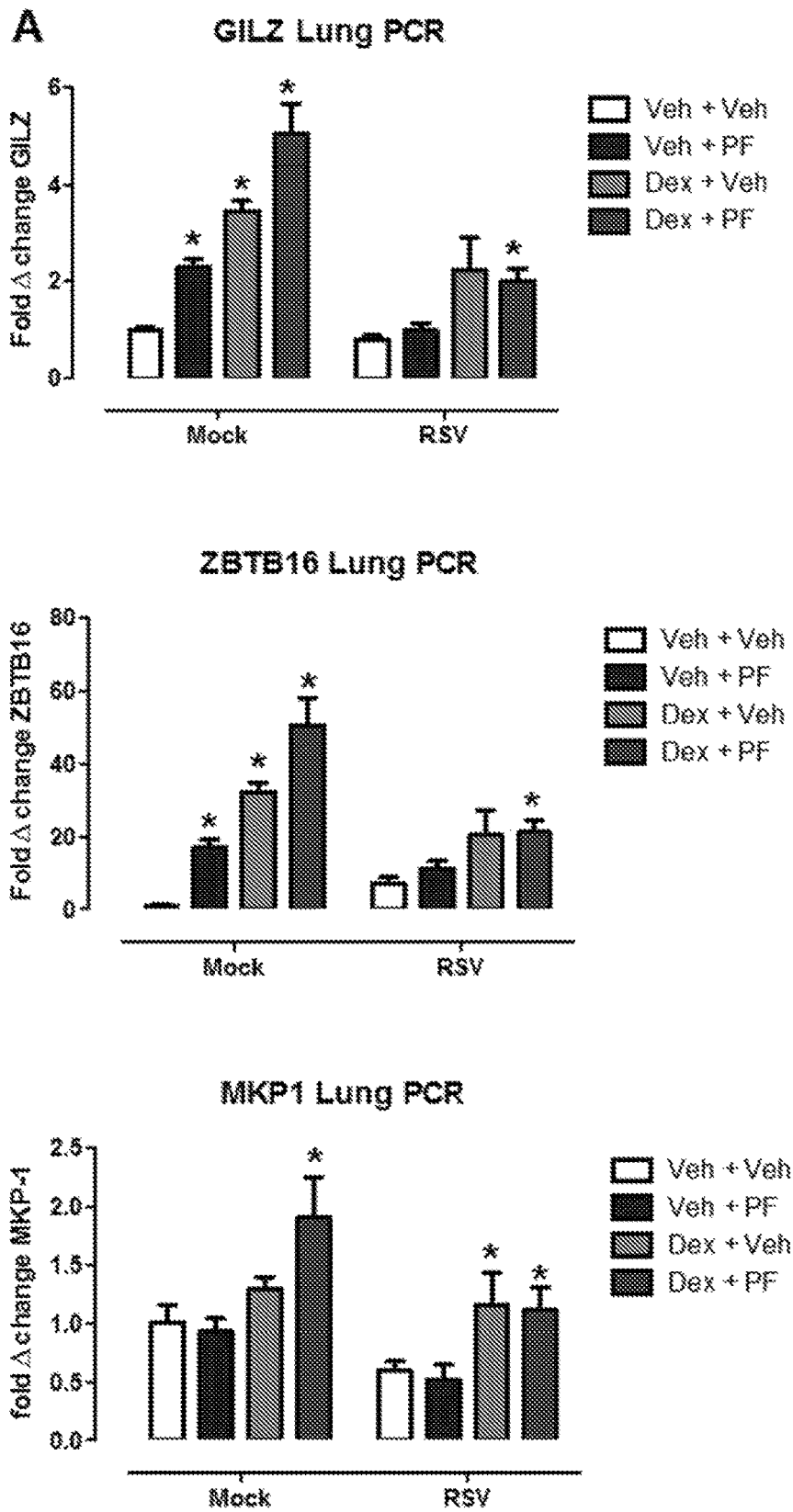
FIGS. 8A-8C RT-qPCR measurement of gene expression in lung tissue of mice from the experiment shown in FIG. 7 shows that the expression of the glucocorticoid inducible genes, GILZ, ZBTB16 and MKP1 was greater in the mice treated with PF670462 and Dex, than in those treated with either agent alone, following exposure to the same volume of conditioned medium that was used to administer the viral infection ('mock').
Figure 8B:
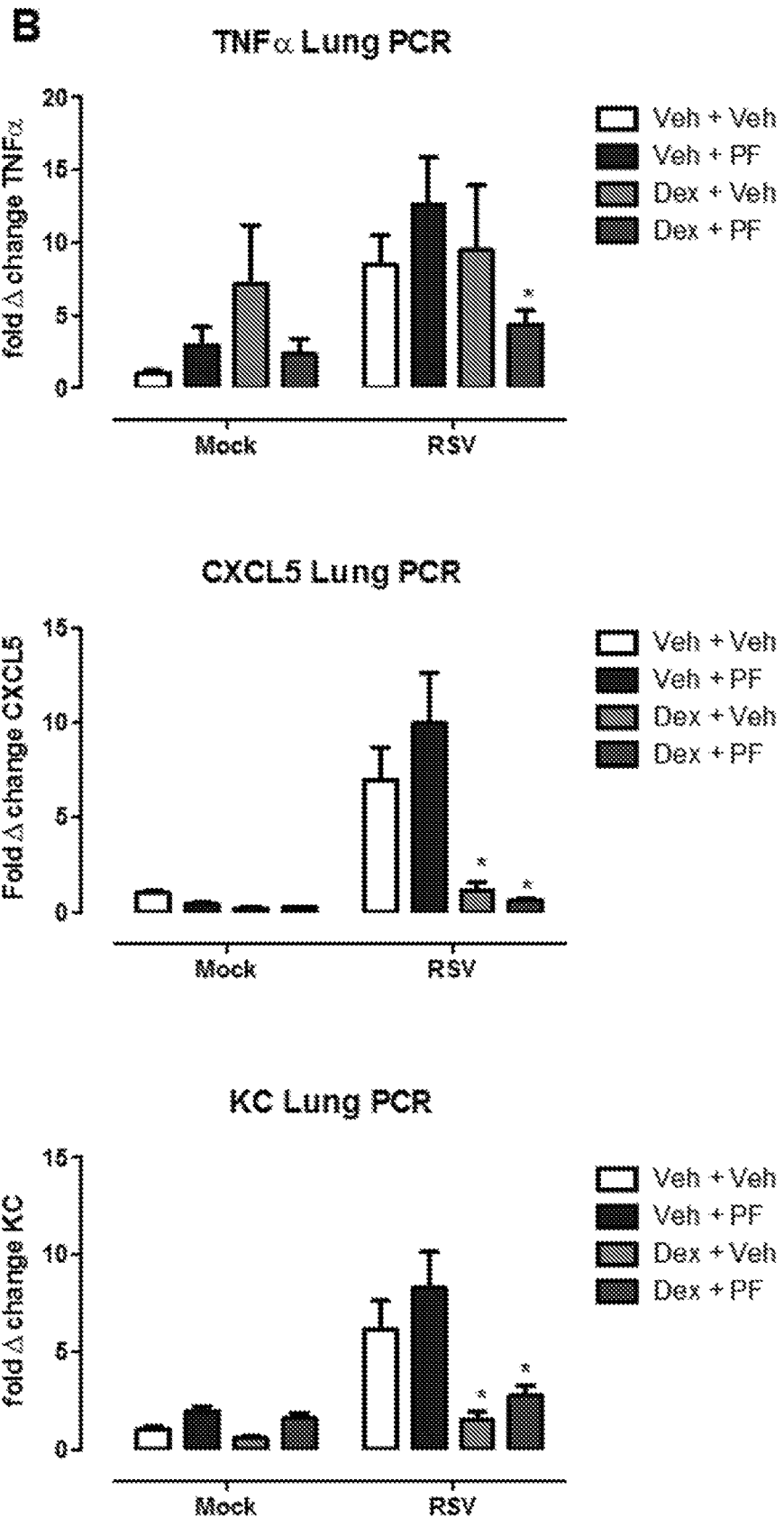
Figure 8C:
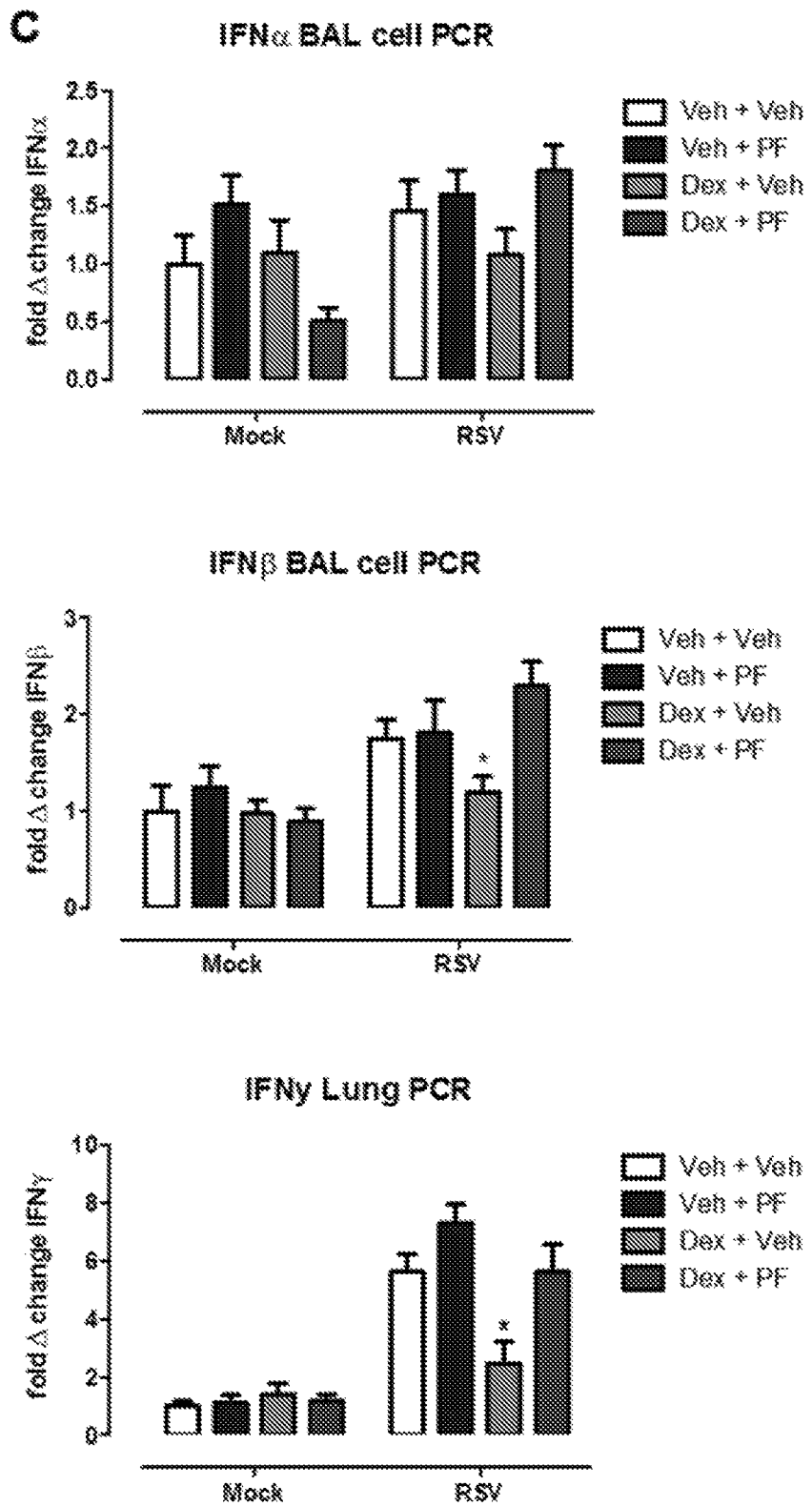
Figure 9:
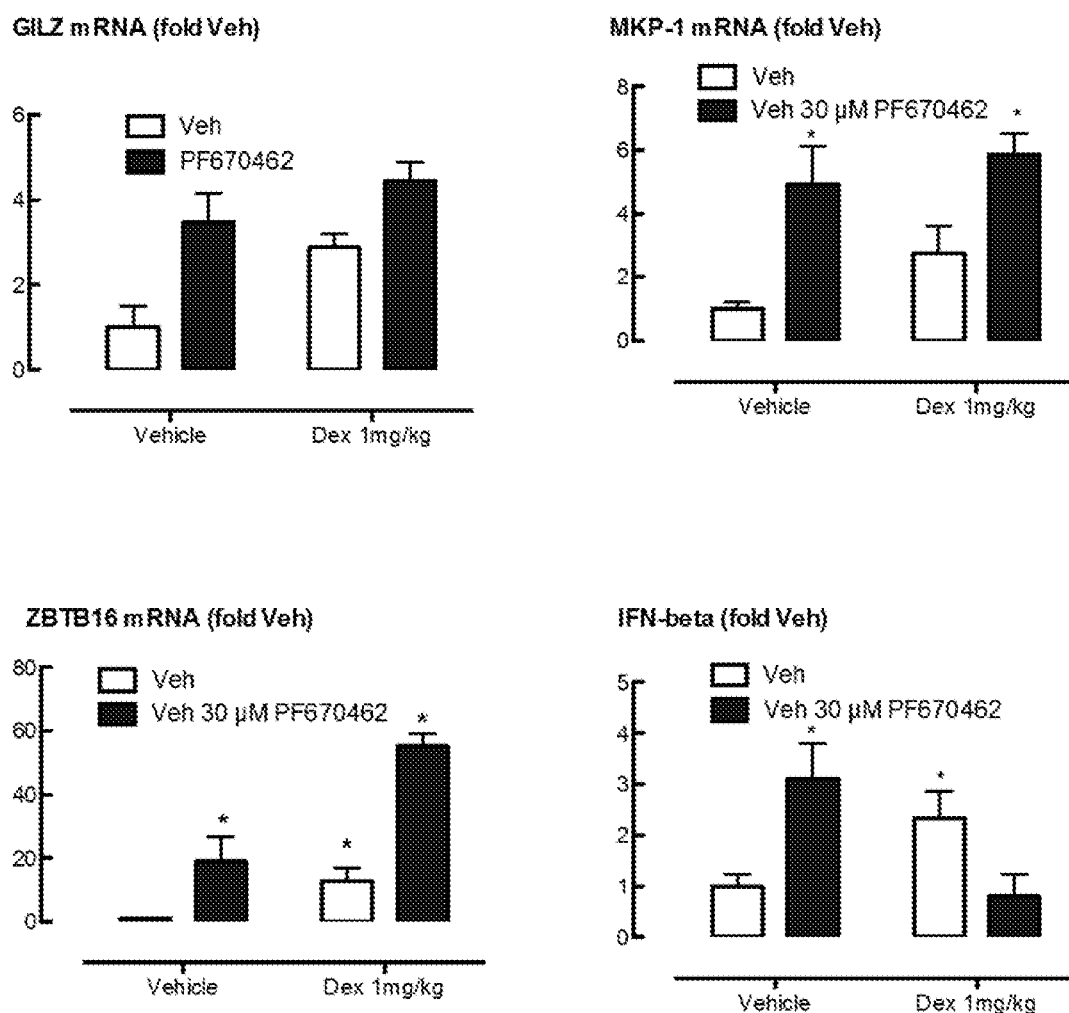
FIG. 9 The effect of two doses of topical PF670462 (0.6 µg, intranasal) 4 and 24 hours before post mortem in female Balb/c naïve mice receiving Vehicle (Veh) or Dex (1 mg/kg, ip) 4 hours before post mortem. Lung tissue was subjected RNA extraction after bronchoalveolar lavage and RT-qPCR was used to determine the levels of expression of GILZ, MKP-1, ZBTB16 and interferon β. *$P<0.05$. cf Veh/Veh group.

RT-qPCR measurement of gene expression in lung tissue of mice from the experiment shown in Example 6/FIG. 7 shows that the expression of the glucocorticoid inducible genes, GILZ, ZBTB16 and MKP1 was greater in the mice treated with PF670462 and Dex, than in those treated with either agent alone, following exposure to the same volume of conditioned medium that was used to administer the viral infection ('mock'). FIG. 8B shows the expression of genes that are controlled by Dex to varying degrees during RSV infection. FIG. 8C shows interferon expression in bronchoalveolar lavage cells and lung tissue. Each of the interferons declines in expression with Dex and is restored by combined treatment with PF670462.

This example shows related gene expression measurements in lung tissue from mice of the experiment described in Example 6. The genes shown in FIG. 8a are known to contain GRE regulatory elements in the promoter pro-inflammatory and they are increased in response to Dex treatment. The responses in these mice are potentially influenced by their exposure to Hep2 cell culture supernatants that comprise the Mock Vehicle for the RSV administration and are therefore used as mock control. Such supernatants are pro-inflammatory. Nevertheless, the inventors show that PF670462 administered by ip injection directly stimulates expression of ZBTB16, GILZ and MKP1, as does Dex and the combination has greater effect than does Dex alone, with the synergy being evident for regulation of MKP1 in which neither Dex nor PF670462 alone increased expression, but the combination had a significant effect in Mock-treated mice. RSV infection blunts the expression and the interaction at the time-point chosen for measurement. In 8B it is observed that PF670462 has no effect alone on TNFα, CXCL5 or KC, these being inflammatory and chemoattractant cytokines that recruit neutrophils to the lung and activate them, resulting in lung damage if such activation is protracted. The combination of Dex and PF670462 reduces TNFα, whereas neither compound alone had an effect. The profound reduction achieved by Dex alone in the expression of CXCL5 and KC is maintained in Dex plus PF670462-treated mice. In 8C we show the pattern of expression of selected important anti-viral genes, IFNα, IFNβ and IFNγ. The reduction in IFN expression induced by Dex in RSV treated mice is prevented by PF670462.

Example 8

The effect of two doses of topical PF670462 (0.6 μg, intranasal) 4 and 24 hours before post mortem in female Balb/c naïve mice receiving Dex (1 mg/kg, ip) 4 hours before post mortem. Lung tissue was subjected to RNA extraction after bronchoalveolar lavage and RT-qPCR was used to determine the levels of expression of GILZ, MKP-1, ZBTB16 and interferon β.

In this experiment in naïve Balb/C female mice (n=3 per group), the inventors examined the effects of PF670462 (30 μM) by the topical route applying the compound in 50 microlitres (ie 0.6 μg) to the nose of sedated mice, the dose being insufflated by nasal reflex to achieve distribution to the airway and lung surface. Several GC responsive genes were measured 4 hours after a systemic dose of maximally effective dose of Dex (1 mg/kg, ip), as was interferons. The direct stimulatory effect on the GC responsive genes may reflect enhancement of the regulatory effects of corticosterone, the endogenous murine glucocorticoid.

Example 9

Experiments described in the current Example and Example 14 involved culture of human parenchymal fibroblasts, measurement of their proliferation and gene expression response, the methods for which are detailed in Schuliga et al 2009 (Am J Respir Cell Mol Biol. 2009; 41(6): 731-41).

Interaction between TGFβ and bFGF in human lung fibroblasts. SB431542 or PF4800567 was added 30 min before TGFβ which was added simultaneously with bFGF and incubation continued for 48 h, at which time viable cell number was determined.

Experiments were conducted in lung fibroblasts from donors without IPF, contrasting the effects of the ALK5 inhibitor SB431542 with those of the CK1ε (epsilon) selective inhibitor PF4800567. An interaction previously characterized in airway smooth muscle cultures is that TGFβ reduces the proliferative effects of bFGF. A similar finding is observed in human lung fibroblasts, whereby TGFβ reduces the bFGF mitogenic effects. Treatment with SB431542 is able to block the effect of TGFβ and restore the mitogenesis of bFGF (FIG. 10). However, PF4800567 1.0 μM reduced the bFGF induced mitogenesis directly and this remained suppressed in the presence of TGFβ.

Example 10

FIG. 11A-D shows data from a series of experiments using siRNA against either CK1δ (delta) or CK1ε (epsilon) or their combined effects. It is evident that knockdown of CK1ε was more efficient than that for CK1δ. Thus, the data may not reveal the full extent of the role of these two CK1 isoforms in the action of TGFβ on GC responses. At TGFβ 40 μM ZBTB16 and SCNN1a expression are restored, whereas GILZ is not. Heme oxygenase-1 which has anti-oxidant effects, is down regulated by Dex, an effect of Dex and glucocortcoids more generally that may be considered deleterious to lung health. The siRNA against CK1δ/ε restored and enhanced HO-1 expression. The expression of the MAPK phosphatase-1 (MKP-1) enzyme is not affected by either TGFβ1 or by the siRNA combinations. MKP-1 by deactivating MAPK-dependent pathways leading to cytokine expression may limit lung injury, but also has the potential to impair lung host defence.

Example 11

Figure 12:
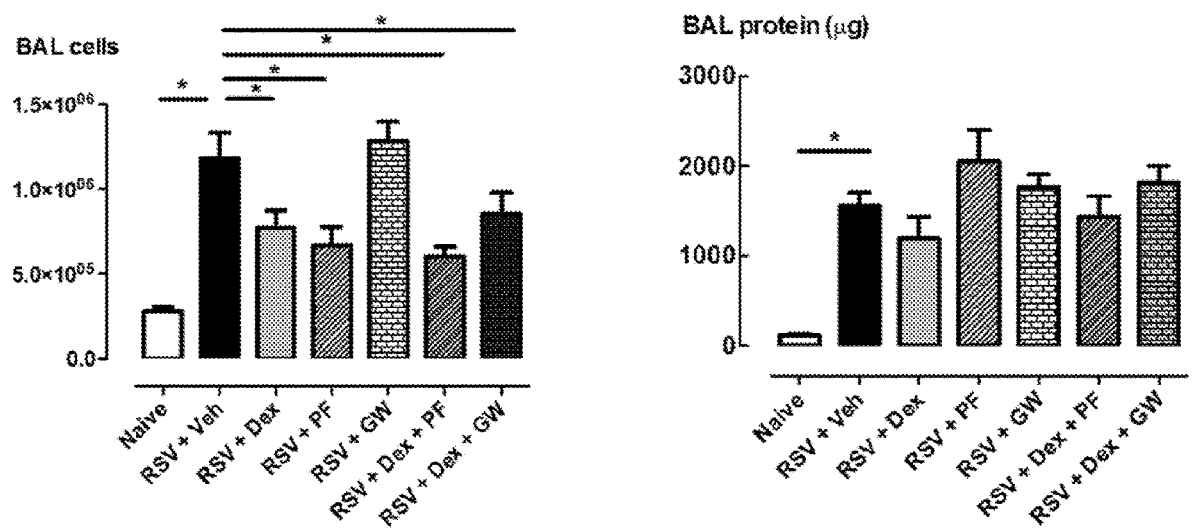
FIG. 12 In a 5 day model of RSV infection, distinguished from the study in FIGS. 7 and 8 by Dex, the TGFβ receptor kinase inhibitor, GW788388 and PF670462 being administered from day 1.

FIG. 12 shows, in a 5 day model of RSV infection and distinguished from the study in described in Example 6 and results shown in FIGS. 7 and 8 by Dex, the TGFβ receptor kinase inhibitor, GW788388 and PF670462 being administered from day 1. Either of Dex or PF670462 treatments reduced the accumulation of inflammatory cells in the BAL fluid. The combination was equally effective. None of the treatments altered BAL cell protein levels. GW788388 had no activity.

These data suggest that PF670462 has a similar ceiling effectiveness in regulating RSV infection induced inflammation to Dex and is superior to the global blockade of TGFβ signaling by the ALK5 inhibitor, GW788388.

Example 12

Figure 13:
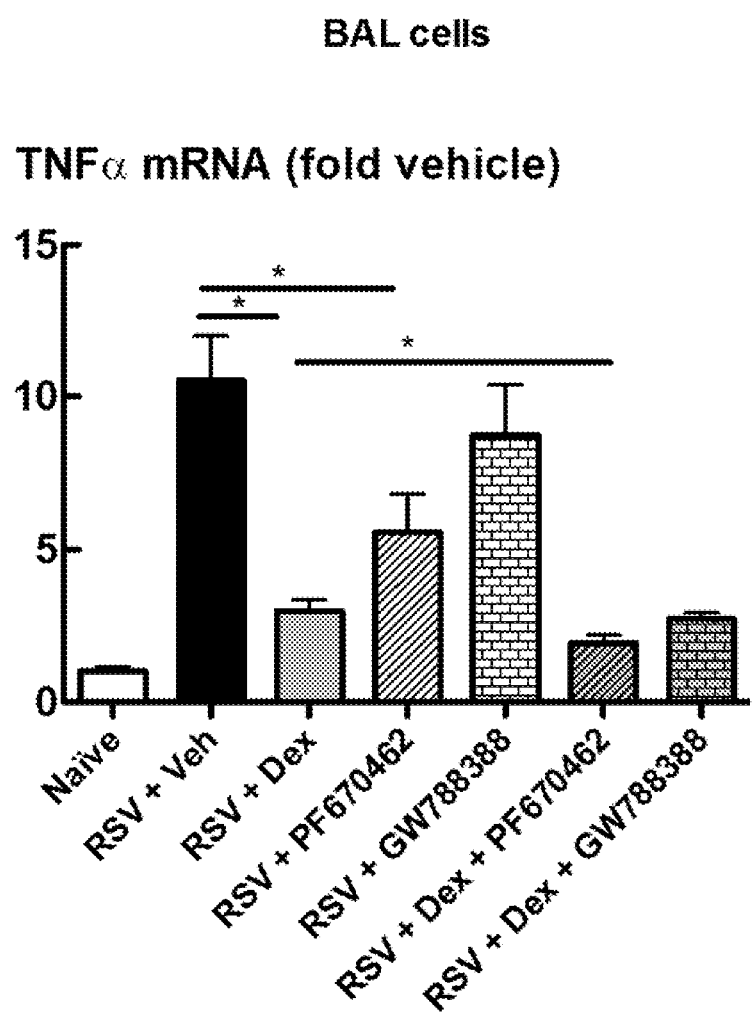
FIG. 13 Gene expression in BAL cells from the RSV experiment shown in FIG. 12, of TNFα mRNA levels.

FIG. 13 shows the gene expression in BAL cells from the RSV experiment described in Example 11 and FIG. 12 which indicate that either Dex or PF670462 but not GW788388 directly suppresses TNFα expression levels. PF670462, but not GW788388 had a further effect on TNFα expression when added to Dex treatment.

These observations provide evidence of an interaction between PF670462 and Dex to achieve greater control of the inflammatory mediators IL-6 and TNFα.

Example 13

Figure 14:
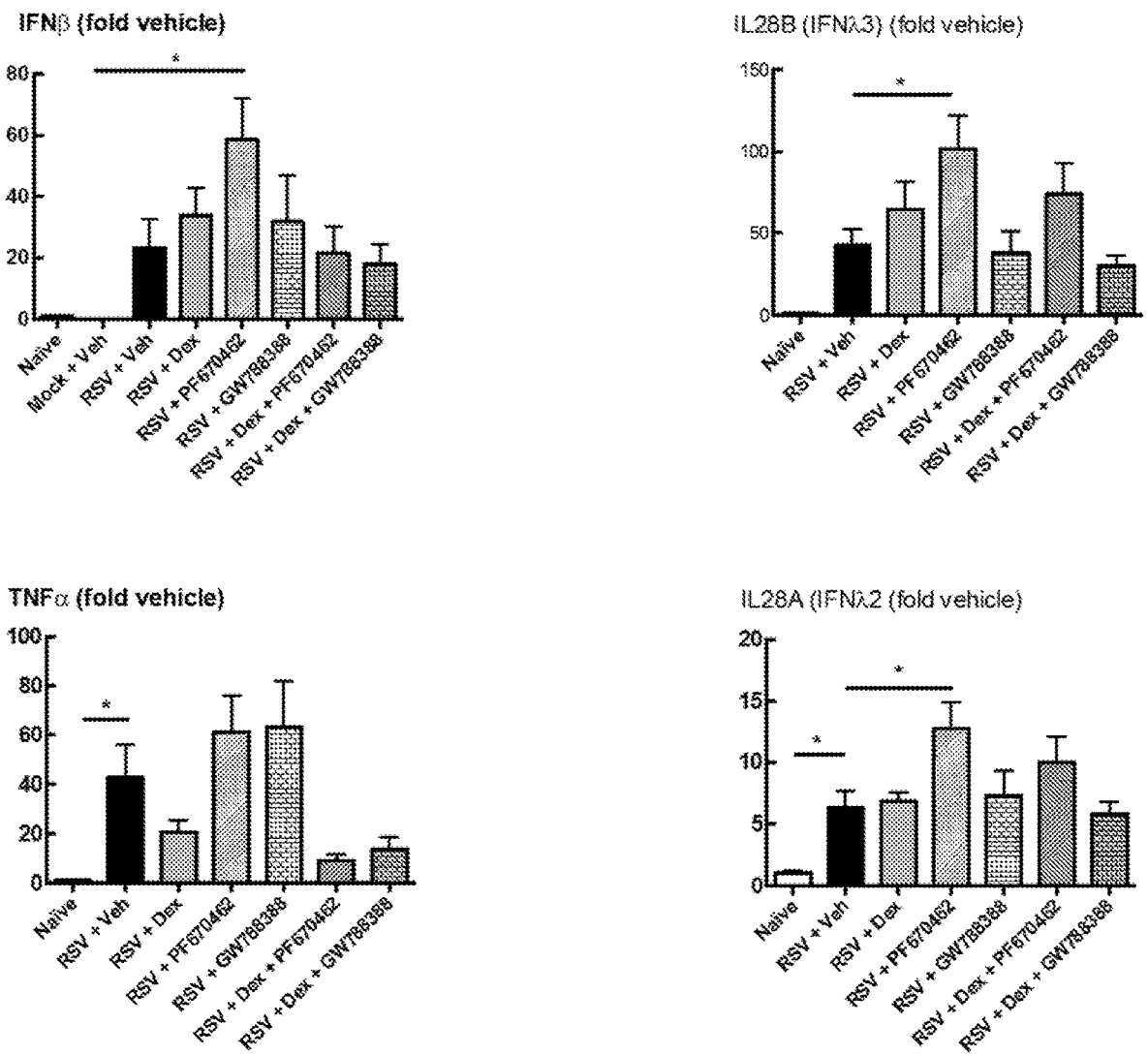
FIG. 14 Levels of IFNβ, λ2, λ3 and TNFα in the 5 day model of FIG. 12.

Levels of IFN β, λ 2 and 3 were enhanced by PF670462 but not by Dex nor GW788388 (FIG. 14) in the 5 day model of RSV infection described above. Enhancement of interferon production by PF670462 may be expected to limit the duration of RSV infection by enhancing anti-viral activity in the airway.

Example 14

The investigation of fibrogenesis may be undertaken in in vivo models typically using rodents. However, differences in behavior of cell types and species differences in protein structures and signaling systems create some limitations in the predictive value of such models. Additional valuable evidence of impacts on fibrogenesis can be obtained from the use of human fibroblasts isolated from the parenchyma and maintained in cell culture (Schuliga et al. (2009) Am J Respir Cell Mol Biol 41(6):731-741; Westergren-Thorsson et al. (2004) Int J Biochem Cell Biol 36(8): 1573-1584).

Figure 15A:
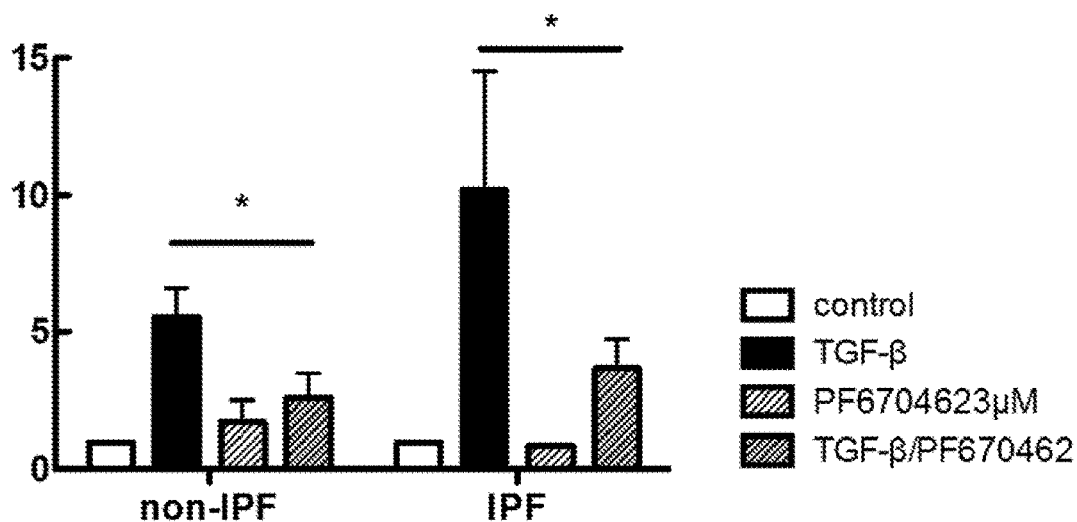
FIGS. 15A-15C Further evaluation of anti-fibrotic effects carried out in industry standard bleomycin 5 day model of RSV infection.

FIG. 15A shows the expression of collagen 1A at baseline (control) and in response to a 24 hour incubation with TGFβ 40 μM. The data shown is for parenchymal lung fibroblasts from both patients with the pulmonary fibrotic disease, idiopathic pulmonary fibrosis (IPF) and those derived samples of non-IPF donors. PF67462 (3 μM) significantly suppressed induction of Col1a in fibroblast cultures, regardless of their origin. Col1a is a subunit of the fibrillar type collagen that is deposited in excess in the extracellular matrix in fibrotic lesions.

Figure 15B:
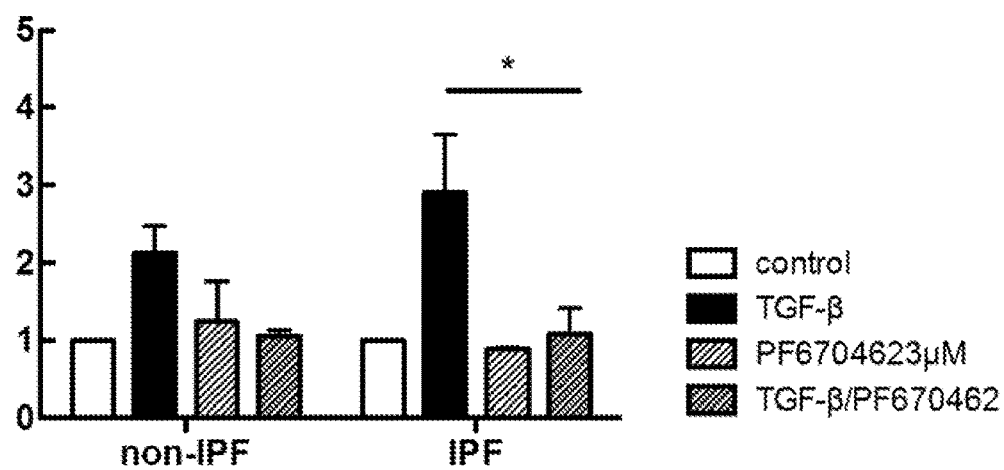

FIG. 15B was performed in the same manner as for FIG. 15A except that in this experiment the fibroblasts are cultured as a suspended spheroid, rather than in 2D monolayer culture. The PF670462 compound also inhibits TGFβ in IPF but the smaller increase in non-IPF derived cultures is not signficantly affected by PF670462 (3 μM).

Figure 15C:
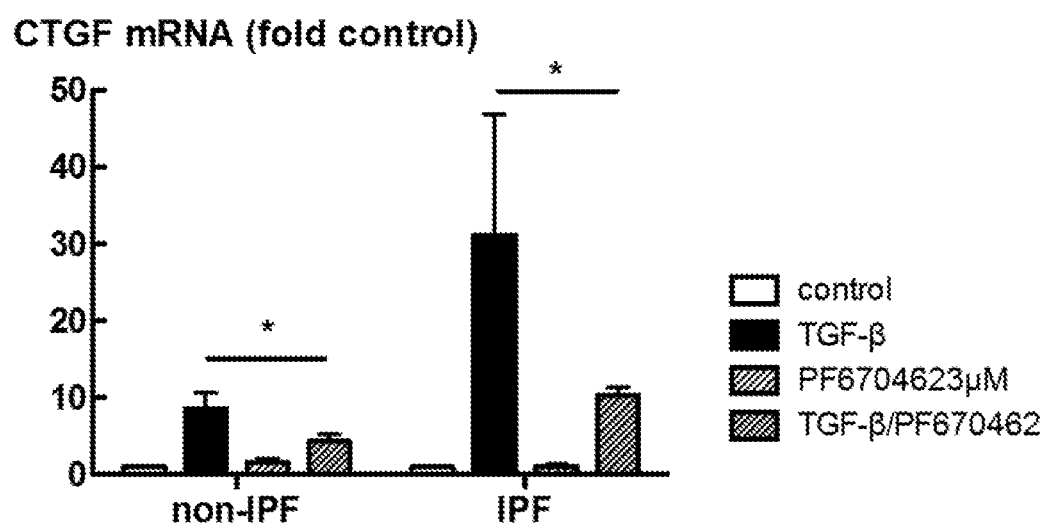

FIG. 15C shows the results of measurement of TGFβ-induced expression of CTGF in the same experiment as reported in FIG. 15A.

The observations in FIGS. 15A-C collectively indicate that the fibrogenic actions of TGFβ are inhibited by PF670462 in human parenchymal fibroblasts, regardless of whether these are from IPF or non-IPF donors, or whether they are cultured in 2D or 3D.

Example 15

Bleomycin is commonly used in mice to model pulmonary fibrosis. This anti-cancer agent is known to induce pulmonary fibrosis in a subset of patients. The mouse model shows an initial lung injury followed by a repair that causes extensive fibrotic lesions (Langenbach et al. (2007) Can J Pharmacol. 85(7):727-738). Eventually the intensity of the fibrosis declines but never fully resolves. Early treatment in the model (during the first 3 days) may influence the outcome via anti-inflammatory effects (Limjunyawong et al. (2014) Physiol Rep. 2(2): e00249). Delayed treatment is used to specifically examine impact on the fibrogenic process.

The bleomycin experiments conducted in the current Example and Examples 16 to 18 were according to methods detailed in Langenbach et al 2007 (Canadian Journal of Pharmacology and Physiology, 85(7):727-38), with drug treatment regimens as described in the Examples and figure legends.

Figure 16:
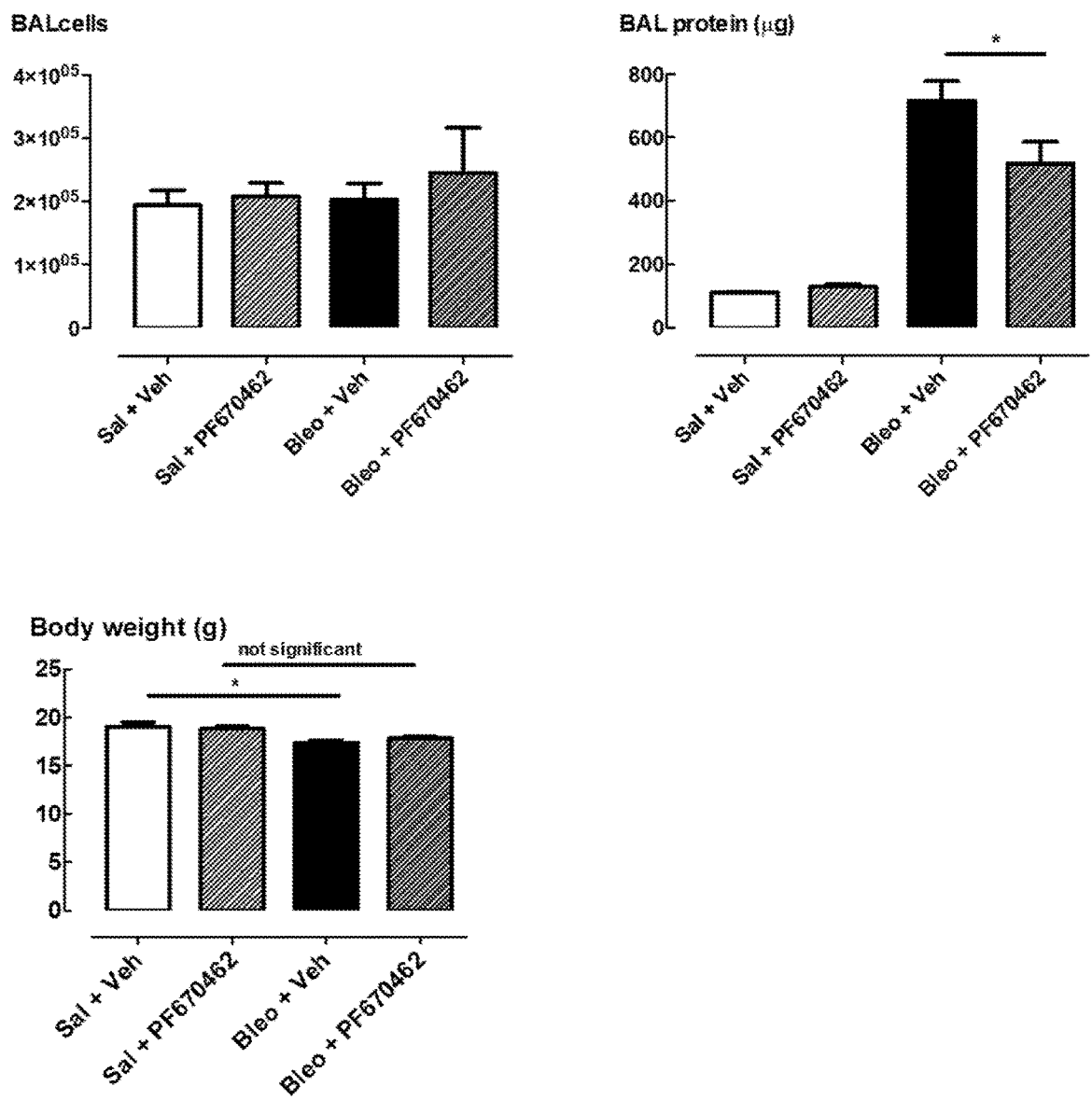
FIG. 16 shows a 3-day balb/c bleomycin experiment. Female mice were treated with bleomycin (105 milli Units) on day 0 and treatment with PF670462 occurred once daily by intraperitoneal injection of a single dose of 30 mg/kg. The following were investigated: BAL cells and BAL protein levels.

FIG. 16 shows a 3-day bleomycin experiment. Female mice were treated with bleomycin (105 milli Units) on day 0 and treatment with PF670462 occurred once daily by intraperitoneal injection of a single dose of 30 mg/kg. Bronchoalveolar lavage (BAL) protein, but not cells, were increased at this early time-point. PF670462 significantly reduced BAL protein levels. During the 3 day treatment period body weight decreased in vehicle-treated mice but not in those treated with PF670462. The body weight of the bleomycin vehicle treated mice and the bleomycin PF670462 treated mice were not statistically different, suggesting that the difference in BAL protein in PF670462 treated mice compared to vehicle was not due to a loss of body weight.

Figure 17:
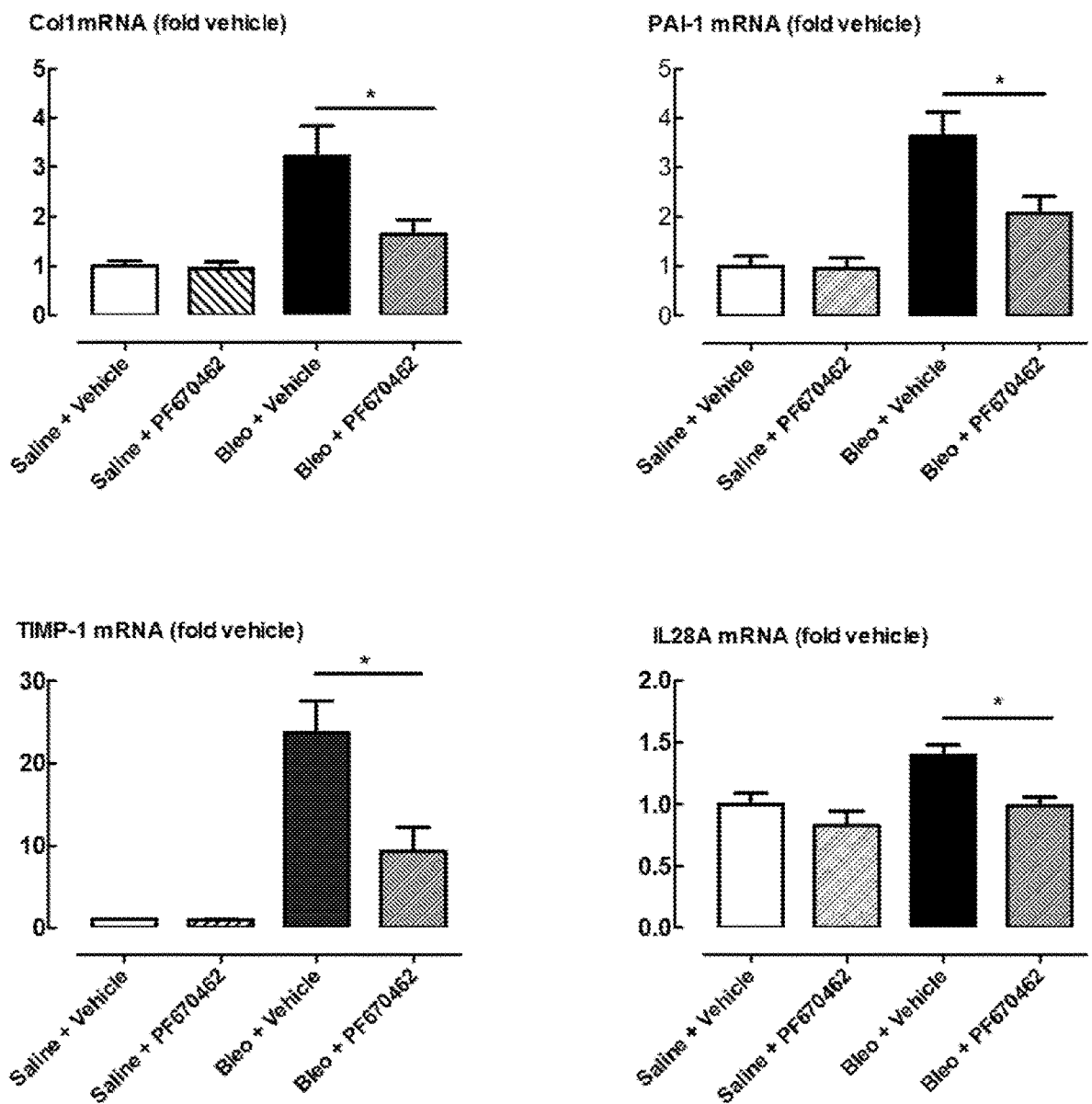
FIG. 17 shows gene expression changes in the lung tissue of mice form the experiment described in FIG. 16, showing Col1 mRNA, PAL-1 mRNA, TIMP1 mRNA and IL-28A mRNA.

FIG. 17 shows gene expression changes in the lung tissue of mice from the experiment described above in and shown in FIG. 16. Bleomycin induction of Col1a, CTGF, PAI-1 and TIMP1 was significantly reduced by PF670462. As outlined above, collagen 1a (Col1a) is a subunit of the fibrillar type collagen that is deposited in excess in the extracellular matrix in fibrotic lesions, connective tissue growth factor is a fibrogen that stimulates collagen deposition, and PAI-1 increases the fibrotic lesion by facilitating the accumulation of fibrin in the airspaces thereby providing a provisional ECM for an invasive fibroplasia.

These findings suggest that PF670462 ameliorates lung damage induced by bleomycin, and that gene expression changes associated with fibrogenesis are strongly suppressed.

Example 16

Figure 18:
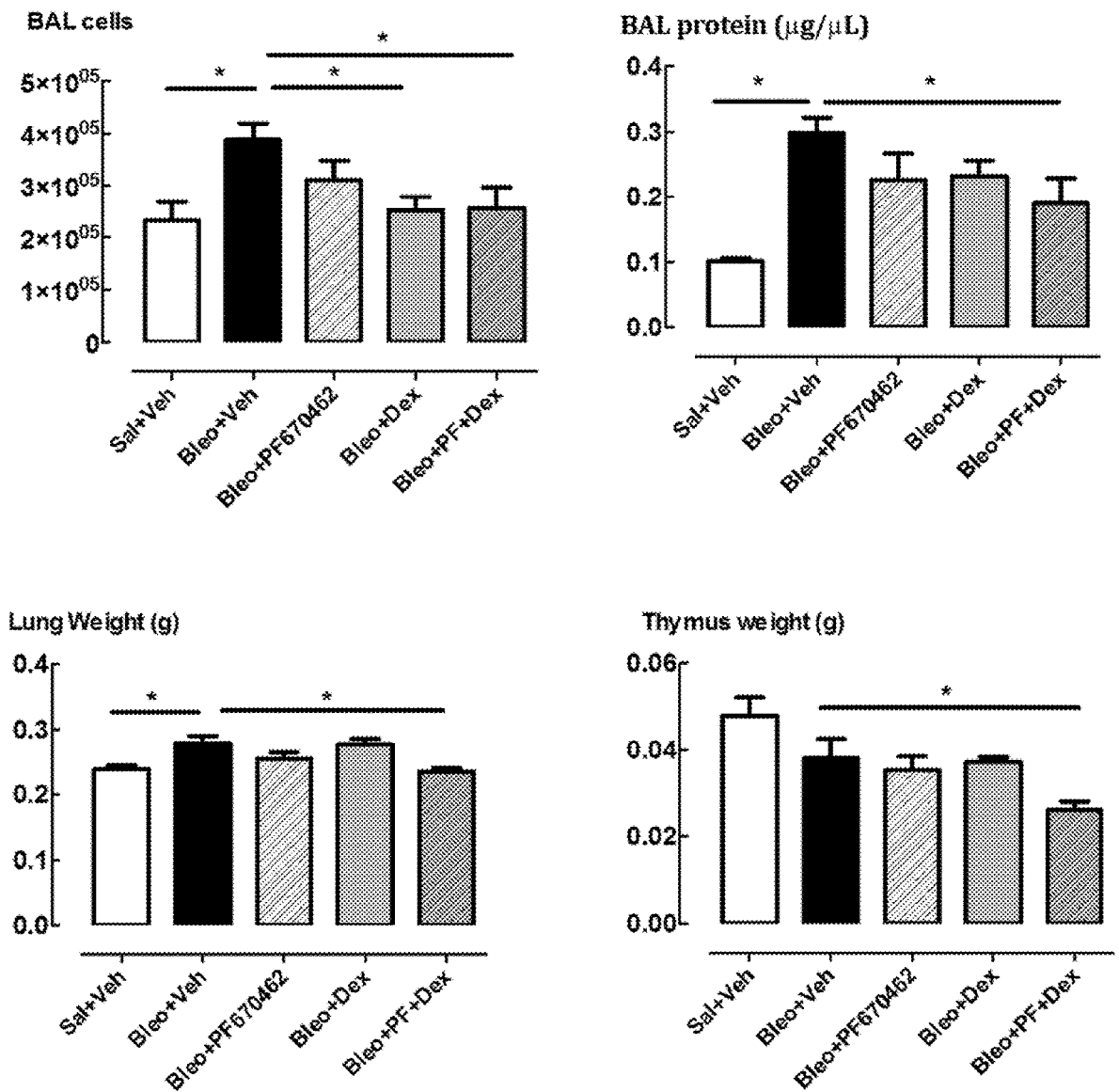
FIG. 18 shows a similar experiment to that of FIG. 16, except that male mice were used, and the following were investigated: lung weight, BAL cells, Thymus weight and spleen weight.
Figure 19:
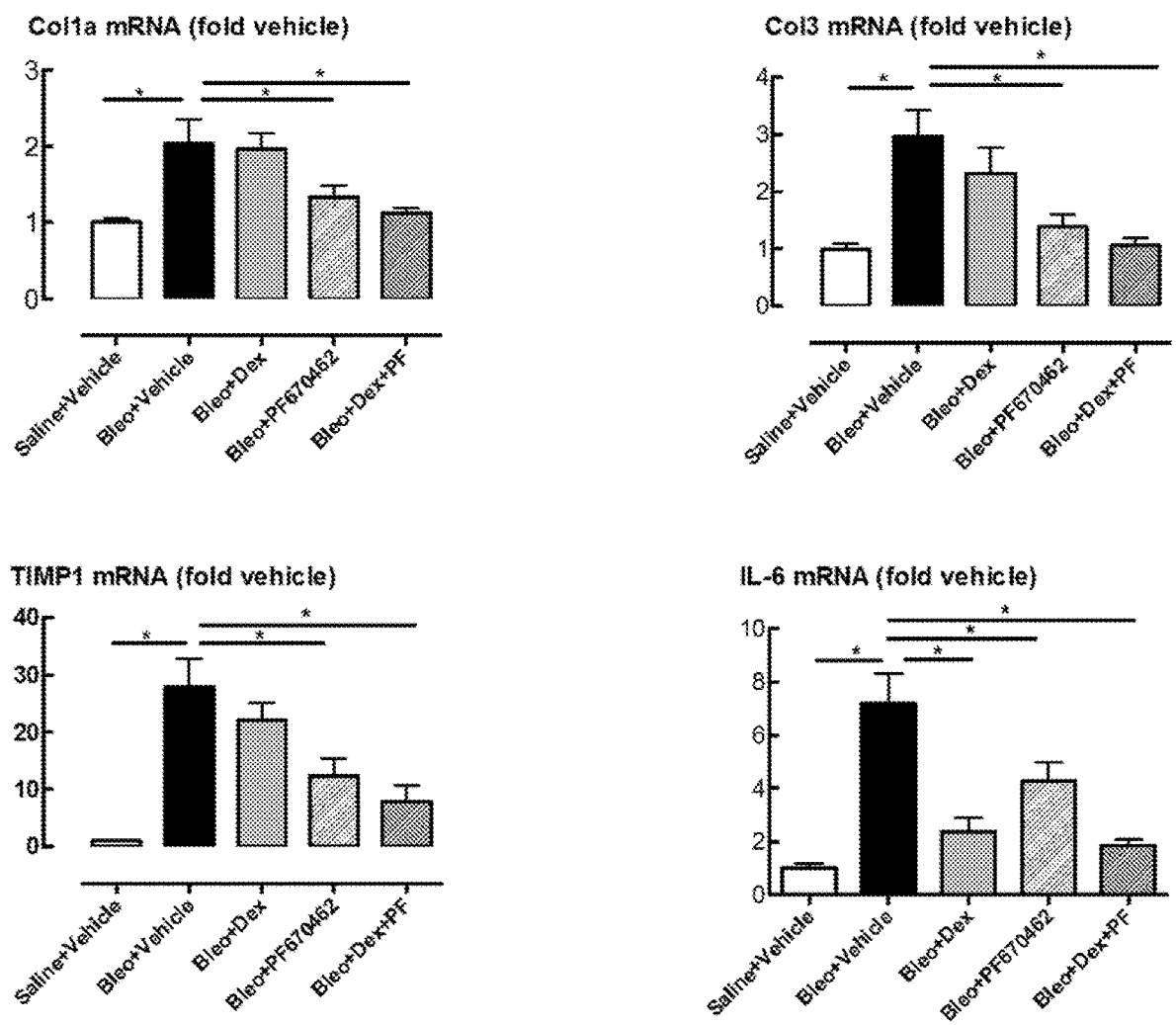
FIG. 19 shows gene expression changes in the lung tissue of mice form the experiment described in FIG. 18, showing Col1a mRNA, Col3 mRNA, TIMP1 mRNA and IL-6 mRNA.

FIGS. 18 and 19 show similar experiments to those in Example 15 above, except that male mice were used.

In FIG. 18, BAL cells were increased by bleomycin in vehicle-treated, but not in PF670462- or Dex-treated mice. The BAL cell number in mice treated with the combination of Dex and PF was significantly less than those in vehicle-treated mice. Moreover, lung weight and BAL protein increases in response to bleomycin were reduced by the combination of Dex/PF670462 as was thymus weight.

FIG. 19 shows gene expression of the male mouse experiment described above and shown in FIG. 18. Col1A, Col3 and TIMP1 were increased by bleomycin and reduced by PF670462, but not by Dex, whereas IL-6 increases in response to bleomycin were reduced by Dex, PF670462 and the combination.

The pattern of suppression of fibrogenic gene expression were similar in male and female mouse models.

Example 17

Figure 20:
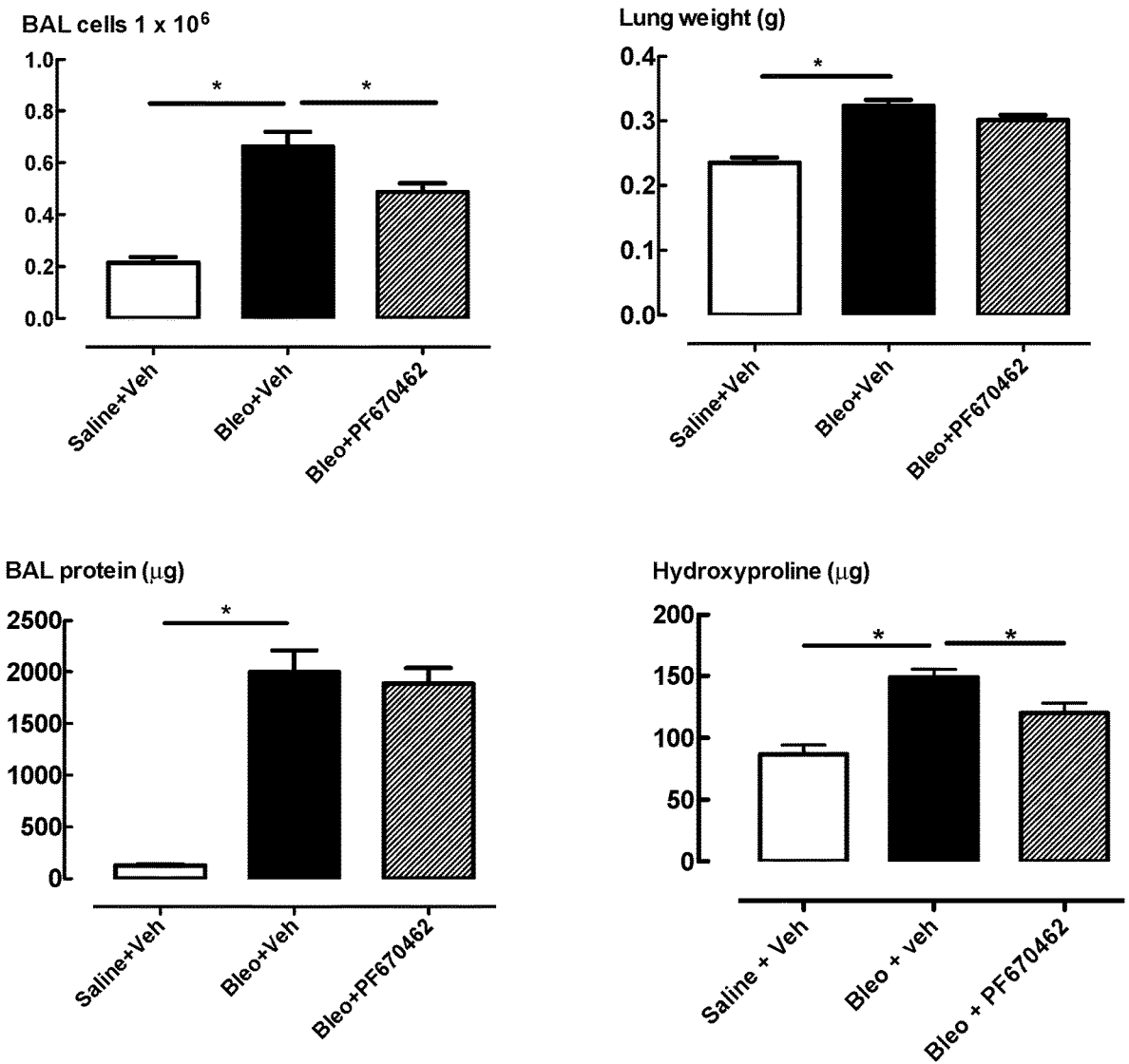
FIG. 20 shows data from a bleomycin experiment of longer duration (14 days) in which treatment with PF670462 was delayed until day 3, bleomycin having been administered on day 0. Measurements were made in terms of lung weight, BAL cells, Hyp Total dry weight and total BAL protein.

FIG. 20 shows data from a bleomycin experiment of longer duration (14 days) compared to that described in Examples 15 and 16 above in which treatment with PF670462 was delayed until day 3, bleomycin having been administered on day 0. The accumulation of cells on the BAL fluid, the wet weight of the lung and hydroxyproline content (an index of the tissue collagen content) were all significantly reduced by this delayed treatment with PF670462 (30 mg/kg/day) which concluded 24 hours prior to post mortem (day 13).

Example 18

Figure 21:
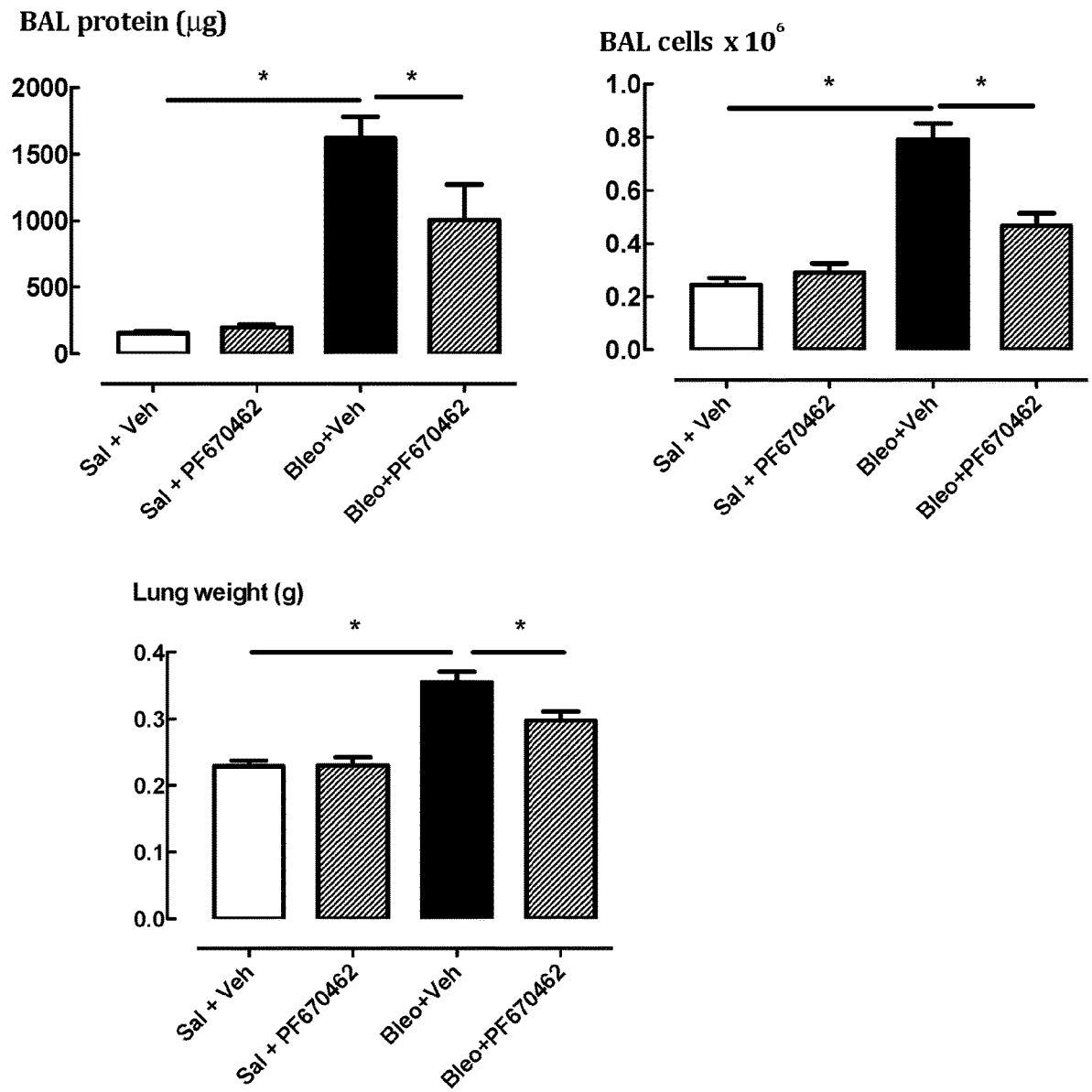
FIG. 21 shows the effects of PF670462 administered from day 8 until day 21 of a 21 day bleomycin experiment in female mice in terms of lung weight, BAL cells$\times 10^6$ and BAL protein.

FIG. 21 shows the effects of PF670462 administered from day 8 until day 21 of a 21 day bleomycin experiment in female mice. The accumulation of cells and protein in the BAL was significantly reduced by daily treatment with PF670462 as was the increase in lung wet weight.

Figure 22:
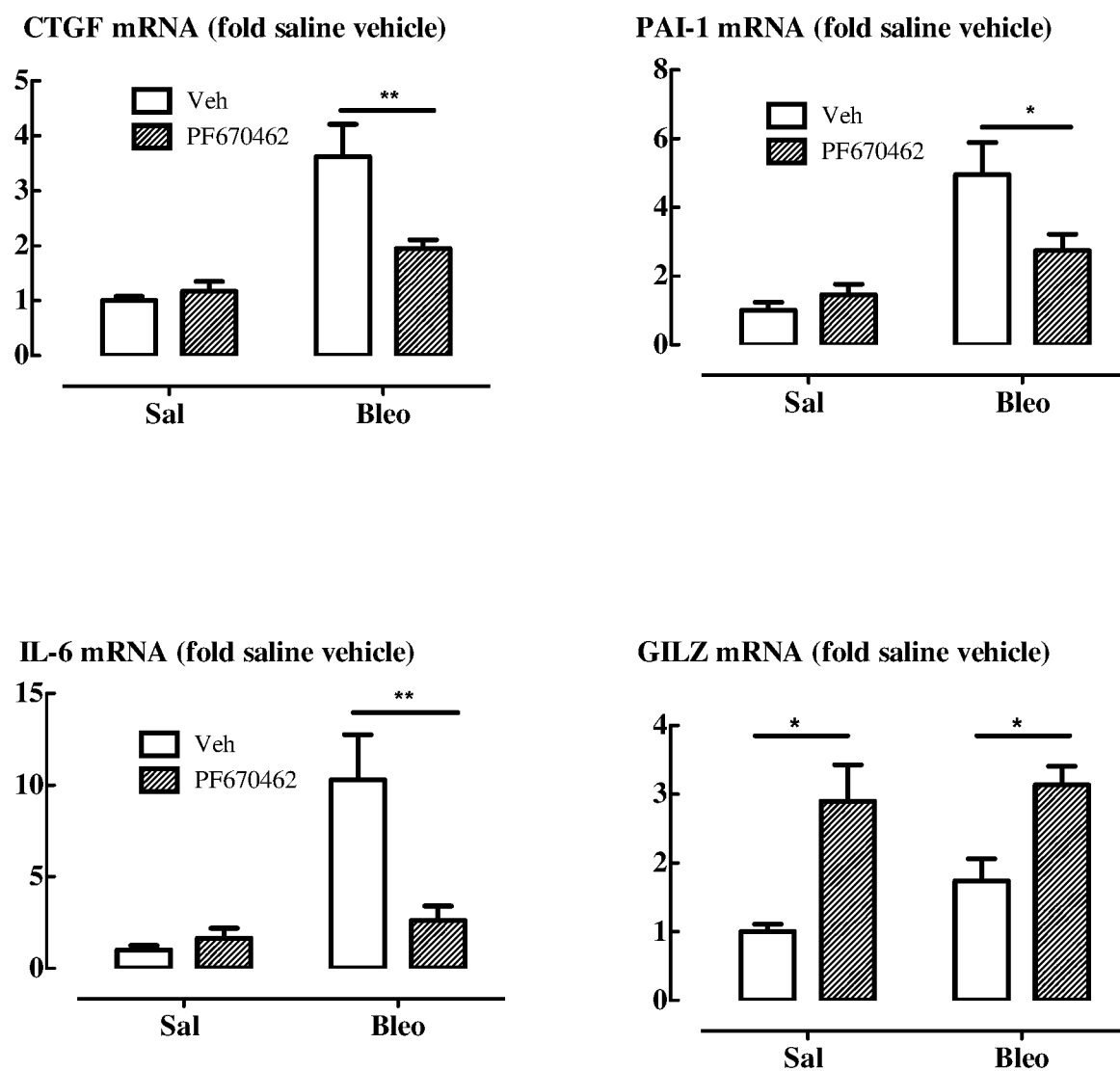
FIG. 22 shows the effects of PF670462 on gene expression in the lungs of mice from the experiment described in FIG. 21, showing the expression of the fibrogens CTGF, interleukin-6 (IL-6) and plasminogen activation inhibitor-1 (PAI-1) in the lung tissue.

FIG. 22 shows the effects of PF670462 on gene expression in the lungs of mice from the experiment described above in FIG. 21. The expression of the fibrogens CTGF and interleukin-6 (IL-6), as well as plasminogen activation inhibitor-1 (PAI-1) were significantly reduced in the lung tissue. The glucocorticoid regulated gene GILZ was induced by PF670462 equally in saline and bleomycin-treated mice.

The data in Examples 16 to 18 establish in 4 independent studies ranging in duration from 3 to 21 days and in both male and female mice that treatment with PF670462 (30 mg/kg/day, ip) is able to reduce fibrogenesis and does so by suppression of key fibrogenic gene expression. The evidence of efficacy contrasts with the lack of efficacy of the glucocorticoid, dexamethasone in this model. The evidence obtained in the 14 and 21 day experiments provides a consistent suite of findings indicating that a treatment protocol as opposed to the pretreatment protocols use in the 3 day studies, is effective in reducing lung fibrosis and the associated fibrogenic signals and further suggests that it is the suppression of the fibrogenic signals rather than the anti-inflammatory effect that underpins the ultimate suppression of lung fibrosis.

Example 19

The concentration response relationship of the impact of PF670462 on glucocorticoid activity has been investigated in the BEAS-2B cell line.

FIG. 23 shows the effects of increasing concentrations of PF670462 on budesonide and dexamethasone (1-100 nM) mediated activation of a GRE reporter construct transiently expressed in BEAS 2B cells. In this assay system the maximum effect, but not the potency of the glucocorticoid, is concentration dependently increased by PF670462 (0.3-10 µM).

Figure 24A:
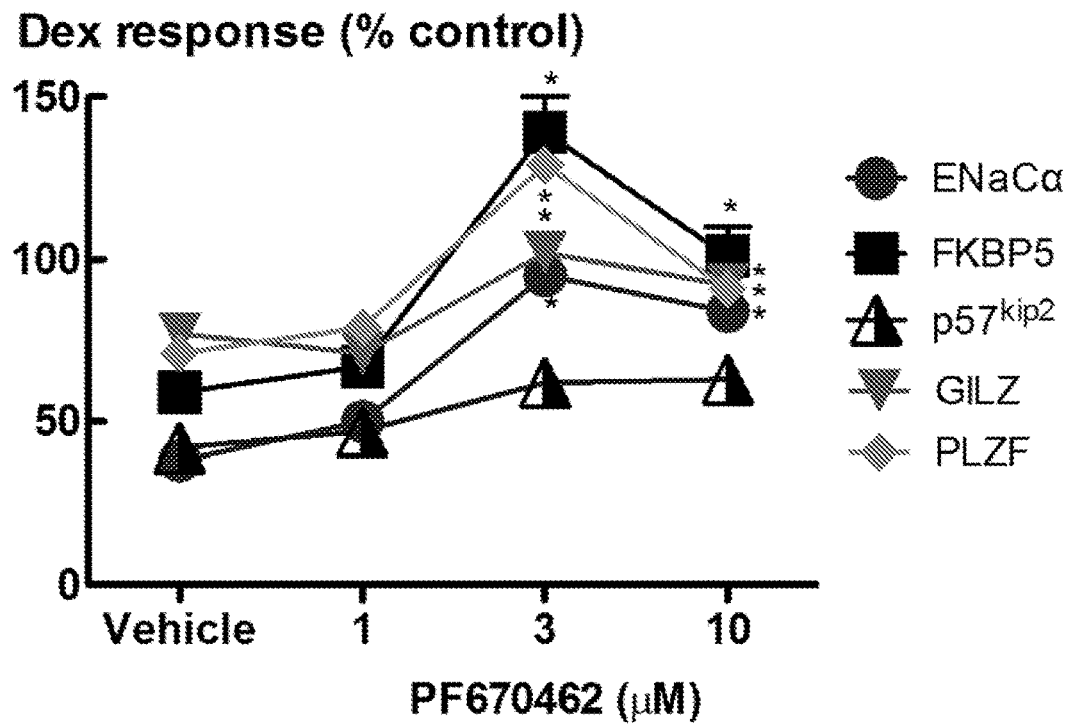
FIGS. 24A-24B show the concentration dependent effects of PF670462 (1-10 µM), on TGFβ suppression of the gene expression responses to Dex at an optimal concentration of 100 nM. Data was obtained using BEAS-2B cells.
Figure 24B:
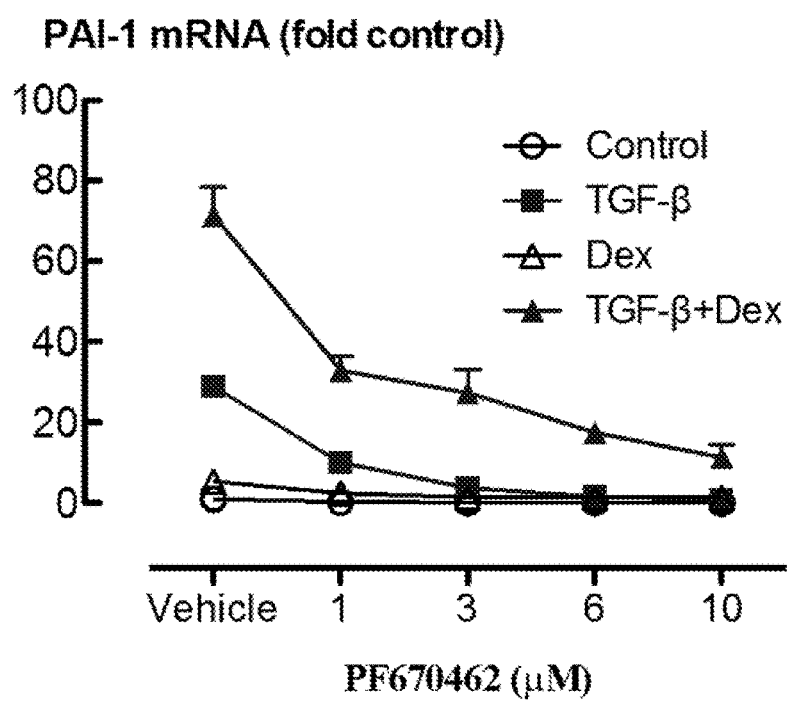

FIG. 24A show the concentration dependent effects of PF670462 on TGFβ suppression of the gene expression responses to Dex at an optimal concentration of 100 nM. TGFβ suppression ranged in magnitude amongst the genes selected for analysis. Thus, the TGFβ suppression of Dex-induced expression of GILZ, FKBP5, ZBTB16 (PLZF) and SCNNIA (ENaCα) expression is prevented by prior incubation with PF670462 (1-10 µM), whereas the suppression of CDKN1C (p57$^{kip2}$) is unaffected. TGFβ and Dex synergise in increasing the expression of PAI-1 (FIG. 24B). This increase in expression is concentration-dependently reduced by PF670462 (1-10 µM).

These sets of experiments indicate that PF670462 effects on glucocorticoid activity are concentration dependent, and that the action is not simply due to broad antagonism of the TGFβ signalling pathway as some effects of TGFβ, such as the suppression of glucocorticoid-induced CDKN1c (p57$^{kip2}$) expression are unaffected, whereas these effects are completely blocked by the ALK5 inhibitor, SB431542 (not shown).

Example 20

Figure 25:
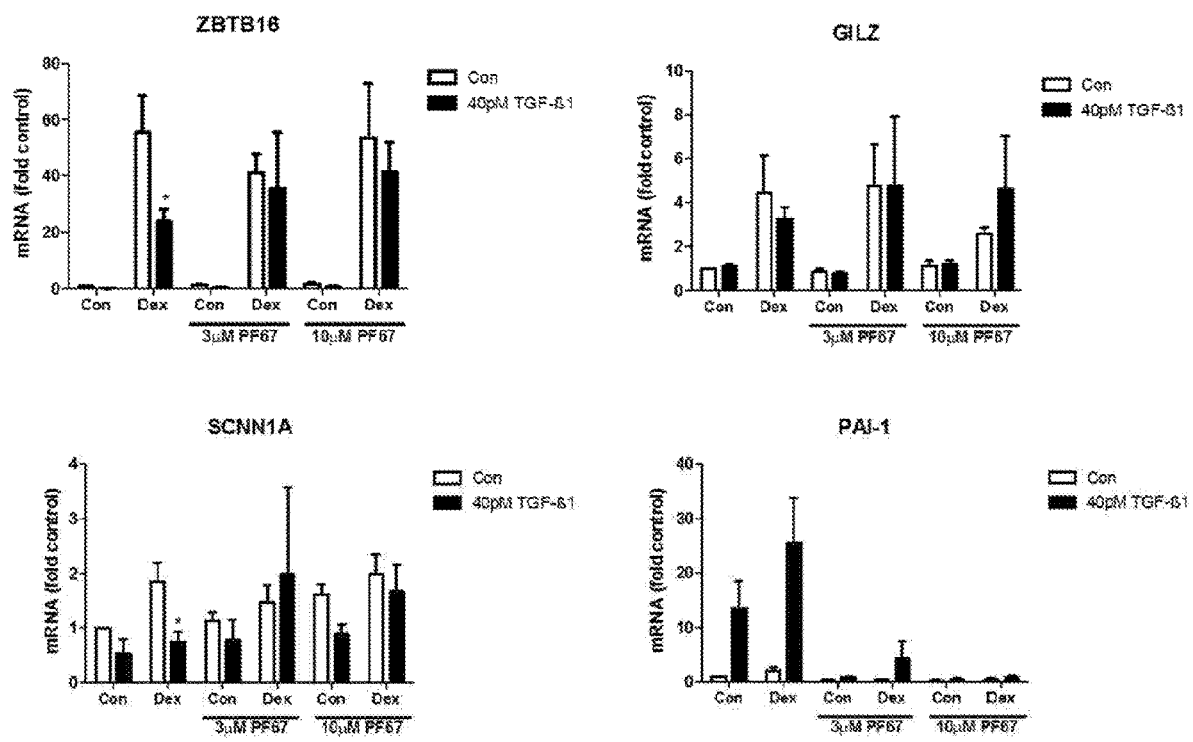
FIG. 25 shows the effects of PF670462 at 3 and 10 µM on the suppressant action of TGFβ on (Dex 30 nM)-induced expression of ZBTB16, GILZ, SCNNIA and PAI-1. These studies were undertaken in ALI-differentiated culture of primary human airway epithelial cells.

FIG. 25 shows the effects of PF670462 at 3 and 10 µM on the suppressant action of TGFβ on (Dex 30 nM)-induced expression of ZBTB16, GILZ, SCNNIA and PAI-1. These studies were undertaken in ALI-differentiated culture of primary human airway epithelial cells. Significant suppression of ZBTB16 and SCNNIA is prevented by 3 and 10 µM PF670462.

The recapitulation in ALI-differentiated human bronchial epithelial cells of both the TGFβ effect and its prevention by the same concentration range of PF670462 as is effective in BEAS2B cells indicates that the beneficial actions of this agent are manifest in a type of tissue that is analogous to the target tissue of an intended clinical use.

Example 21

The activity of PF670462 in enhancing glucocorticoid activity and antagonizing selected actions of TGFβ suggested potential for effectiveness in allergic disease which is partially controlled by glucocorticoids and in which there is a role for TGFβ.

FIG. 26 shows the dose-related increase in the lung expression of ZBTB116 and GILZ in mice exposed to an aerosol of PF670462 (0.03-10 mg/ml, 7 min). Un-anaesthetised Balb/C female mice were placed in an exposure chamber and received a 7 minute aerosol exposure to PF670462, 24 and 4 hours before lungs were harvested, extracted and mRNA levels measured by RT-qPCR.

ZBTB116 and GILZ are known to exert anti-inflammatory actions in by suppression of the master pro-inflammatory transcription factor, NFκB. These findings suggest that increased expression of these GRE-regulated genes, possibly as a result of enhancement of the actions of endogenous glucocorticoid, can be elicited by PF670462 prepared in a format suitable for clinical administration using a standard nebuliser (Hudson operated at a 5 L/min flow rate) to achieve particle size range for deposition in the peripheral airways.

Example 22

The conduct of the house dust mite allergy model with RSV complication was conducted as described herein and using the approaches described in Fuchs and Braun 2008 (Curr Drug Targets. 2008 June; 9(6):495-502).

Figure 27A:
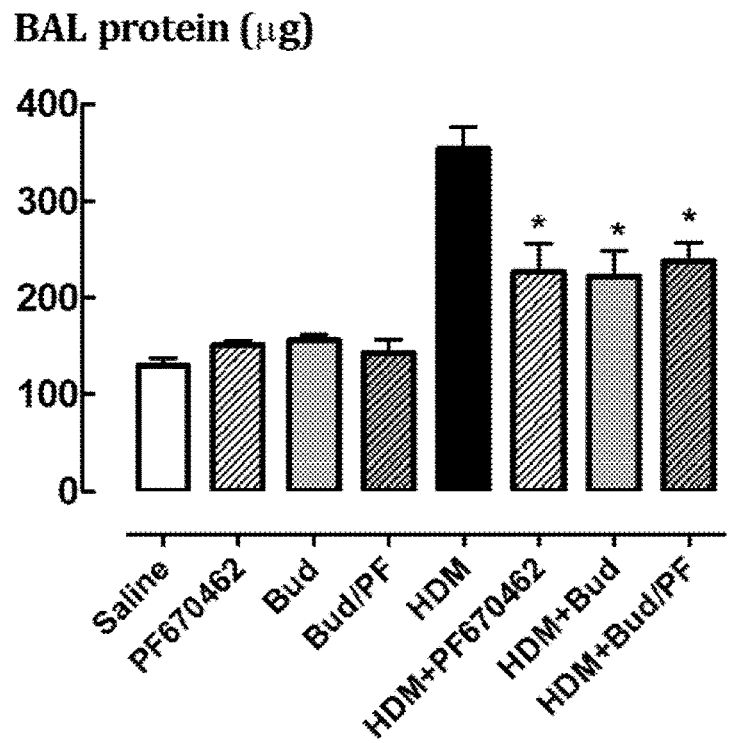
FIG. 27A shows that in mice challenged by daily intranasal insufflation of HDM allergen (25 µg/35 µL) there is an increase in the BAL protein level that is regulated by an aerosol of 3 mg/ml PF670462, Budesonide 0.5 mg/ml or by the combination of these treatments.
Figure 27B:
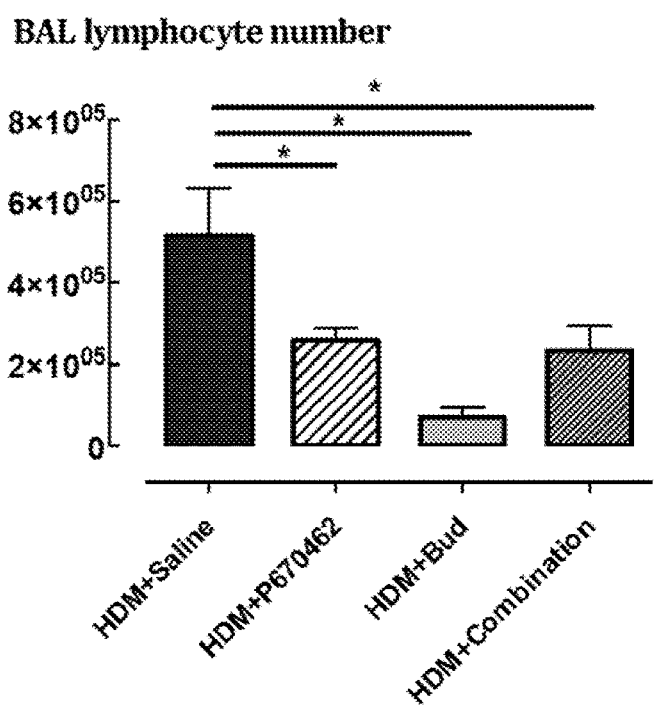
FIG. 27B shows lymphocyte number in BAL of the experiment described in Example 22 and FIG. 27A. Lymphocyte numbers in BAL were reduced by Bud, PF670462 or the combination.

FIG. 27A shows that in mice challenged by daily intra-nasal insufflation of HDM allergen (25 µg/35 µL) there is an increase in the BAL protein level that is regulated by an aerosol of 3 mg/ml PF670462, Budesonide 0.5 mg/ml or by the combination of these treatments. FIG. 27B shows lymphocyte number in BAL of the experiment described above and results in FIG. 27A. Lymphocyte numbers in BAL were reduced by Bud, PF670462 or the combination.

Figure 28:
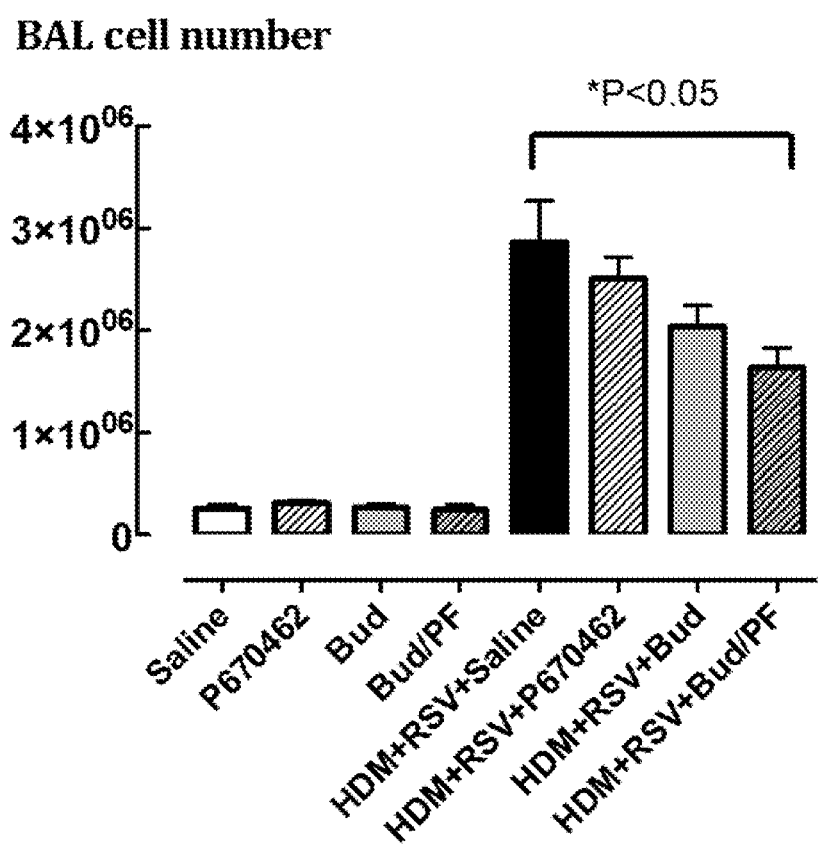
FIG. 28 shows BAL cell number in mice that have been challenged with HDM allergen and 3 days prior to post mortem, infected with 2 million RSV virions. The BAL cell number was not significantly reduced by either PF670462 or by Bud, but was reduced by the combination of these treatments.

FIG. 28 shows BAL cell number in mice that have been challenged with HDM allergen and 3 days prior to post mortem, infected with 2 million RSV virions. The BAL cell number was not significantly reduced by either PF670462 or by Bud, but was reduced by the combination of these treatments.

Figure 29:
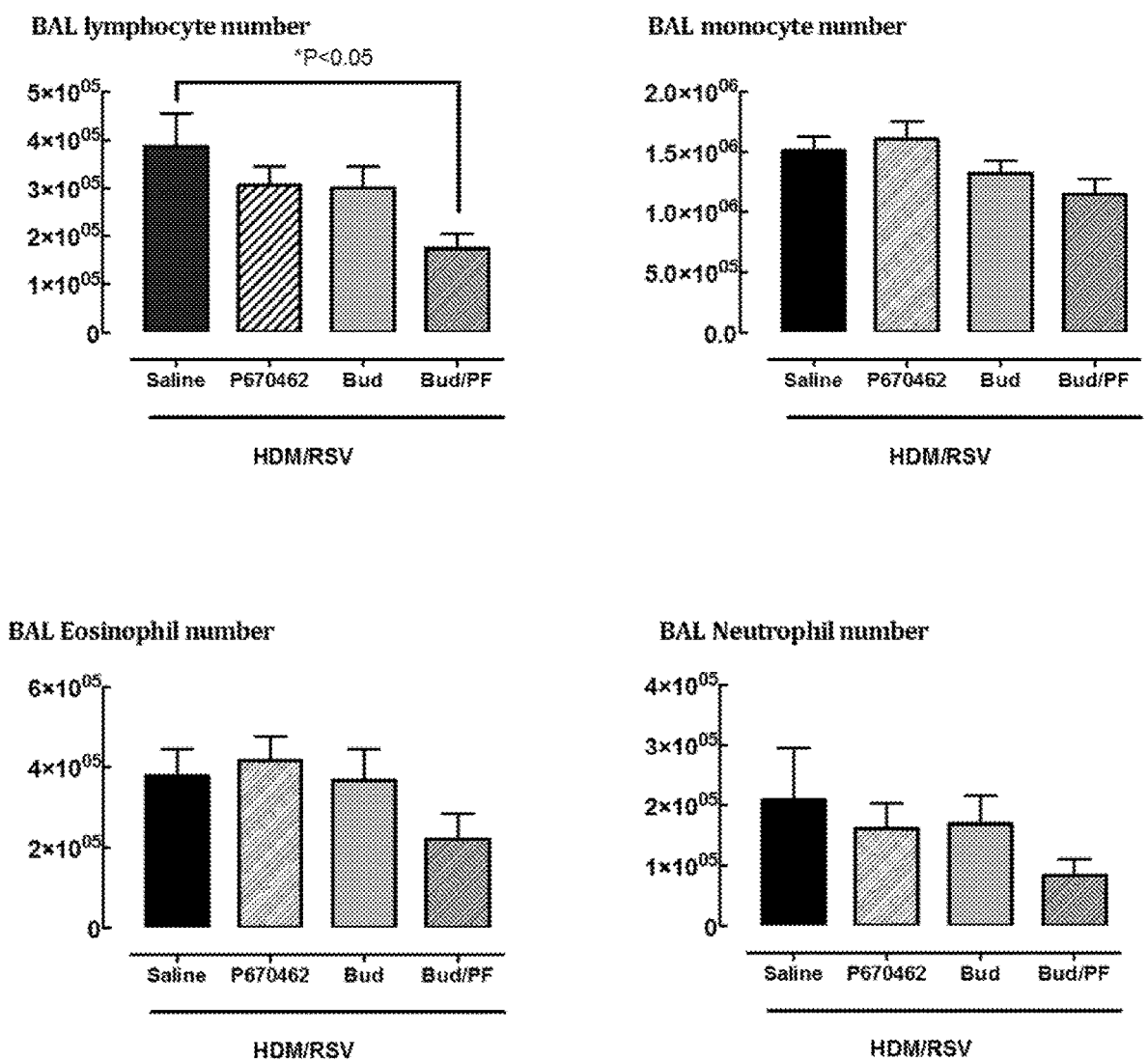
FIG. 29 shows the differential cell counts of the BAL cell numbers in mice challenged with HDM and then infected with RSV. The combination of Bud and PF670462 significantly reduced BAL lymphocyte numbers, but none of the treatments had significant effects on the other leukocyte subsets.

FIG. 29 shows the differential cell counts of the BAL cell numbers in mice challenged with HDM and then infected with RSV. The combination of Bud and PF670462 significantly reduced BAL lymphocyte numbers, but none of the treatments had significant effects on the other leukocyte subsets.

Figure 30:
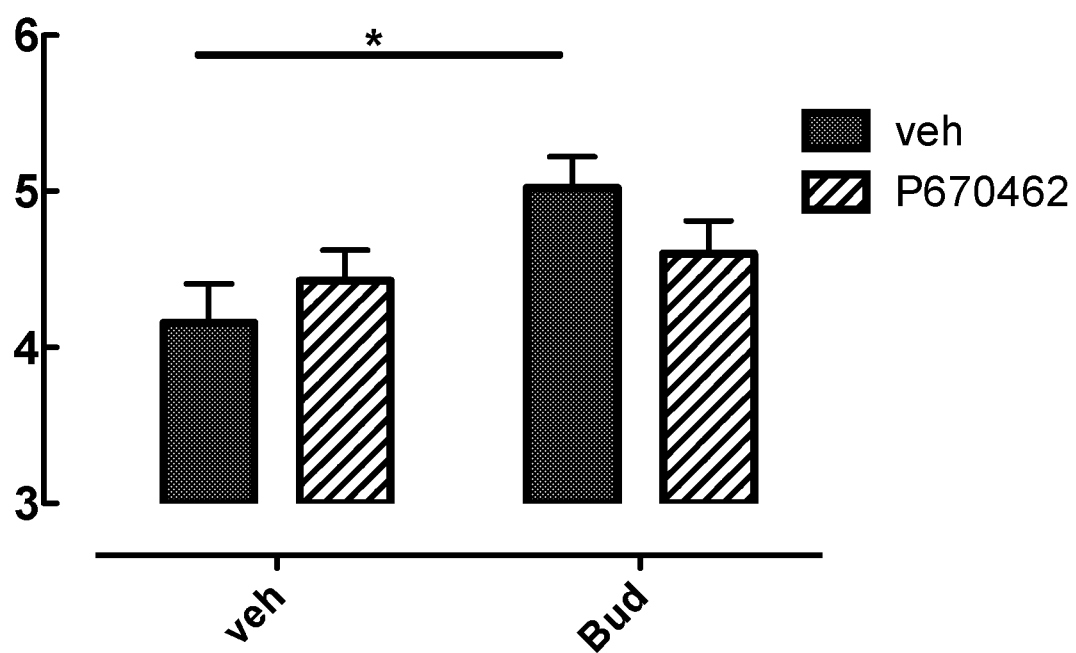
FIG. 30 shows that RSV titre is significantly increased by Bud alone, but not by either PF670462 or the combination of Bud and PF670462.

FIG. 30 shows that RSV titre is significantly increased by Bud alone, but not by either PF670462 or the combination of Bud and PF670462.

The significance of the findings in the HDM model and when it is exacerbated by RSV infection is that clinically useable formats of casein kinase inhibitors such as PF670462 and budesonide aerosols exert some directly detectable anti-allergic effects and also reduce the inflammation associated with the exacerbation as indicated by the reduction in inflammatory cell influx. These findings suggest benefit not only in allergic disease in the respiratory tract but also in its periodic exacerbation during viral infections. The increase in viral titre induced by budesonide treatment is consistent with other studies showing glucocorticoid enhancement of viral load in the respiratory tract and suggests that PF670462 may protect from this enhancement, consistent with its noted effects to increase BAL cell interferon levels.

The invention claimed is:
1. A method of alleviating or ameliorating a symptom of an interstitial lung disease, the method comprising administering to a subject in need thereof a therapeutically effective amount of a compound of the following structure:

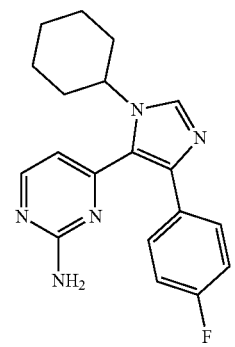 [SMILES: Nc1nccc(-c2c(-c3ccc(F)cc3)ncn2C2CCCCC2)n1]

or a pharmaceutically acceptable salt, polymorph, prodrug or solvate thereof, thereby alleviating or ameliorating a symptom of the interstitial lung disease in the subject.

2. A method according to claim 1, wherein the subject has a viral respiratory tract infection.

3. A method according to claim 1, wherein the subject has inflammation in the upper and lower respiratory tract that is associated with or caused by a viral infection.

4. A method according claim 1, further comprising the step of administering one or more glucocorticoids.

5. A method according to claim 4, wherein administering the one or more glucocorticoids is via inhalation and/or oral administration.

6. A method according to claim 4, wherein the glucocorticoid is dexamethasone, budesonide, ciclesonide, mometasone, methylprednisolone, prednisone, prednisolone, triamcinolone, or a combination thereof.

7. A method according to claim 2, wherein the viral respiratory tract infection is selected from the group consisting of rhinovirus (RV), respiratory syncytial virus (RSV) or influenza virus (InfV).

8. A method according to claim 3, wherein the viral infection is selected from the group consisting of rhinovirus (RV), respiratory syncytial virus (RSV) or influenza virus (InfV).

* * * * *